(12) United States Patent
Wood et al.

(10) Patent No.: US 8,343,990 B2
(45) Date of Patent: Jan. 1, 2013

(54) SUBSTITUTED CYCLOPROPYL COMPOUNDS, COMPOSITIONS CONTAINING SUCH COMPOUNDS AND METHODS OF TREATMENT

(75) Inventors: Harold B. Wood, Westfield, NJ (US); Jason W. Szewczyk, New York, NY (US); Yong Huang, Colonia, NJ (US); Alan D. Adams, Cranford, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 146 days.

(21) Appl. No.: 12/936,313

(22) PCT Filed: Mar. 26, 2009

(86) PCT No.: PCT/US2009/038315
§ 371 (c)(1),
(2), (4) Date: Oct. 4, 2010

(87) PCT Pub. No.: WO2009/129036
PCT Pub. Date: Oct. 22, 2009

(65) Prior Publication Data
US 2011/0028501 A1 Feb. 3, 2011

Related U.S. Application Data

(60) Provisional application No. 61/124,052, filed on Apr. 14, 2008.

(51) Int. Cl.
C07D 239/02 (2006.01)
C07D 413/14 (2006.01)
A61K 31/435 (2006.01)

(52) U.S. Cl. .......................... 514/275; 544/326; 544/328

(58) Field of Classification Search .................... None
See application file for complete search history.

(56) References Cited

FOREIGN PATENT DOCUMENTS

| WO | 97/28149 | 5/1997 |
|---|---|---|
| WO | 2005/007647 | 1/2005 |
| WO | 2005/121121 | 12/2005 |
| WO | 2006/067531 | 6/2006 |
| WO | 2006/067532 | 6/2006 |
| WO | 2007/003964 | 1/2007 |
| WO | 20071003962 | 1/2007 |

OTHER PUBLICATIONS

American Diabetes Association. Diabetes Care 2004, 27 (Supplement 1), S5-S10.*
Jones, R. M., Leonard, J. N., Buzard, D. J., Lehmann, J. Expert Opinion on Therapeutic Patents 2009, 19 (10), 1339-1359.*

* cited by examiner

*Primary Examiner* — Sreeni Padmanabhan
*Assistant Examiner* — Irina Neagu
(74) *Attorney, Agent, or Firm* — Anna L. Cocuzzo; John C. Todaro

(57) ABSTRACT

Substituted cyclopropyl compounds of formula (I) are disclosed as useful for treating or preventing type 2 diabetes and similar conditions. Pharmaceutically acceptable salts and solvates are included as well. The compounds are useful as agonists of the g-protein coupled receptor GPR-119.

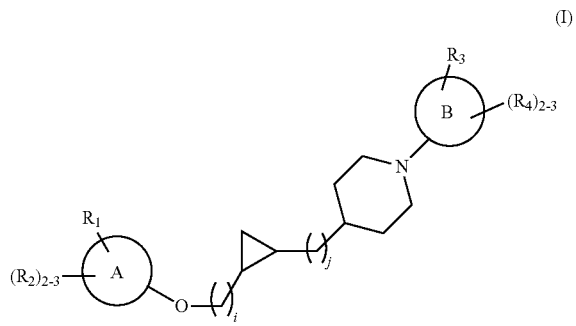

20 Claims, No Drawings

SUBSTITUTED CYCLOPROPYL COMPOUNDS, COMPOSITIONS CONTAINING SUCH COMPOUNDS AND METHODS OF TREATMENT

CROSS-REFERENCE TO RELATED APPLICATIONS

This application is a U.S. National Phase application under 35 U.S.C. §371 of PCT Application No. PCT/US2009/038315, filed Mar. 26, 2009, which published as WO 2009/129036 on Oct. 22, 2009, and claims priority under 35 U.S.C. §119 from U.S. Provisional Application No. 61/124,052, filed Apr. 14, 2008.

BACKGROUND OF THE INVENTION

The present invention relates to G-protein coupled receptor agonists. In particular, the present invention is directed to agonists of GPR 119 that are useful for the treatment of diabetes, especially type 2 diabetes, obesity, the metabolic syndrome and related diseases and conditions.

Diabetes is a disease derived from multiple causative factors. It is characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (T2DM), insulin is still produced in the body, and patients demonstrate resistance to the effects of insulin in stimulating glucose and lipid metabolism in the main insulin-sensitive tissues, namely, muscle, liver and adipose tissue. These patients often have normal levels of insulin, and may have hyperinsulinemia (elevated plasma insulin levels), as they compensate for the reduced effectiveness of insulin by secreting increased amounts of insulin.

Obesity is characterized by excessive adiposity relative to body mass. Clinically, obesity is defined by the body mass index [BMI=weight (kg)/height (m)$^2$], corresponding to BMI values≧30. Obesity and being overweight increases the risk of developing conditions such as high blood pressure, type 2 diabetes, heart disease, stroke, osteoarthritis, sleep apnea, gallbladder disease and cancer of the breast, prostate and colon. Higher body weights are also associated with increases in all-cause mortality.

There is renewed focus on pancreatic islet-based insulin secretion that is controlled by glucose-dependent insulin secretion. In this regard, several orphan G-protein coupled receptors (GPCR's) have recently been identified that are preferentially expressed in the 13-cell and are implicated in glucose dependent insulin secretion (GDIS). GPR119 is a cell-surface Gs-coupled GPCR that is highly expressed in human (and rodent) islets as well as in insulin-secreting cell lines. Synthetic GPR119 agonists augment the release of insulin from isolated static mouse islets only under conditions of elevated glucose, and improve glucose tolerance in diabetic mice and diet-induced obese (DIO) C57/B6 mice without causing hypoglycemia. GPR119 agonists therefore have the potential to function as anti-hyperglycemic agents that produce weight loss.

WO2005/007647 published on 27 Jan. 2005, WO2005/121121 published on 22 Dec. 2005 and WO2006/067531 published on 29 Jun. 2006 relate to GPR 119 agonist compounds.

SUMMARY OF THE INVENTION

A compound represented by the formula:

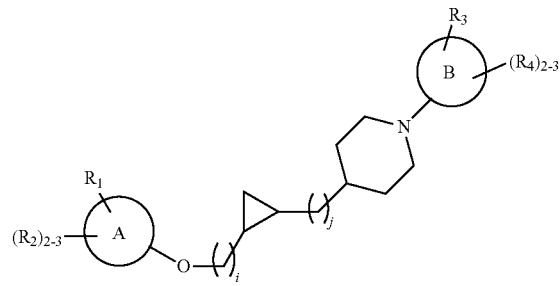

or a pharmaceutically acceptable salt or solvate thereof, wherein:

Ring A represents a 6-membered aryl or heteroaryl group containing 1 nitrogen atom, and optionally 1-2 additional nitrogen atoms;

Ring B represents a 6 membered heteroaryl ring containing 1-2 nitrogen atoms;

i and j independently represent integers selected from 0, 1 and 2, such that i plus j is 1 or 2;

$R^1$ represents a member selected from the group consisting of H, halo, $C_{1-6}$alkyl, halo$C_{1-6}$alkyl, C(O)$C_{1-6}$alkyl, C(O)halo$C_{1-6}$alkyl, C(O)NH—$C_{1-6}$alkyl, S(O)$C_{1-6}$alkyl, SO$_2C_{1-6}$alkyl, SO$_2$NH$_2$, SO$_2$NHC$_{1-6}$alkyl, SO$_2$N(C$_1$alkyl)$_2$, CN, and HAR optionally substituted with 1-3 $C_{1-6}$alkyl, halo or halo $C_{1-6}$alkyl groups;

and each $R^2$, $R^3$ and $R^4$ is independently selected from H, halo, $C_{1-6}$ alkyl and halo$C_{1-6}$alkyl.

DETAILED DESCRIPTION OF THE INVENTION

The invention is described herein in detail using the terms defined below unless otherwise specified.

"Alkyl", as well as other groups having the prefix "alk", such as alkoxy, and the like, means carbon chains which may be linear, branched, or cyclic, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-7 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like. Haloalkoxy and haloOalkyl are used interchangeably and refer to halo substituted alkyl groups linked through the oxygen atom. Haloalkyl and haloalkoxy include mono-substituted as well as multiple substituted alkyl and alkoxy groups, up to perhalo substituted alkyl and alkoxy. For example, trifluoromethyl and trifluoromethoxy are included.

"Aryl" (Ar) means phenyl or naphthyl, preferably phenyl.

"Heteroaryl" (HAR) unless otherwise specified, means monocyclic aromatic ring systems containing 5-6 atoms, at least one of which is a heteroatom selected from O, S, S(O), $SO_2$ and N. Examples include, but are not limited to, pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl and the like. Heteroaryl also includes such groups in charged form, e.g., pyridinium.

"Halogen" (Halo) includes fluorine, chlorine, bromine and iodine.

One aspect of the invention that is of interest relates to a compound represented by the formula:

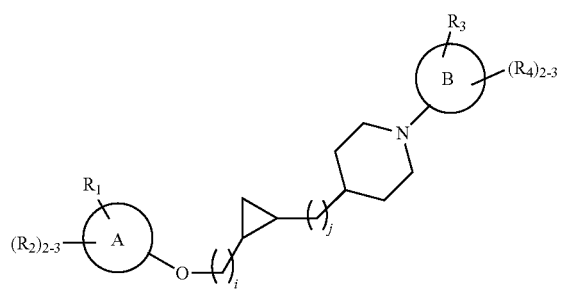

I or a pharmaceutically acceptable salt or solvate thereof, wherein:

Ring A represents a 6-membered aryl or heteroaryl group containing 1 nitrogen atom, and optionally 1-2 additional nitrogen atoms;

Ring B represents a 6 membered heteroaryl ring containing 1-2 nitrogen atoms;

i and j independently represent integers selected from 0, 1 and 2, such that i plus j is 1 or 2;

$R^1$ represents a member selected from the group consisting of H, halo, $C_{1-6}$alkyl, halo$C_{1-6}$alkyl, $C(O)C_{1-6}$alkyl, $C(O)$halo$C_{1-6}$alkyl, $C(O)NH-C_{1-6}$alkyl, $S(O)C_{1-6}$alkyl, $SO_2C_{1-6}$alkyl, $SO_2NH_2$, $SO_2NHC_{1-6}$alkyl, $SO_2N(C_{1-6}$alkyl$)_2$, CN, and HAR optionally substituted with 1-3 $C_{1-6}$alkyl, halo or halo $C_{1-6}$alkyl groups;

and each $R^2$, $R^3$ and $R^4$ is independently selected from H, halo, $C_{1-6}$alkyl and halo$C_{1-6}$alkyl.

An aspect of the invention that is of interest relates to compounds of formula I, or a pharmaceutically acceptable salt or solvate thereof, wherein ring A is selected from the group consisting of Aryl which is phenyl, and Heteroaryl selected from the group consisting of pyridine, pyrimidine and pyrazine.

In particular, an aspect of the invention that is of interest relates to compounds of formula I, or a pharmaceutically acceptable salt or solvate thereof, wherein ring A is selected from the group consisting of phenyl and pyrimidine.

Even more particularly, an aspect of the invention that is of interest relates to compounds of formula I, or a pharmaceutically acceptable salt or solvate thereof, wherein ring A is a pyrimidine ring.

Another aspect of the invention that is of interest relates to compounds of formula I, or a pharmaceutically acceptable salt or solvate thereof, wherein ring B is selected from the group consisting of pyridine, pyrimidine and pyrazine.

More particularly, another aspect of the invention that is of interest relates to compounds of formula I, or a pharmaceutically acceptable salt or solvate thereof, wherein ring B is represents pyrimidine.

Another aspect of the invention that is of interest relates to compounds of formula I, or a pharmaceutically acceptable salt thereof, wherein i and j represent 0, 1 or 2, such that the sum of i and j is 2.

Another aspect of the invention that is of interest relates to compounds of formula I, or a pharmaceutically acceptable salt or solvate, thereof wherein $R^1$ is selected from the group consisting of H, halo which is F or Br, $C_{1-3}$alkyl, halo$C_{1-3}$alkyl, $C(O)NHC_{2-4}$alkyl, $S(O)C_{1-3}$alkyl, $SO_2C_{1-3}$alkyl, $SO_2NHC_{1-3}$alkyl, CN and HAR which is a 5 membered heteroaromatic ring containing one nitrogen atom, optionally 1-3 additional nitrogen atoms, and optionally one oxygen atom, said heteroaryl being optionally substituted with one $C_{1-3}$alkyl group.

An aspect of the invention that is of particular interest relates to compounds of formula I, or a pharmaceutically acceptable salt or solvate thereof, wherein $R^1$ is selected from the group consisting of: H, halo which is F or Br, $C_{1-3}$alkyl, $CF_3$, $C(O)NH$-cyclopropyl, $S(O)CH_3$, $SO_2CH_3$, $SO_2NH$cyclopropyl, CN and HAR which is selected from the group consisting of: oxadiazole, triazole and tetrazole, said group being optionally substituted with methyl or cyclopropyl.

Even more particularly, an aspect of the invention that is of interest relates to compounds of formula I, or a pharmaceutically acceptable salt or solvate thereof, wherein Ring A represents a phenyl ring and $R^1$ represents a five membered heteroaryl ring selected from the group consisting of oxadiazole, triazole and tetrazole, said ring being optionally substituted with methyl or cyclopropyl.

Further, an aspect of the invention that is of interest relates to compounds of formula I, or a pharmaceutically acceptable salt or solvate thereof, wherein Ring A represents a pyridine or pyrimidine ring and $R^1$ represents CN, $CF_3$, or a five membered heteroaryl ring selected from the group consisting of oxadiazole, triazole and tetrazole, said ring being optionally substituted with methyl or cyclopropyl.

Another aspect of the invention that is of interest relates to compounds of formula I, or a pharmaceutically acceptable salt or solvate thereof, wherein $R^2$ represents H, halo selected from F and Cl, $CH_3$ and $CF_3$.

Another aspect of the invention that is of interest relates to compounds of formula I, or a pharmaceutically acceptable salt or solvate thereof, wherein $R^3$ and $R^4$ represent H, halo selected from F and Cl, $CH_3$ and $CF_3$.

Another aspect of the invention that is of particular interest relates to compounds of formula I, or a pharmaceutically acceptable salt or solvate thereof, wherein:

ring A is selected from the group consisting of Aryl which is phenyl, and Heteroaryl selected from the group consisting of pyridine, pyrimidine and pyrazine;

ring B is selected from the group consisting of pyridine, pyrimidine and pyrazine;

i and j represent 0, 1 or 2, such that the sum of i and j is 2;

$R^1$ is selected from the group consisting of: H, halo which is F or Br, halo$C_{1-3}$alkyl, $C(O)NHC_{2-4}$alkyl, $S(O)C_{1-3}$alkyl, $SO_2C_{1-3}$alkyl, $SO_2NHC_{1-3}$alkyl, CN and HAR which is a 5 membered heteroaromatic ring containing one nitrogen atom, optionally 1-3 additional nitrogen atoms, and optionally one oxygen atom, said heteroaryl being optionally substituted with one $_{1-3}$alkyl group;

$R^2$ represents H, halo selected from F and Cl, $CH_3$ and $CF_3$, and $R^3$ and $R^4$ represent H, halo selected from F and Cl, $CH_3$ and $CF_3$.

Another aspect of the invention that is of interest relates to compounds of formula I or a pharmaceutically acceptable salt or solvate thereof wherein the cyclopropyl ring is the cis cyclopropyl isomer.

Examples of compounds that are of interest are provided below in the table.

| Compound Name |
| --- |
| rac cis-5-chloro-2-[4-(2-{2-[4-(methylsulfonyl)phenoxy]ethyl}cyclopropyl)piperidin-1-yl]pyrimidine, 5-chloro-2-[4-((1S,2R)-2-{2-[4-(methylsulfonyl)phenoxy]ethyl}cyclopropyl)piperidin-1-yl]pyrimidine and 5-chloro-2-[4-((1R,2S)-2-{2-[4-(methylsulfonyl)phenoxy]ethyl}cyclopropyl) piperidin-1-yl]pyrimidine |
| rac-cis 5-chloro-2-{4-[2-(2-{[5-(methylsulfonyl)pyridin-2-yl]oxy}ethyl)cyclopropyl] piperidin-1-yl}pyrimidine, cis 5-chloro-2-{4-[(1S,2R)-2-(2-{[5-(methylsulfonyl)pyridin-2-yl]oxy}ethyl)cyclopropyl]piperidin-1-yl}pyrimidine, cis 5-chloro-2-{4-[(1R,2S)-2-(2-{[5-(methylsulfonyl)pyridin-2-yl]oxy}ethyl)cyclopropyl]piperidin-1-yl}pyrimidine |
| rac cis-5-chloro-2-[4-(2-{2-[3-(methylsulfonyl)phenoxy]ethyl}cyclopropyl)piperidin-1-yl]pyrimidine |
| rac cis-5-chloro-2-[4-(2-{2-[3-(5-methyl-1,3,4-oxadiazol-2-yl)phenoxy]ethyl}cyclopropyl)piperidin-1-yl]pyrimidine |
| rac cis-5-chloro-2-[4-(2-{2-[3-(1H-1,2,4-triazol-1-yl)phenoxy]ethyl}cyclopropyl)piperidin-1-yl]pyrimidine |
| rac cis-5-chloro-2-[4-(2-{2-[3-(1,3,4-oxadiazol-2-yl)phenoxy]ethyl}cyclopropyl)piperidin-1-yl]pyrimidine |
| rac cis-4-(2-{2-[1-(5-chloropyrimidin-2-yl)piperidin-4-yl]cyclopropyl}ethoxy)-N-cyclopropyl-2-fluorobenzamide |
| rac cis-4-(2-{2-[1-(5-chloropyrimidin-2-yl)piperidin-4-yl]cyclopropyl}ethoxy)-2-fluorobenzonitrile |
| rac cis-5-chloro-2-[4-(2-{2-[4-(cyclopropylsulfonyl)phenoxy]ethyl}cyclopropyl)piperidin-1-yl]pyrimidine |
| rac cis-5-chloro-2-[4-(2-{2-[3-fluoro-4-(5-methyl-1,3,4-oxadiazol-2-yl)phenoxy]ethyl}cyclopropyl)piperidin-1-yl]pyrimidine |
| rac cis-5-chloro-2-[4-(2-{2-[4-(1,3,4-oxadiazol-2-yl)phenoxy]ethyl}cyclopropyl)piperidin-1-yl]pyrimidine |
| rac cis-5-chloro-2-[4-(2-{2-[4-(5-methyl-1,3,4-oxadiazol-2-yl)phenoxy]ethyl}cyclopropyl)piperidin-1-yl]pyrimidine |
| rac cis-5-chloro-2-[4-(2-{2-[4-(1,2,4-oxadiazol-3-yl)phenoxy]ethyl}cyclopropyl)piperidin-1-yl]pyrimidine |
| rac cis-5-chloro-2-[4-(2-{2-[4-(1,2,4-oxadiazol-5-yl)phenoxy]ethyl}cyclopropyl)piperidin-1-yl]pyrimidine |
| rac cis-5-chloro-2-[4-(2-{2-[4-(1,3-oxazol-4-yl)phenoxy]ethyl}cyclopropyl)piperidin-1-yl]pyrimidine |
| rac cis-5-chloro-2-(4-{2-[2-(4-isoxazol-4-ylphenoxy)ethyl]cyclopropyl}piperidin-1-yl)pyrimidine |
| rac cis-5-chloro-2-(4-{2-[2-(4-isoxazol-5-ylphenoxy)ethyl]cyclopropyl}piperidin-1-yl)pyrimidine |
| rac cis-5-chloro-2-[4-(2-{2-[4-(1H-pyrazol-3-yl)phenoxy]ethyl}cyclopropyl)piperidin-1-yl]pyrimidine |
| rac cis-5-chloro-2-[4-(2-{2-[4-(1H-pyrazol-4-yl)phenoxy]ethyl}cyclopropyl)piperidin-1-yl]pyrimidine |
| rac cis-5-chloro-2-[4-(2-{2-[4-(1H-pyrazol-1-yl)phenoxy]ethyl}cyclopropyl)piperidin-1-yl]pyrimidine |
| rac cis-5-chloro-2-[4-(2-{2-[4-(1H-1,2,4-triazol-1-yl)phenoxy]ethyl}cyclopropyl)piperidin-1-yl]pyrimidine |
| rac cis-5-chloro-2-[4-(2-{2-[4-(4H-1,2,4-triazol-4-yl)phenoxy]ethyl}cyclopropyl)piperidin-1-yl]pyrimidine |
| rac cis-5-chloro-2-[4-(2-{2-[4-(1H-1,2,3-triazol-1-yl)phenoxy]ethyl}cyclopropyl)piperidin-1-yl]pyrimidine |
| rac-cis-5-fluoro-2-[4-(2-{2-[4-(1H-1,2,3-triazol-1-yl)phenoxy]ethyl}cyclopropyl)piperidin-1-yl]pyrimidine |
| rac cis-5-methyl-2-[4-(2-{2-[4-(1H-1,2,3-triazol-1-yl)phenoxy]ethyl}cyclopropyl)piperidin-1-yl]pyrimidine |
| rac cis-5-chloro-2-[4-(2-{2-[4-(2H-1,2,3-triazol-2-yl)phenoxy]ethyl}cyclopropyl)piperidin-1-yl]pyrimidine |
| rac cis-5-chloro-2-[4-(2-{2-[4-(1H-1,2,3-triazol-5-yl)phenoxy]ethyl}cyclopropyl)piperidin-1-yl]pyrimidine |
| rac cis-5-chloro-2-[4-(2-{2-[4-(1H-tetrazol-1-yl)phenoxy]ethyl}cyclopropyl)piperidin-1-yl]pyrimidine |
| rac cis-5-chloro-2-[4-(2-{2-[3-fluoro-4-(1H-tetrazol-1-yl)phenoxy]ethyl}cyclopropyl)piperidin-1-yl]pyrimidine |
| rac cis-5-fluoro-2-[4-(2-{2-[3-fluoro-4-(1H-tetrazol-1-yl)phenoxy]ethyl}cyclopropyl)piperidin-1-yl]pyrimidine |
| rac cis-2-[4-(2-{2-[3-fluoro-4-(1H-tetrazol-1-yl)phenoxy]ethyl}cyclopropyl)piperidin-1-yl]-5-methylpyrimidine |
| rac cis-5-chloro-2-[4-(2-{2-[4-(2H-tetrazol-2-yl)phenoxy]ethyl}cyclopropyl)piperidin-1-yl]pyrimidine |
| rac cis-5-chloro-2-[4-(2-{2-[4-(5-methyl-2H-tetrazol-2-yl)phenoxy]ethyl}cyclopropyl)piperidine-1-yl]pyrimidine |
| rac cis-5-chloro-2-[4-(2-{2-[4-(5-methyl-1H-tetrazol-1-yl)phenoxy]ethyl}cyclopropyl)piperidin-1-yl]pyrimidine |
| rac cis-5-chloro-2-[4-(2-{2-[3-fluoro-4-(5-methyl-1,3,4-oxadiazol-2-yl)phenoxy]ethyl}cyclopropyl)piperidin-1-yl]pyrimidine |
| rac-cis-5-chloro-2-[4-(2-{2-[4-(methylsulfinyl)phenoxy]ethyl}cyclopropyl)piperidin-1-yl]pyrimidine |
| Chiral-cis-6-(2-{2-[1-(5-chloropyrimidin-2-yl)piperidin-4-yl]cyclopropyl}ethoxy)-2-methylpyrimidine-4-carbonitrile, cis 6-(2-{(1S,2R)-2-{1-(5-chloropyrimidin-2-yl)piperidin-4- |

| Compound Name |
| --- | yl]cyclopropyl}ethoxy)-2-methylpyrimidine-4-carbonitrile, cis 6-(2-{(1R, 2S)-2-{1-(5-chloropyrimidin-2-yl)piperidin-4-yl]cyclopropyl}ethoxy)-2-methylpyrimidine-4-carbonitrile
Rac-cis-1-[4-(2-{2-[1-(5-chloropyrimidin-2-yl)piperidin-4-yl]cyclopropyl}ethoxy)phenyl]ethanone
Rac-cis-2-methyl-6-(2-{2-[1-(5-methylpyrazin-2-yl)piperidin-4-yl]cyclopropyl}ethoxy)pyrimidine-4-carbonitrile
Rac-cis-6-(2-{2-[1-(5-chloropyrimidin-2-yl)piperidin-4-yl]cyclopropyl}ethoxy)pyrimidine-4-carbonitrile
Rac-cis-4-(2-{2-[1-(5-chloropyrimidin-2-yl)piperidin-4-yl]cyclopropyl}ethoxy)pyrimidine-2-carbonitrile
Chiral-cis-2-methyl-6-(2-{2-[1-(5-methylpyrimidin-2-yl)piperidin-4-yl]cyclopropyl}ethoxy)pyrimidine-4-carbonitrile, cis-2-methyl-6-(2-{(1S,2R)-2-[1-(5-methylpyrimidin-2-yl)piperidin-4-yl]cyclopropyl}ethoxy)pyrimidine-4-carbonitrile, cis-2-methyl-6-(2-{(1R, 2S)-2-[1-(5-methylpyrimidin-2-yl)piperidin-4-yl]cyclopropyl}ethoxy)pyrimidine-4-carbonitrile
Rac-cis-2-methyl-6-(2-{2-[1-(5-methylpyrimidin-2-yl)piperidin-4-yl]cyclopropyl}ethoxy)pyrimidine-4-carbonitrile
Rac-cis-2,4-dimethyl-6-(2-{2-[1-(5-methylpyrimidin-2-yl)piperidin-4-yl]cyclopropyl}ethoxy)pyrimidine
Rac-cis-6-(2-{2-[1-(5-chloro-4-methylpyrimidin-2-yl)piperidin-4-yl]cyclopropyl}ethoxy)-2-methylpyrimidine-4-carbonitrile
Rac-cis-6-(2-{2-[1-(5-chloropyridin-2-yl)piperidin-4-yl]cyclopropyl}ethoxy)-2-methylpyrimidine-4-carbonitrile
Rac-cis-6-(2-{2-[1-(4,5-dimethylpyrimidin-2-yl)piperidin-4-yl]cyclopropyl}ethoxy)-2-methylpyrimidine-4-carbonitrile
Rac-cis-6-(2-{2-[1-(5-chloro-4-methylpyridin-2-yl)piperidin-4-yl]cyclopropyl}ethoxy)-2-methylpyrimidine-4-carbonitrile
Rac-cis-6-(2-{2-[1-(5-fluoro-4-methylpyrimidin-2-yl)piperidin-4-yl]cyclopropyl}ethoxy)-2-methylpyrimidine-4-carbonitrile
Rac-cis-2-methyl-6-[2-(2-{1-[5-(trifluoromethyl)pyridin-2-yl]piperidin-4-yl}cyclopropyl)ethoxy]pyrimidine-4-carbonitrile
Rac-cis-5-chloro-2-(4-{2-[2-(pyridin-3-yloxy)ethyl]cyclopropyl}piperidin-1-yl)pyrimidine
Rac-cis-5-chloro-2-(4-{2-[2-(pyrimidin-4-yloxy)ethyl]cyclopropyl}piperidin-1-yl)pyrimidine
Rac-cis-5-(2-{2-[1-(5-chloropyrimidin-2-yl)piperidin-4-yl]cyclopropyl}ethoxy)nicotinonitrile
Rac-cis-6-(2-{2-[1-(5-chloropyrimidin-2-yl) piperidin-4-yl] cyclopropyl} ethoxy)-2-methylpyrimidine-4-carbonitrile
Rac-cis-4-(2-{2-[1-(5-chloropyrimidin-2-yl)piperidin-4-yl]cyclopropyl} ethoxy)-6-methylpyrimidine-2-carbonitrile
Rac-cis-6-(2-{2-[1-(5-fluoropyrimidin-2-yl)piperidin-4-yl]cyclopropyl}ethoxy)-2-methylpyrimidine-4-carbonitrile
Rac-cis-5-(2-{2-[1-(5-chloropyrimidin-2-yl)piperidin-4-yl]cyclopropyl}ethoxy)pyridine-2-carbonitrile
Rac-cis-5-chloro-2-(4-{2-[2-(pyridin-4-yloxy)ethyl]cyclopropyl}piperidin-1-yl)pyrimidine
Chiral cis-5-chloro-2-{4-[2-(2-{[5-(1H-1,2,3-triazol-1-yl)pyridin-2-yl]oxy}ethyl)cyclopropyl]piperidin-1-yl}pyrimidine, cis-5-chloro-2-{4-(1S,2R)-[2-(2-{[5-(1H-1,2,3-triazol-1-yl)pyridin-2-yl]oxy}ethyl)cyclopropyl]piperidin-1-yl}pyrimidine, cis-5-chloro-2-{4-(1R,2S)-[2-(2-{[5-(1H-1,2,3-triazol-1-yl)pyridin-2-yl]oxy}ethyl)cyclopropyl]piperidin-1-yl}pyrimidine
5-chloro-2-[4-((1R,2S)-2-{2-[3-fluoro-4-(5-methyl-1,3,4-oxadiazol-2-yl)phenoxy]ethyl}cyclopropyl)piperidin-1-yl]pyrimidine and 5-chloro-2-[4-((1S,2R)-2-{2-[3-fluoro-4-(5-methyl-1,3,4-oxadiazol-2-yl)phenoxy]ethyl}cyclopropyl)piperidin-1-yl]pyrimidine
5-chloro-2-[4-((1S,2R)-2-{2-[4-(1H-1,2,3-triazol-1-yl)phenoxy]ethyl}cyclopropyl)piperidin-1-yl]pyrimidine and 5-chloro-2-[4-((1R,2S)-2-{2-[4-(1H-1,2,3-triazol-1-yl)phenoxy]ethyl}cyclopropyl)piperidin-1-yl]pyrimidine
5-fluoro-2-[4-((1R,2S)-2-{2-[4-(1H-1,2,3-triazol-1-yl)phenoxy]ethyl}cyclopropyl)piperidin-1-yl]pyrimidine and 5-fluoro-2-[4-((1S,2R)-2-{2-[4-(1H-1,2,3-triazol-1-yl)phenoxy]ethyl}cyclopropyl)piperidin-1-yl]pyrimidine
5-chloro-2-[4-((1R,2S)-2-{2-[4-(1H-tetrazol-1-yl)phenoxy]ethyl}cyclopropyl)piperidin-1-yl]pyrimidine and 5-chloro-2-[4-((1S,2R)-2-{2-[4-(1H-tetrazol-1-yl)phenoxy]ethyl}cyclopropyl)piperidin-1-yl]pyrimidine
5-chloro-2-[4-((1R,2S)-2-{2-[3-fluoro-4-(1H-tetrazol-1-yl)phenoxy]ethyl}cyclopropyl)piperidin-1-yl]pyrimidine and 5-chloro-2-[4-((1S,2R)-2-{2-[3-fluoro-4-(1H-tetrazol-1-yl)phenoxy]ethyl}cyclopropyl)piperidin-1-yl]pyrimidine
5-fluoro-2-[4-((1R,2S)-2-{2-[3-fluoro-4-(5-methyl-1,3,4-oxadiazol-2-yl)phenoxy]ethyl}cyclopropyl)piperidin-1-yl]pyrimidine and 5-fluoro-2-[4-((1S,2R)-2-{2-[3-fluoro-4-(5-methyl-1,3,4-oxadiazol-2-yl)phenoxy]ethyl}cyclopropyl)piperidin-1-yl]pyrimidine
rac-cis-2-[4-(2-{2-[3-fluoro-4-(5-methyl-1,3,4-oxadiazol-2-yl)phenoxy]ethyl}cyclopropyl)piperidin-1-yl]-5-methylpyrimidine
Rac-cis-2-[4-(2-{2-[3-fluoro-4-(5-methyl-1,3,4-oxadiazol-2-yl)phenoxy]ethyl}cyclopropyl)piperidin-1-yl]pyrimidine
Rac-cis-5-fluoro-2-[4-(2-{2-[3-fluoro-4-(5-methyl-1,3,4-oxadiazol-2-y)phenoxy]ethyl}cyclopropyl)piperidin-1-yl]pyrimidine
Rac-cis-5-chloro-2-[4-(2-{2-[3-fluoro-4-(5-methyl-1,3,4-oxadiazol-2-yl)phenoxy]ethyl}cyclopropyl)piperidin-1-yl]-4-methylpyrimidine
Rac-cis-3,5-dichloro-2-[4-(2-{2-[3-fluoro-4-(5-methyl-1,3,4-oxadiazol-2-yl)phenoxy]ethyl}cyclopropyl)piperidin-1-yl]pyridine
Rac-cis-2-[4-(2-{2-[3-fluoro-4-(5-methyl-1,3,4-oxadiazol-2-yl)phenoxy]ethyl}cyclopropyl)piperidin-1-yl]-5-(trifluoromethyl)pyridinium trifluoroacetate

| Compound Name |
| --- |
| rac-trans-5-chloro-2-[4-(2-{2-[4-(methylsulfonyl)phenoxy]ethyl}cyclopropyl)piperidin-1-yl]pyrimidine |
| rac-trans-5-chloro-2-(4-{2-[2-(pyridin-4-yloxy)ethyl]cyclopropyl}piperidin-1-yl)pyrimidine |
| 4-(2-{(1R,2R)-2-[1-(5-chloropyrimidin-2-yl)piperidin-4-yl]cyclopropyl}ethoxy)-N-cyclopropyl-2-fluorobenzamide |
| 4-(2-{(1R,2R)-2-[1-(5-chloropyrimidin-2-yl)piperidin-4-yl]cyclopropyl}ethoxy)-2-fluorobenzonitrile |
| 5-chloro-2-[4-((1R,2R)-2-{2-[4-(1H-1,2,4-triazol-1-yl)phenoxy]ethyl}cyclopropyl)piperidin-1-yl]pyrimidine |
| 5-chloro-2-[4-((1R,2R)-2-{2-[3-fluoro-4-(5-methyl-1,3,4-oxadiazol-2-yl)phenoxy]ethyl}cyclopropyl)piperidin-1-yl]pyrimidine |
| 5-chloro-2-[4-((1R,2R)-2-{2-[4-(5-cyclopropyl-1,3,4-oxadiazol-2-yl)-3-fluorophenoxy]ethyl}cyclopropyl)piperidin-1-yl]pyrimidine |
| rac-trans-5-chloro-2-(4-{2-[2-(pyridin-4-yloxy)ethyl]cyclopropyl}piperidin-1-yl)pyrimidine |
| rac-trans-4-(2-{2-[1-(5-chloropyrimidin-2-yl) piperidin-4-yl]cyclopropyl} ethoxy)-6-methylpyrimidine-2-carbonitrile |
| rac trans 6-(2-{2-[1-(5-chloropyrimidin-2-yl)piperidin-4-yl] cyclopropyl} ethoxy)-2-methylpyrimidine-4-carbonitrile |
| rac-trans-5-chloro-2-{4-[(2-{[4-(methylsulfonyl)phenoxy]methyl}cyclopropyl)methyl]piperidin-1-yl}pyrimidine |
| 5-chloro-2-[4-((1R,2R)-2-{2-[4-(methylsulfonyl)phenoxy]ethyl} cyclopropyl)piperidin-1-yl]pyrimidine |
| 5-chloro-2-{4-[((1S,2S)-2-{[4-(methylsulfonyl)phenoxy]methyl}cyclopropyl)methyl]piperidin-1-yl}pyrimidine |
| Rac-trans-4-[(2-{[1-(5-chloropyrimidin-2-yl)piperidin-4-yl]methyl}cyclopropyl)methoxy]-2-fluorobenzonitrile |
| 4-[((1R,2R)-2-{[1-(5-chloropyrimidin-2-yl)piperidin-4-yl]methyl}cyclopropyl)methoxy]-2-fluorobenzonitrile |
| Rac-trans 4-[(2-{[1-(5-chloropyrimidin-2-yl)piperidin-4-yl]methyl}cyclopropyl)methoxy]-N-cyclopropyl-2-fluorobenzamide |
| 4-[((1R,2R)-2-{[1-(5-chloropyrimidin-2-yl)piperidin-4-yl]methyl}cyclopropyl)methoxy]-N-cyclopropyl-2-fluorobenzamide |
| 4-[((1S,2S)-2-{[1-(5-chloropyrimidin-2-yl)piperidin-4-yl]methyl}cyclopropyl)methoxy]-N-cyclopropyl-2-fluorobenzamide |
| 5-chloro-2-{4-[((1R,2R)-2-{[3-fluoro-4-(5-methyl-1,3,4-oxadiazol-2-yl)phenoxy]methyl}cyclopropyl)methyl]piperidin-1-yl}pyrimidine |
| 5-chloro-2-{4-[((1S,2S)-2-{[3-fluoro-4-(5-methyl-1,3,4-oxadiazol-2-yl)phenoxy]methyl}cyclopropyl)methyl]piperidin-1-yl}pyrimidine |
| rac-trans 5-chloro-2-{4-[(2-{[4-(5-cyclopropyl-1,3,4-oxadiazol-2-yl)-3-fluorophenoxy]methyl}cyclopropyl)methyl]piperidin-1-yl}pyrimidine |
| 4-[((1S,2S)-2-{[1-(5-chloropyrimidin-2-yl)piperidin-4-yl]methyl}cyclopropyl)methoxy]benzenesulfonamide |
| rac-trans-6-[(2-{[1-(5-chloropyrimidin-2-yl)piperidin-4-yl] methyl} cyclopropyl) methoxy]-2-methylpyrimidine-4-carbonitrile |
| rac-trans-4-[(2-{[1-(5-chloropyrimidin-2-yl)piperidin-4-yl]methyl}cyclopropyl) methoxy]-6-methylpyrimidine-2-carbonitrile |
| rac-trans-4-[((1S,2S)-2-{[1-(5-chloropyrimidin-2-yl)piperidin-4-yl]methyl}cyclopropyl)methoxy]-3-fluorobenzonitrile |
| rac-cis-5-chloro-2-{4-[(2-{[4-(methylsulfonyl)phenoxy]methyl} cyclopropyl)methyl]piperidin-1-yl}pyrimidine |
| rac-cis 4-[(2-{[1-(5-chloropyrimidin-2-yl)piperidin-4-yl]methyl}cyclopropyl)methoxy]-N-cyclopropyl-2-fluorobenzamide |
| rac-cis-4-[(2-{[1-(5-chloropyrimidin-2-yl)piperidin-4-yl]methyl}cyclopropyl)methoxy]-6-methylpyrimidine-2-carbonitrile |
| rac-cis 4-[(2-{[1-(5-chloropyrimidin-2-yl)piperidin-4-yl]methyl}cyclopropyl)methoxy]-2-fluorobenzonitrile | as well as the pharmaceutically acceptable salts and solvates thereof.

A subset of compounds of the invention that is of interest relates to a compound of formula I-A:

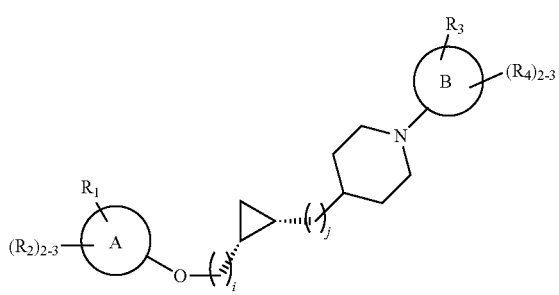

or a pharmaceutically acceptable salt or solvate thereof, wherein:

Ring A represents a 6-membered aryl or heteroaryl group containing 1 nitrogen atom, and optionally 1-2 additional nitrogen atoms;

Ring B represents a 6 membered heteroaryl ring containing 1-2 nitrogen atoms;

i and j independently represent integers selected from 0, 1 and 2, such that i plus j is 1 or 2;

$R^1$ represents a member selected from the group consisting of H, halo, $C_{1-6}$alkyl, halo$C_{1-6}$alkyl, C(O)$C_{1-6}$alkyl, C(O)halo$C_{1-6}$alkyl, C(O)NH—$C_{1-6}$alkyl, S(O)$C_{1-6}$alkyl, SO$_2$$C_{1-6}$alkyl, SO$_2$NH$_2$, SO$_2$NH$C_{1-6}$alkyl, SO$_2$N($C_{1-6}$alkyl)$_2$, CN, and HAR optionally substituted with 1-3 $C_{1-6}$alkyl, halo or halo $C_{1-6}$alkyl groups;

and each $R^2$, $R^3$ and $R^4$ is independently selected from H, halo, $C_{1-6}$alkyl and halo$C_{1-6}$alkyl.

Another aspect of the invention that is of interest relates to a compound of formula I-A, selected from the group consisting of TABLE 1-a rac cis-5-chloro-2-[4-(2-{2-[4-(methylsulfonyl)phenoxy]ethyl} cyclopropyl)piperidin-1-yl]pyrimidine, 5-chloro-2-[4-((1S,2R)-2-{2-[4-(methylsulfonyl)phenoxy]ethyl}cyclopropyl)piperidin-1-yl]pyrimidine and 5-chloro-2-[4-((1R,2S)-2-{2-[4-(methylsulfonyl)phenoxy]ethyl}cyclopropyl) piperidin-1-yl]pyrimidine
rac-cis 5-chloro-2-{4-[2-(2-{[5-(methylsulfonyl)pyridin-2-yl]oxy}ethyl)cyclopropyl] piperidin-1-yl}pyrimidine, 5-chloro-2-{4-[(1R,2S)-2-(2-{[5-(methylsulfonyl)pyridin-2-yl]oxy}ethyl)cyclopropyl]piperidin-1-yl}pyrimidine, 5-chloro-2-{4-[(1S,2R)-2-(2-{[5-(methylsulfonyl)pyridin-2-yl]oxy}ethyl)cyclopropyl]piperidin-1-yl}pyrimidine
rac cis-5-chloro-2-[4-(2-{2-[3-(methylsulfonyl)phenoxy]ethyl}cyclopropyl)piperidin-1-yl]pyrimidine
rac cis-5-chloro-2-[4-(2-{2-[3-(5-methyl-1,3,4-oxadiazol-2-yl)phenoxy]ethyl}cyclopropyl)piperidin-1-yl]pyrimidine
rac-cis-5-chloro-2-[4-(2-{2-[3-(1H-1,2,4-triazol-1-yl)phenoxy]ethyl}cyclopropyl)piperidin-1-yl]pyrimidine
rac cis-5-chloro-2-[4-(2-{2-[3-(1,3,4-oxadiazol-2-yl)phenoxy]ethyl}cyclopropyl)piperidin-1-yl]pyrimidine
rac cis-4-(2-{2-[1-(5-chloropyrimidin-2-yl)piperidin-4-yl]cyclopropyl}ethoxy)-N-cyclopropyl-2-fluorobenzamide
rac cis-4-(2-{2-[1-(5-chloropyrimidin-2-yl)piperidin-4-yl]cyclopropyl}ethoxy)-2-fluorobenzonitrile
rac cis-5-chloro-2-[4-(2-{2-[4-(cyclopropylsulfonyl)phenoxy]ethyl}cyclopropyl)piperidin-1-yl]pyrimidine
rac cis-5-chloro-2-[4-(2-{2-[3-fluoro-4-(5-methyl-1,3,4-oxadiazol-2-yl)phenoxy]ethyl}cyclopropyl)piperidin-1-yl]pyrimidine
rac cis-5-chloro-2-[4-(2-{2-[4-(1,3,4-oxadiazol-2-yl)phenoxy]ethyl}cyclopropyl)piperidin-1-yl]pyrimidine
rac cis-5-chloro-2-[4-(2-{2-[4-(5-methyl-1,3,4-oxadiazol-2-yl)phenoxy]ethyl}cyclopropyl)piperidin-1-yl]pyrimidine
rac cis-5-chloro-2-[4-(2-{2-[4-(1,2,4-oxadiazol-3-yl)phenoxy]ethyl}cyclopropyl)piperidin-1-yl]pyrimidine
rac cis-5-chloro-2-[4-(2-{2-[4-(1,2,4-oxadiazol-5-yl)phenoxy]ethyl}cyclopropyl)piperidin-1-yl]pyrimidine
rac cis-5-chloro-2-[4-(2-{2-[4-(1,3-oxazol-4-yl)phenoxy]ethyl}cyclopropyl)piperidin-1-yl]pyrimidine
rac cis-5-chloro-2-(4-{2-[2-(4-isoxazol-4-ylphenoxy)ethyl]cyclopropyl}piperidin-1-yl)pyrimidine
rac cis-5-chloro-2-(4-{2-[2-(4-isoxazol-5-ylphenoxy)ethyl]cyclopropyl}piperidin-1-yl)pyrimidine
rac cis-5-chloro-2-[4-(2-{2-[4-(1H-pyrazol-3-yl)phenoxy]ethyl}cyclopropyl)piperidin-1-yl]pyrimidine
rac cis-5-chloro-2-[4-(2-{2-[4-(1H-pyrazol-4-yl)phenoxy]ethyl}cyclopropyl)piperidin-1-yl]pyrimidine
rac cis-5-chloro-2-[4-(2-{2-[4-(1H-pyrazol-1-yl)phenoxy]ethyl}cyclopropyl)piperidin-1-yl]pyrimidine
rac cis-5-chloro-2-[4-(2-{2-[4-(1H-1,2,4-triazol-1-yl)phenoxy]ethyl}cyclopropyl)piperidin-1-yl]pyrimidine
rac cis-5-chloro-2-[4-(2-{2-[4-(4H-1,2,4-triazol-4-yl)phenoxy]ethyl}cyclopropyl)piperidin-1-yl]pyrimidine
rac cis-5-chloro-2-[4-(2-{2-[4-(1H-1,2,3-triazol-1-yl)phenoxy]ethyl}cyclopropyl)piperidin-1-yl]pyrimidine
rac-cis-5-fluoro-2-[4-(2-{2-[4-(1H-1,2,3-triazol-1-yl)phenoxy]ethyl}cyclopropyl)piperidin-1-yl]pyrimidine
rac cis-5-methyl-2-[4-(2-{2-[4-(1H-1,2,3-triazol-1-yl)phenoxy]ethyl}cyclopropyl)piperidin-1-yl]pyrimidine TABLE 1-a-continued rac cis-5-chloro-2-[4-(2-{2-[4-(2H-1,2,3-triazol-2-yl)phenoxy]ethyl}cyclopropyl)piperidin-1-yl]pyrimidine
rac cis-5-chloro-2-[4-(2-{2-[4-(1H-1,2,3-triazol-5-yl)phenoxy]ethyl}cyclopropyl)piperidin-1-yl]pyrimidine
rac cis-5-chloro-2-[4-(2-{2-[4-(1H-tetrazol-1-yl)phenoxy]ethyl}cyclopropyl)piperidin-1-yl]pyrimidine
rac cis-5-chloro-2-[4-(2-{2-[3-fluoro-4-(1H-tetrazol-1-yl)phenoxy]ethyl}cyclopropyl)piperidin-1-yl]pyrimidine
rac cis-5-fluoro-2-[4-(2-{2-[3-fluoro-4-(1H-tetrazol-1-yl)phenoxy]ethyl}cyclopropyl)piperidin-1-yl]pyrimidine
rac cis-2-[4-(2-{2-[3-fluoro-4-(1H-tetrazol-1-yl)phenoxy]ethyl}cyclopropyl)piperidin-1-yl]-5-methylpyrimidine
rac cis-5-chloro-2-[4-(2-{2-[4-(2H-tetrazol-2-yl)phenoxy]ethyl}cyclopropyl)piperidin-1-yl]pyrimidine
rac cis-5-chloro-2-[4-(2-{2-[4-(5-methyl-2H-tetrazol-2-yl)phenoxy]ethyl}cyclopropyl)piperidine-1-yl]pyrimidine
rac cis-5-chloro-2-[4-(2-{2-[4-(5-methyl-1H-tetrazol-1-yl)phenoxy]ethyl}cyclopropyl)piperidin-1-yl]pyrimidine
rac cis-5-chloro-2-[4-(2-{2-[3-fluoro-4-(5-methyl-1,3,4-oxadiazol-2-yl)phenoxy]ethyl}cyclopropyl)piperidin-1-yl]pyrimidine
5-chloro-2-[4-(1S,2R)-(2-{2-[4-(methylsulfinyl)phenoxy]ethyl}cyclopropyl)piperidin-1-yl]pyrimidine, 5-chloro-2-[4-(1R,2S)-(2-{2-[4-(methylsulfinyl)phenoxy]ethyl}cyclopropyl)piperidin-1-yl]pyrimidine
6-(1S,2R)-(2-{2-[1-(5-chloropyrimidin-2-yl)piperidin-4-yl]cyclopropyl}ethoxy)-2-methylpyrimidine-4-carbonitrile, 6-(1R,2S)-(2-{2-[1-(5-chloropyrimidin-2-yl)piperidin-4-yl]cyclopropyl}ethoxy)-2-methylpyrimidine-4-carbonitrile
Rac-cis-1-[4-(2-{2-[1-(5-chloropyrimidin-2-yl)piperidin-4-yl]cyclopropyl}ethoxy)phenyl]ethanone
Rac-cis-2-methyl-6-(2-{2-[1-(5-methylpyrazin-2-yl)piperidin-4-yl]cyclopropyl}ethoxy)pyrimidine-4-carbonitrile
Rac-cis-6-(2-{2-[1-(5-chloropyrimidin-2-yl)piperidin-4-yl]cyclopropyl}ethoxy)pyrimidine-4-carbonitrile
Rac-cis-4-(2-{2-[1-(5-chloropyrimidin-2-yl)piperidin-4-yl]cyclopropyl}ethoxy)pyrimidine-2-carbonitrile
2-methyl-6-(1S,2R)-(2-{2-[1-(5-methylpyrimidin-2-yl)piperidin-4-yl]cyclopropyl}ethoxy)pyrimidine-4-carbonitrile, 2-methyl-6-(1R,2S)-(2-{2-[1-(5-methylpyrimidin-2-yl)piperidin-4-yl]cyclopropyl}ethoxy)pyrimidine-4-carbonitrile
Rac-cis-2-methyl-6-(2-{2-[1-(5-methylpyrimidin-2-yl)piperidin-4-yl]cyclopropyl}ethoxy)pyrimidine-4-carbonitrile
Rac-cis-2,4-dimethyl-6-(2-{2-[1-(5-methylpyrimidin-2-yl)piperidin-4-yl]cyclopropyl}ethoxy)pyrimidine
Rac-cis-6-(2-{2-[1-(5-chloro-4-methylpyrimidin-2-yl)piperidin-4-yl]cyclopropyl}ethoxy)-2-methylpyrimidine-4-carbonitrile
Rac-cis-6-(2-{2-[1-(5-chloropyridin-2-yl)piperidin-4-yl]cyclopropyl}ethoxy)-2-methylpyrimidine-4-carbonitrile
Rac-cis-6-(2-{2-[1-(4,5-dimethylpyrimidin-2-yl)piperidin-4-yl]cyclopropyl}ethoxy)-2-methylpyrimidine-4-carbonitrile
Rac-cis-6-(2-{2-[1-(5-chloro-4-methylpyridin-2-yl)piperidin-4-yl]cyclopropyl}ethoxy)-2-methylpyrimidine-4-carbonitrile
Rac-cis-6-(2-{2-[1-(5-fluoro-4-methylpyridin-2-yl)piperidin-4-yl]cyclopropyl}ethoxy)-2-methylpyrimidine-4-carbonitrile
Rac-cis-2-methyl-6-[2-(2-{1-[5-(trifluoromethyl)pyridin-2-yl]piperidin-4-yl}cyclopropyl)ethoxy]pyrimidine-4-carbonitrile
Rac-cis-5-chloro-2-(4-{2-[2-(pyridine-3-yloxy)ethyl]cyclopropyl}piperidin-1-yl)pyrimidine
Rac-cis-5-chloro-2-(4-{2-[2-(pyrimidin-4-yloxy)ethyl]cyclopropyl}piperidin-1-yl)pyrimidine
Rac-cis-5-(2-{2-[1-(5-chloropyrimidin-2-yl)piperidin-4-yl]cyclopropyl}ethoxy)nicotinonitrile
Rac-cis-6-(2-{2-[1-(5-chloropyrimidin-2-yl)piperidin-4-yl]cyclopropyl}ethoxy)-2-methylpyrimidine-4-carbonitrile
Rac-cis-4-(2-{2-[1-(5-chloropyrimidin-2-yl)piperidin-4-yl]cyclopropyl}ethoxy)-6-methylpyrimidine-2-carbonitrile
Rac-cis-6-(2-{2-[1-(5-fluoropyrimidin-2-yl)piperidin-4-yl]cyclopropyl}ethoxy)-2-methylpyrimidine-4-carbonitrile
Rac-cis-5-(2-{2-[1-(5-chloropyrimidin-2-yl)piperidin-4-yl]cyclopropyl}ethoxy)pyridine-2-carbonitrile
Rac-cis-5-chloro-2-(4-{2-[2-(pyridine-4-yloxy)ethyl]cyclopropyl}piperidin-1-yl)pyrimidine
5-chloro-2-(1S,2R)-{4-[2-(2-{[5-(1H-1,2,3-triazol-1-yl)pyridin-2-yl]oxy}ethyl)cyclopropyl]piperidin-1-yl}pyrimidine, 5-chloro-2-(1R,2S)-{4-[2-(2-{[5-(1H-1,2,3-triazol-1-yl)pyridin-2-yl]oxy}ethyl)cyclopropyl]piperidin-1-yl}pyrimidine
5-chloro-2-[4-((1R,2S)-2-{2-[3-fluoro-4-(5-methyl-1,3,4-oxadiazol-2-yl)phenoxy]ethyl}cyclopropyl)piperidin-1-yl]pyrimidine and 5-chloro-2-[4-((1S,2R)-2-{2-[3-fluoro-4-(5-methyl-1,3,4-oxadiazol-2-yl)phenoxy]ethyl}cyclopropyl)piperidin-1-yl]pyrimidine
rac cis-5-chloro-2-[4-(2-{2-[4-(1H-1,2,3-triazol-1-yl)phenoxy]ethyl}cyclopropyl)piperidin-1-yl]pyrimidine, 5-chloro-2-[4-((1S,2R)-2-{2-[4-(1H-1,2,3-triazol-1-yl)phenoxy]ethyl}cyclopropyl)piperidin-1-yl]pyrimidine and 5-chloro-2-[4-((1R,2S)-2-{2-[4-(1H-1,2,3-triazol-1-yl)phenoxy]ethyl}cyclopropyl)piperidin-1-yl]pyrimidine
5-fluoro-2-[4-((1R,2S)-2-{2-[4-(1H-1,2,3-triazol-1-yl)phenoxy]ethyl}cyclopropyl)piperidin-1-yl]pyrimidine and 5-fluoro-2-[4-((1S,2R)-2-{2-[4-(1H-1,2,3-triazol-1-yl)phenoxy]ethyl}cyclopropyl)piperidin-1-yl]pyrimidine
5-chloro-2-[4-((1R,2S)-2-{2-[4-(1H-tetrazol-1-yl)phenoxy]ethyl}cyclopropyl)piperidin-1-yl]pyrimidine and 5-chloro-2-[4-((1S,2R)-2-{2-[4-(1H-tetrazol-1-

TABLE 1-a-continued yl)phenoxy]ethyl}cyclopropyl)piperidin-1-yl]pyrimidine
5-chloro-2-[4-((1R,2S)-2-{2-[3-fluoro-4-(1H-tetrazol-1-yl)phenoxy]ethyl}cyclopropyl)piperidin-1-yl]pyrimidine and 5-chloro-2-[4-((1S,2R)-2-{2-[3-fluoro-4-(1H-tetrazol-1-yl)phenoxy]ethyl}cyclopropyl)piperidin-1-yl]pyrimidine
5-fluoro-2-[4-((1R,2S)-2-{2-[3-fluoro-4-(5-methyl-1,3,4-oxadiazol-2-yl)phenoxy]ethyl}cyclopropyl)piperidin-1-yl]pyrimidine and 5-fluoro-2-[4-((1S,2R)-2-{2-[3-fluoro-4-(5-methyl-1,3,4-oxadiazol-2-yl)phenoxy]ethyl}cyclopropyl)piperidin-1-yl]pyrimidine
rac-cis-2-[4-(2-{2-[3-fluoro-4-(5-methyl-1,3,4-oxadiazol-2-yl)phenoxy]ethyl}cyclopropyl)piperidin-1-yl]-5-methylpyrimidine
Rac-cis-2-[4-(2-{2-[3-fluoro-4-(5-methyl-1,3,4-oxadiazol-2-yl)phenoxy]ethyl}cyclopropyl)piperidin-1-yl]pyrimidine
Rac-cis-5-fluoro-2-[4-(2-{2-[3-fluoro-4-(5-methyl-1,3,4-oxadiazol-2-yl)phenoxy]ethyl}cyclopropyl)piperidin-1-yl]pyrimidine
Rac-cis-5-chloro-2-[4-(2-{2-[3-fluoro-4-(5-methyl-1,3,4-oxadiazol-2-yl)phenoxy]ethyl}cyclopropyl)piperidin-1-yl]-4-methylpyrimidine
Rac-cis-3,5-dichloro-2-[4-(2-{2-[3-fluoro-4-(5-methyl-1,3,4-oxadiazol-2-yl)phenoxy]ethyl}cyclopropyl)piperidin-1-yl]pyridine
Rac-cis-2-[4-(2-{2-[3-fluoro-4-(5-methyl-1,3,4-oxadiazol-2-yl)phenoxy]ethyl}cyclopropyl)piperidin-1-yl]-5-(trifluoromethyl)pyridinium trifluoroacetate
rac-cis-5-chloro-2-{4-[(2-{[4-(methylsulfonyl)phenoxy]methyl} cyclopropyl)methyl]piperidin-1-yl}pyrimidine
rac-cis 4-[(2-{[1-(5-chloropyrimidin-2-yl)piperidin-4-yl]methyl}cyclopropyl)methoxy]-N-cyclopropyl-2-fluorobenzamide
rac-cis-4-[(2-{[1-(5-chloropyrimidin-2-yl)piperidin-4-yl]methyl}cyclopropyl)methoxy]-6-methylpyrimidine-2-carbonitrile
rac-cis 4-[(2-{[1-(5-chloropyrimidin-2-yl)piperidin-4-yl]methyl}cyclopropyl)methoxy]-2-fluorobenzonitrile.

as well as the pharmaceutically acceptable salt and solvates thereof.

Utilities

Compounds of the present invention are potent agonists of the GPR119 receptor. The compounds of the invention, and pharmaceutically acceptable salts thereof are modulators of the receptor known as GPR 119, and are therefore useful in the treatment of diseases that are modulated by GPR119 ligands and agonists. Many of these diseases are summarized below.

Treatment and prevention of the following diseases and conditions are included in the manufacture of a medicament for treating one or more of these diseases or conditions:
  (1) non-insulin dependent diabetes mellitus (type 2 diabetes);
  (2) hyperglycemia;
  (3) the metabolic syndrome;
  (4) obesity;
  (5) ischemia and myocardial infarction;
  (6) neurological disorders such as alzheimer's disease, schizophrenia, and impaired cognition;
  (5) hypercholesterolemia;
  (6) hypertriglyceridemia (elevated levels of triglyceride-rich-lipoproteins);
  (7) mixed or diabetic dyslipidemia;
  (8) low HDL cholesterol;
  (9) high LDL cholesterol;
  (10) hyper apo β liproteinemia; and
  (11) atherosclerosis.

More particularly, the following diseases and conditions can be treated using the compounds of formula I or Ia, or a pharmaceutically acceptable salt or solvate thereof. The compounds are used for manufacturing a medicament for the treatment or prevention of one or more of these diseases or conditions:
  (1) Type 2 diabetes, and specifically hyperglycemia;
  (2) Metabolic syndrome;
  (3) Obesity; and
  (4) Hypercholesterolemia or dyslipidemias.

Because the compounds are agonists of the GPR119 receptor, the compounds are useful for lowering glucose, lipids, and insulin resistance in diabetic patients and in non-diabetic patients who have impaired glucose tolerance and/or are in a pre-diabetic condition. The compounds are useful to ameliorate hyperinsulinemia, which often occurs in diabetic or pre-diabetic patients, by modulating the swings in the level of serum glucose that often occurs in these patients. The compounds are useful for treating or reducing insulin resistance. The compounds are useful for treating or preventing gestational diabetes.

The compounds, compositions, and medicaments as described herein are useful for reducing the risks of adverse sequelae associated with metabolic syndrome, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

By keeping hyperglycemia under control, the compounds are useful to delay or for preventing vascular restenosis and diabetic retinopathy.

The compounds of this invention are useful in improving or restoring β-cell function, so that they are useful in treating type 1 diabetes or in delaying or preventing a patient with type 2 diabetes from needing insulin therapy.

The compounds may be useful for reducing appetite and body weight in obese subjects and may therefore be useful in reducing the risk of co-morbidities associated with obesity such as hypertension, atherosclerosis, diabetes, and dyslipidemia.

By elevating levels of active GLP-1 in vivo, the compounds are useful in treating neurological disorders such as Alzheimer's disease, multiple sclerosis, and schizophrenia.

The compounds generally are useful for treating the following diseases and conditions: (1) type 2 diabetes (also known as non-insulin dependent diabetes mellitus, or T2DM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) abdominal obesity, (16) retinopathy, (17)

metabolic syndrome, (18) high blood pressure, (19) Alzheimer's disease, (20) schizophrenia, (21) multiple sclerosis, and (22) insulin resistance.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound of formula I or a pharmaceutically acceptable salt or solvate thereof. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example torcetrapib), niacin, bile acid sequestrants, microsomal triglyceride transport inhibitors, and bile acid reuptake inhibitors. These combination treatments are useful for the treatment or control of conditions selected from the group consisting of hypercholesterolemia, atherosclerosis, hyperlipidemia, hypertriglyceridemia, dyslipidemia, high LDL and low HDL.

Another aspect of the invention provides a method for the treatment and control of obesity or metabolic syndrome, which comprises administering to a patient in need of such treatment a therapeutically effective amount of a compound having formula I or a pharmaceutically acceptable salt or solvate thereof. The compound may be used alone or advantageously may be administered with an anti-obesity agent, particularly a lipase inhibitor such as orlistat, or a monoamine neurotransmitter uptake inhibitor such as sibutramine, phentermine and the like. The compound may also be used advantageously in combination with CB-1 inverse agonists or antagonists such as rimonabant and taranabant.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I or a pharmaceutically acceptable salt or solvate thereof are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 350 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets or capsules. Examples of doses in tablets and capsules are 0.1 mg, 0.25 mg, 0.5 mg, 1 mg, 2 mg, 5 mg, 10 mg, 25 mg, 50 mg, 100 mg, 200 mg, 350 mg, 500 mg, 700 mg, 750 mg, 800 mg and 1000 mg. Other oral forms may also have the same or similar dosages.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt or solvate as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

The compositions are typically suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the condition being treated and on the particular active ingredient selected. They may be conveniently presented in unit dosage form and prepared by any of the methods well-known in the art of pharmacy.

In practical use, the compound of Formula I, or the pharmaceutically acceptable salt or solvate thereof can be combined as the active ingredient in intimate admixture with the pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage form. Solid pharmaceutical carriers are therefore typically employed. If desired, tablets may be coated by standard aqueous or nonaqueous techniques. Such compositions and preparations typically comprise at least about 0.1 percent of active compound, the remainder of the composition being the carrier. The percentage of active compound in these compositions may, of course, be varied and is conveniently between about 2 percent to about 60 percent of the weight of the dosage form. The amount of active compound in such therapeutically useful compositions is such that an effective dosage will be delivered.

Alternatively, the active compound can be administered intranasally as, for example, in the form of liquid drops or a spray.

The tablets, capsules and the like also typically contain a binder. Examples of suitable binders include gum tragacanth, acacia, gelatin and a synthetic or semisynthetic starch derivative, such as hydroxypropylmethylcellulose (HPMC); excipients such as dicalcium phosphate; a disintegrating agent such as corn starch, potato starch, alginic acid; a lubricant such as magnesium stearate; and in some instances, a sweetening agent such as sucrose, lactose or saccharin. When the dosage form employed is a capsule, it may contain, in addition to the components described above, a liquid carrier such as a fatty oil.

Various other materials may be present as coatings or to modify the physical form of the dosage unit. For instance, tablets may be coated with shellac, sugar or both. Syrups and elixirs typically contain, in addition to the active ingredient, sucrose as a sweetening agent, methyl or propylparabens as a preservative, a dye and a flavoring such as cherry or orange flavor.

The compound of formula I or a pharmaceutically acceptable salt or solvate thereof may also be administered parenterally. Solutions or suspensions of these active compounds can be prepared in water, saline or another biocompatible vehicle, suitably mixed with a surfactant, buffer, and the like. Dispersions can also be prepared in glycerol, liquid polyethylene glycols and mixtures thereof in an oil. Under ordinary conditions of storage and use, these preparations can also contain a preservative to prevent the growth of microorganisms.

The pharmaceutical forms suitable for injectable use include sterile aqueous solutions and dispersions, and sterile powders for the extemporaneous preparation of sterile injectable solutions and dispersions. The preparation should be prepared under sterile conditions and be fluid to the extent that easy syringability exists. It should be sufficiently stable under the conditions of manufacture and storage and preserved against the growth of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and suitable oils.

Combination Therapy

Compounds of Formula I may be used in combination with other drugs that may also be useful in the treatment or amelioration of the diseases and conditions described herein. Such other drugs may be administered, by a route and in an amount commonly used therefor, contemporaneously or sequentially with a compound of Formula I or a pharmaceutically acceptable salt or solvate thereof. In the treatment of patients who have type 2 diabetes, insulin resistance, obesity, metabolic syndrome, neurological disorders, and co-morbidities that accompany these diseases, more than one drug is commonly administered. The compounds of this invention may generally be administered to a patient who is already taking one or more other drugs for these conditions.

When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, and LY-818;

(b) biguanides such as metformin and phenformin;

(c) protein tyrosine phosphatase-1B (PTP-1B) inhibitors;

(d) dipeptidyl peptidase IV (DPP-4) inhibitors, such as sitagliptin, saxagliptin, denagliptin, SYR-322, alogliptin and vildagliptin;

(e) insulin or insulin mimetics;

(f) sulfonylureas such as tolbutamide, glimepiride, glipizide, and related materials;

(g) α-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) cholesterol absorption inhibitors, such as for example ezetimibe, (vi) acyl CoA:cholesterol acyltransferase (ACAT) inhibitors, such as avasimibe, (vii) CETP inhibitors, such as torcetrapib, and (viii) phenolic anti-oxidants, such as probucol;

(i) PPARα/γ dual agonists, such as muraglitazar, tesaglitazar, farglitazar, and JT-501;

(j) PPARδ agonists such as those disclosed in WO97/28149;

(k) antiobesity compounds such as fenfluramine, dexfenfluramine, phentiramine, subitramine, orlistat, neuropeptide Y5 inhibitors, MC4R agonists, cannabinoid receptor 1 (CB-1) antagonists/inverse agonists, and $β_3$ adrenergic receptor agonists;

(l) ileal bile acid transporter inhibitors;

(m) agents intended for use in inflammatory conditions such as aspirin, non-steroidal anti-inflammatory drugs, glucocorticoids, azulfidine, and cyclo-oxygenase 2 selective inhibitors;

(n) glucagon receptor antagonists;

(o) GLP-1, (p) GIP-1, (q) GLP-1 analogs, such as exendins, for example exenatide (Byetta), exenatide-LAR, and liraglutide (r) Hydroxysterol dehydrogenase-1 (HSD-1) inhibitors.

The above combinations include combinations of a compound of the present invention not only with one other active compound, but also with two or more other active compounds. Non-limiting examples include combinations of compounds having Formula I or a pharmaceutically acceptable salt or solvate thereof with two or more active compounds selected from biguanides, sulfonylureas, HMG-CoA reductase inhibitors, other PPAR agonists, PIP-1B inhibitors, DPP-4 inhibitors, and anti-obesity compounds.

Another aspect of the invention that is of interest is a pharmaceutical composition comprised of a compound of formula I or a pharmaceutically acceptable salt or solvate thereof in combination with a pharmaceutically acceptable carrier.

Another aspect of the invention that is of interest relates to a method of treating hyperglycemia, diabetes or insulin resistance in a mammalian patient in need of such treatment which comprises administering to said patient a compound in accordance with formula I or a pharmaceutically acceptable salt or solvate thereof in an amount that is effective to treated hyperglycemia, diabetes or insulin resistance.

More particularly, another aspect of the invention that is of interest relates to a method of treating type 2 diabetes in a mammalian patient in need of such treatment comprising administering to the patient a compound in accordance with formula I or a pharmaceutically acceptable salt or solvate thereof in an amount that is effective to treat type 2 diabetes.

Yet another aspect of the invention that is of interest relates to a method of treating non-insulin dependent diabetes mellitus in a mammalian patient in need of such treatment comprising administering to the patient a compound in accordance with formula I or a pharmaceutically acceptable salt or solvate thereof in an amount that is effective to treat non-insulin dependent diabetes mellitus.

Yet another aspect of the invention that is of interest relates to a method of treating obesity in a mammalian patient in need of such treatment comprising administering to said patient a compound in accordance with formula I or a pharmaceutically acceptable salt or solvate thereof in an amount that is effective to treat obesity.

Yet another aspect of the invention that is of interest relates to a method of treating Syndrome X in a mammalian patient in need of such treatment, comprising administering to said patient a compound in accordance with formula I or a pharmaceutically acceptable salt or solvate thereof in an amount that is effective to treat Syndrome X.

Yet another aspect of the invention that is of interest relates to a method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound in accordance with formula I or a pharmaceutically acceptable salt or solvate thereof in an amount that is effective to treat said lipid disorder.

Yet another aspect of the invention that is of interest relates to a method of treating atherosclerosis in a mammalian patient in need of such treatment, comprising administering to said patient a compound in accordance with a compound in accordance with formula I or a pharmaceutically acceptable salt or solvate thereof in an amount that is effective to treat atherosclerosis.

Yet another aspect of the invention that is of interest relates to a method of treating a condition selected from the group consisting of: (1) hyperglycemia, (2) impaired glucosetolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient a compound in accordance with formula I or a pharmaceutically acceptable salt or solvate thereof in an amount that is effective to treat said condition.

Yet another aspect of the invention that is of interest relates to a method of delaying the onset of a condition selected from the group consisting of (1) hyperglycemia, (2) impaired glucosetolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component in a mammalian patient in need thereof, comprising administering to the patient a compound in accordance with formula I or a pharmaceutically acceptable salt or solvate thereof in an amount that is effective to delay the onset of said condition.

Yet another aspect of the invention that is of interest relates to a method of reducing the risk of developing a condition selected from the group consisting of (1) hyperglycemia, (2) impaired glucosetolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component in a mammalian patient in need thereof, comprising administering to the patient a compound in accordance with formula I or a pharmaceutically acceptable salt or solvate thereof in an amount that is effective to reduce the risk of developing said condition.

Yet another aspect of the invention that is of interest relates to a method of treating a condition selected from the group consisting of (1) hyperglycemia, (2) impaired glucosetolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient a compound in accordance with formula I or a pharmaceutically acceptable salt or solvate thereof in an amount that is effective to treat said condition, and a compound selected from the group consisting of:
  (a) DP-TV inhibitors;
  (b) insulin sensitizers selected from the group consisting of (i) PPAR agonists and (ii) biguanides;
  (c) insulin and insulin mimetics;
  (d) sulfonylureas and other insulin secretagogues;
  (e) α-glucosidase inhibitors;
  (f) glucagon receptor antagonists;
  (g) GLP-1, GLP-1 mimetics, and GLP-1 receptor agonists;
  (h) GIP, GIP mimetics, and GIP receptor agonists;
  (i) PACAP, PACAP mimetics, and PACAP receptor δ agonists;
  (j) cholesterol lowering agents selected from the group consisting of (i) HMG-CoA reductase inhibitors, (ii) sequestrants, (iii) nicotinyl alcohol, nicotinic acid and salts thereof, (iv) PPARα agonists, (v) PPARα/γ dual agonists, (vi) inhibitors of cholesterol absorption, (vii) acyl CoA:cholesterol acyltransferase inhibitors, and (viii) anti-oxidants;
  (k) PPARδ agonists;
  (l) antiobesity compounds;

(m) ileal bile acid transporter inhibitors;

(n) anti-inflammatory agents excluding glucocorticoids;

(o) protein tyrosine phosphatase-1B (PTP-1B) inhibitors; and (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; said compounds being administered to the patient in an amount that is effective to treat said condition.

Yet another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient a compound in accordance with formula I or a pharmaceutically acceptable salt or solvate thereof and an HMG-CoA reductase inhibitor, in amounts that are effective to treat said condition.

More particularly, another aspect of the invention that is of interest relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient a compound in accordance with formula I or a pharmaceutically acceptable salt or solvate thereof and an HMG-CoA reductase inhibitor in the form of a statin, said compounds being administered in amounts that are effective for treating said condition. Statins useful in this regard include the group consisting of lovastatin, simvastatin, pravastatin, fluvastatin, atorvastatin, itavastatin, ZD-4522 and rivastatin.

A method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions comprising administering to a mammalian patient in need of such treatment a therapeutically effective amount of a compound as defined in claim 1 and an HMG-CoA reductase inhibitor.

More particularly, another aspect of the invention that is of interest relates to a method of delaying the onset or reducing the risk of developing atherosclerosis in a human patient in need of such treatment comprising administering to the patient a compound in accordance with formula I or a pharmaceutically acceptable salt or solvate thereof and an HMG-CoA reductase inhibitor in the form of a statin, said compounds being administered in amounts that are effective for treating said condition. Statins useful in this regard include the group consisting of lovastatin, simvastatin, pravastatin, fluvastatin, atorvastatin, itavastatin, ZD-4522 and rivastatin.

More particularly, another aspect of the invention that is of interest relates to a method of treating, delaying the onset or reducing the risk of developing atherosclerosis in a human patient in need of such treatment comprising administering to the patient a compound in accordance with formula I or a pharmaceutically acceptable salt or solvate thereof and a cholesterol absorption inhibitor, said compounds being administered in amounts that treat, delay the onset, or reduce the risk of developing atherosclerosis.

Even more particularly, another aspect of the invention that is of interest relates to a method of treating, delaying the onset or reducing the risk of developing atherosclerosis in a human patient in need of such treatment comprising administering to the patient a compound in accordance with formula I or a pharmaceutically acceptable salt or solvate thereof and a cholesterol absorption inhibitor, wherein the cholesterol absorption inhibitor is ezetimibe, said compounds being administered in amounts that treat, delay the onset, or reduce the risk of developing atherosclerosis.

Yet another aspect of the invention that is of interest relates to a pharmaceutical composition that is comprised of: (1) a compound according to formula I or a pharmaceutically acceptable salt or solvate thereof, (2) a compound selected from the group consisting of:

(a) DP-IV inhibitors;

(b) insulin sensitizers selected from the group consisting of (i) PPAR agonists and (ii) biguanides;

(c) insulin and insulin mimetics;

(d) sulfonylureas and other insulin secretagogues;

(e) α-glucosidase inhibitors;

(f) glucagon receptor antagonists;

(g) GLP-1, GLP-1 mimetics, and GLP-1 receptor agonists;

(h) GIP, GIP mimetics, and GIP receptor agonists;

(i) PACAP, PACAP mimetics, and PACAP receptor δ agonists;

(j) cholesterol lowering agents selected from the group consisting of (i) HMG-CoA reductase inhibitors, (ii) sequestrants, (iii) nicotinyl alcohol, nicotinic acid or a salt thereof, (iv) PPARα agonists, (v) PPARα/γdual agonists, (vi) inhibitors of cholesterol absorption, (vii) acyl CoA:cholesterol acyltransferase inhibitors, and (viii) anti-oxidants;

(k) PPARδ agonists;

(l) antiobesity compounds;

(m) ileal bile acid transporter inhibitors;

(n) anti-inflammatory agents other than glucocorticoids;

(o) protein tyrosine phosphatase-1B (PTP-1B) inhibitors; and (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; and (3) a pharmaceutically acceptable carrier Another aspect of the invention that is of interest relates to the use of a compound in accordance with formula I or a pharmaceutically acceptable salt or solvate thereof in the manufacture of a medicament for use in treating a disease or condition described herein.

The compounds of the invention can be prepared using the synthetic schemes described herein as well as any of several alternate methods which will be apparent to a chemist skilled in the art. The following abbreviations may be used in the synthetic schemes or Examples:

Ac is acetyl [$CH_3C(O)$—]; $Ac_2O$ is acetic anhydride; AcAc is acetyl acetonate; Ar is Aryl; ArX is an aryl halide; 9-BBN is 9-borabicyclo[3.3.1]nonane; Bn is benzyl; BOC is tert Butyloxycarbonyl; BuTMDOB is trans 2-butyl-N,N,N',N'-tetramethyl-1,3,2-dioxaborolane-4,5-dicarboxamide, as specified R,R or S,S; DBU is diazabicycloundecane; DBAD is di-tert-butylazodicarboxylate; DIAD is diisopropylazodicarboxylate; DIBAL or DiBAl-His diisobutylaluminum hydride; DMA is dimethylacetamide; DMF is N,N-dimethylformamide; DMSO is dimethyl sulfoxide; EDAC (or EDC) is 1-ethyl-3-[3-(dimethylamino)propyl]-carbodiimide HCl; $Et_3N$ is triethylamine; Et is ethyl; EtOAc is ethyl acetate; EtOH is ethanol; HCl is hydrochloric acid; Het-X is heterocyclic halide; HOBt is 1-hydroxybenzotriazole; HPLC is high performance liquid chromatography; iPrOAc is isopropyl acetate; LG is leaving group; M is molar; mmol is millimole; Me is methyl; MeOH is methanol; MsCl methanesulfonyl chloride; N is normal; NaHMDS is sodium hexamethyldisiliazide; NaOAc is sodium acetate; NaOtBu is sodium tert-butoxide; NMO is N-methylmorpholine N oxide; NMP is N-methylpyrrolidinone; Pd(dba)$_2$ is tris(dibenzylideneacetone)dipalladium; PdCl$_2$(Ph$_3$P)$_2$ is dichlorobis-(triphenylphosphene) palladium; PG Denotes an unspecified protecting group; Ph is phenyl; PhMe is toluene; PPh$_3$ is triphenylphosphine; PMB is para-methoxybenzyl; RT is room temperature; TBAF is tetrabutyl ammonium fluoride; TBS is tert-butyldimethylsilyl; tBu is tert-butyl; Tf is triflate; TFA is trifluoroacetic acid; THE is tetrahydrofuran; TLC is thin layer chromatography; TMEDA is tetramethylethylenediamine; TMS is trimethylsilyl; TPAP is tetrapropylammonium perruthenate.

General Schemes

Substituted aryl and heteroaryl coupling intermediates shown in the schemes are commercially available or may be prepared from readily accessible aryl, heterocyclic, or other congeners via a host of routes. Many intermediates are accessible through either modification of a pre-formed heteroaryl scaffold or through de novo ring synthesis.

The substituted alkyl piperidines of this invention can be prepared by any of several methods. The specific examples detailed below may employ some of the following general procedures. Many functionalized piperidines are commercially available. Where they are not, one of the most useful synthetic routes for their preparation utilizes a reduction of a suitable pyridine. Low pressure reductions with hydrogen and 5-10% Pd on charcoal or similar hydrogenation catalyst in acetic acid- or stepwise reduction of an activated pyridinium acyl by hydride followed by similar hydrogenation will lead to the appropriate piperidine. The sidechain may be present in its desired final configuration, or it may be elaborated by well known methods after the piperidine ring is generated. (Scheme 1)

SCHEME 1

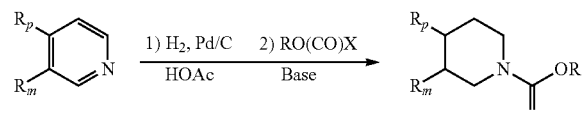

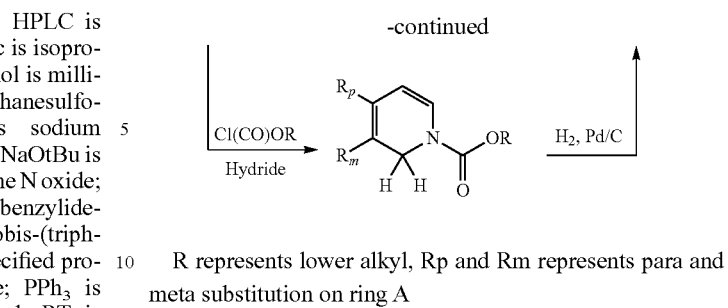

R represents lower alkyl, Rp and Rm represents para and meta substitution on ring A The cyclopropyl residue in the connecting chain of the present examples may be introduced by any of several methods. A particularly convenient method is outlined in Scheme 2 below. Conversion of the readily available hydroxymethyl piperidine to the acetylene by a multistep protocol allows ready access to the indicated cis olefins after Lindlar reduction. (See for example; Eymery, et al, *Synth* 2000, 185-213. Page 196 for a convenient protocol.) Homologation of the same intermediate through the Horner-Emmons modification of the Wittig reaction allows easy access to the trans olefins. Charette's Et$_2$Zn/CH$_2$I$_2$ cyclopropanation affords racemic, diasteromerically enriched or enantiomerically enriched cyclopropyl analogs. (Charette et al, *JAGS* 1998, 120, 11943-11952; further details in Charette, et al, *JAGS,* 2001, 123, 12160-12167.) In the absence of an auxiliary chiral Lewis acid the cis allylic olefin affords good yields of the desired racemic analog. Also in the absence of an auxiliary chiral Lewis acid, the chiral alcohol derived from the opening of R or S glycidyl epoxide affords reasonable ratios the chiral diasteromerie cyclopropanation products.

With the addition of the auxiliary chiral Lewis acid RR or SS trans-2-butyl-N,N,N',N'-tetramethyl-1,3,2-dioxaborolane-4,5-dicarboxamide (BuTMDOB), the same cyclopropanation protocol leads to very good ratios of the desired enantiomer in either the allylic or homoallylic cyclopropanation. The depicted chiral homoallylic alcohol requires the "matched" dioxaborolane in the double diasteroselection protocol.

SCHEME 2

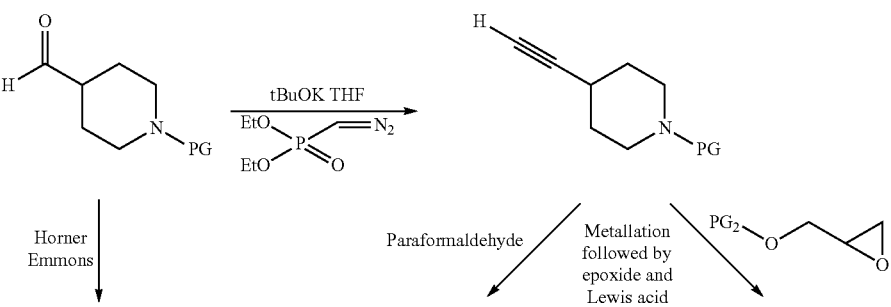

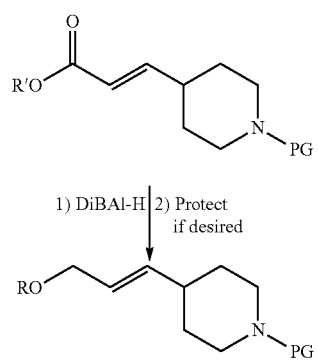
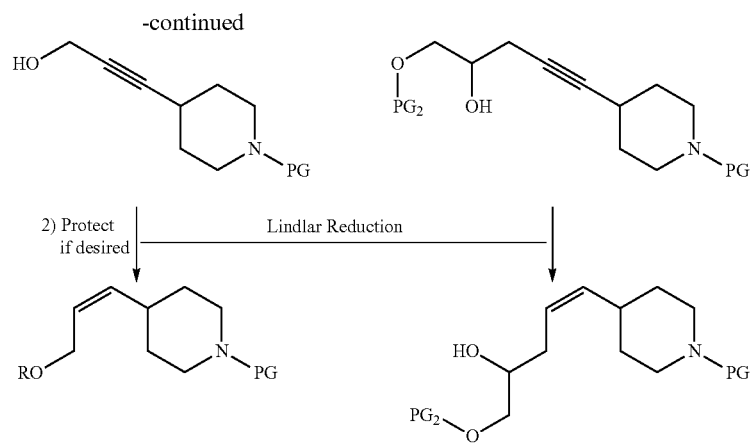
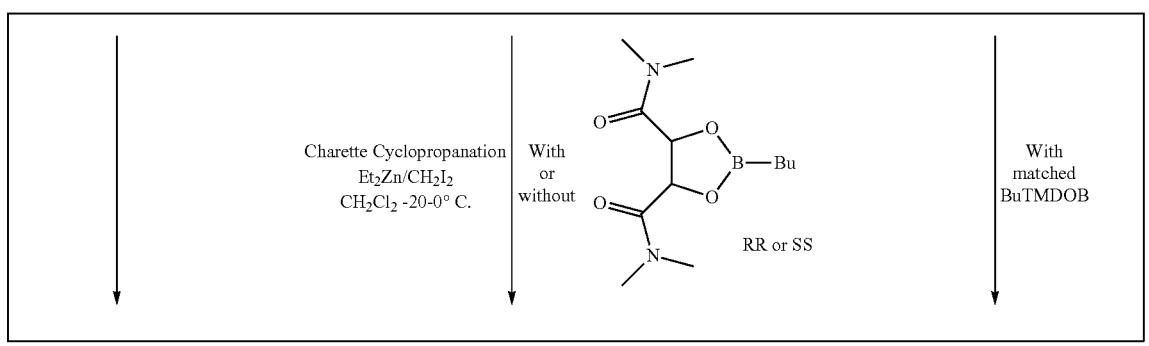
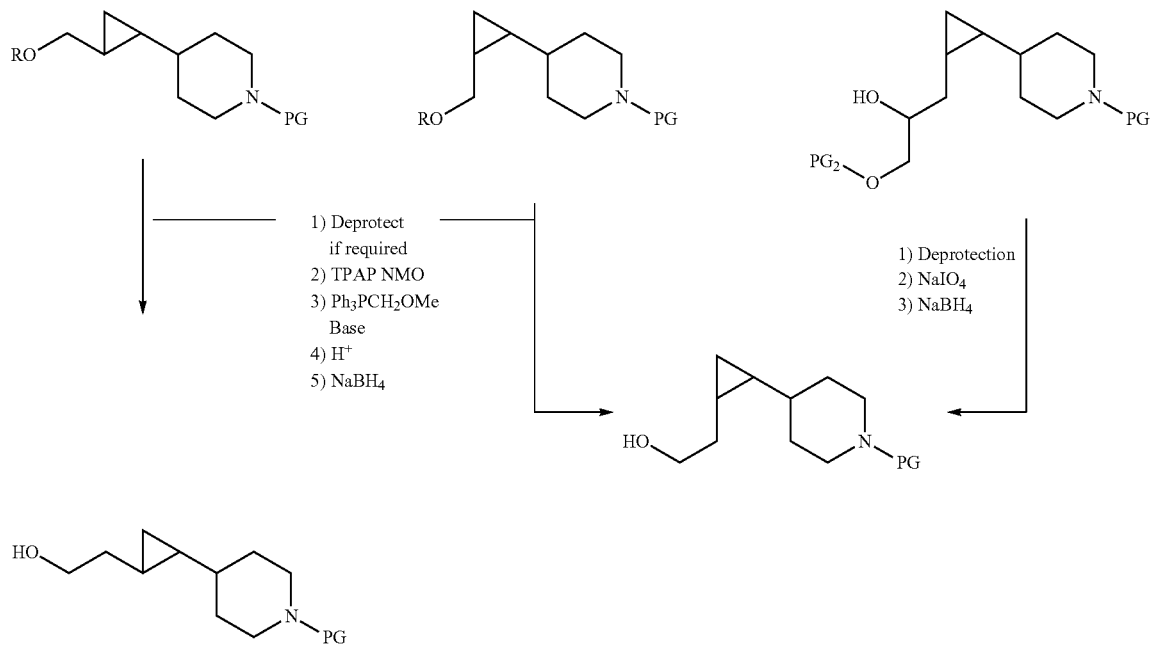

R' represents lower alkyl, R represents H or PG$_2$. PG$_2$ is a protecting group, preferably benzyl Introduction of the piperidine nitrogen substituent can be accomplished by a particularly wide variety of routes. Some of the most versatile routes for the examples reported here are represented in scheme 3. Direct displacement of labile heteroaryl halides or similar leaving groups can often be used to introduce the nitrogen substituent directly. Subsequent functionalization of the aryl ether is similarly straightforward. Mitsunobu coupling, activation of the primary alcohol followed by displacement or direct displacement on heteroaryl systems are all well known to the practicing synthetic chemist.

SCHEME 3

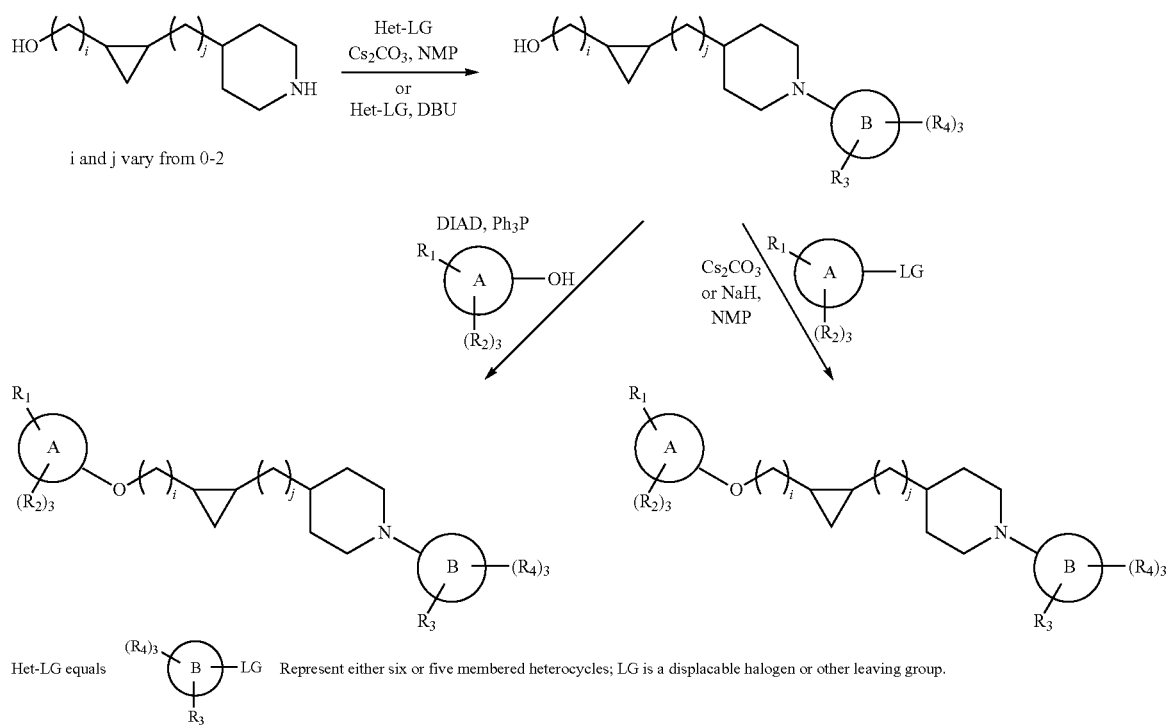

The order of introduction of aryl ether and piperidine N substituents is easily inverted by use of Nitrogen protecting groups such as BOC, FMOC, CBZ or other readily removed PG. Removal of the nitrogen protecting group generates a coupling partner for further elaboration.

SCHEME 4

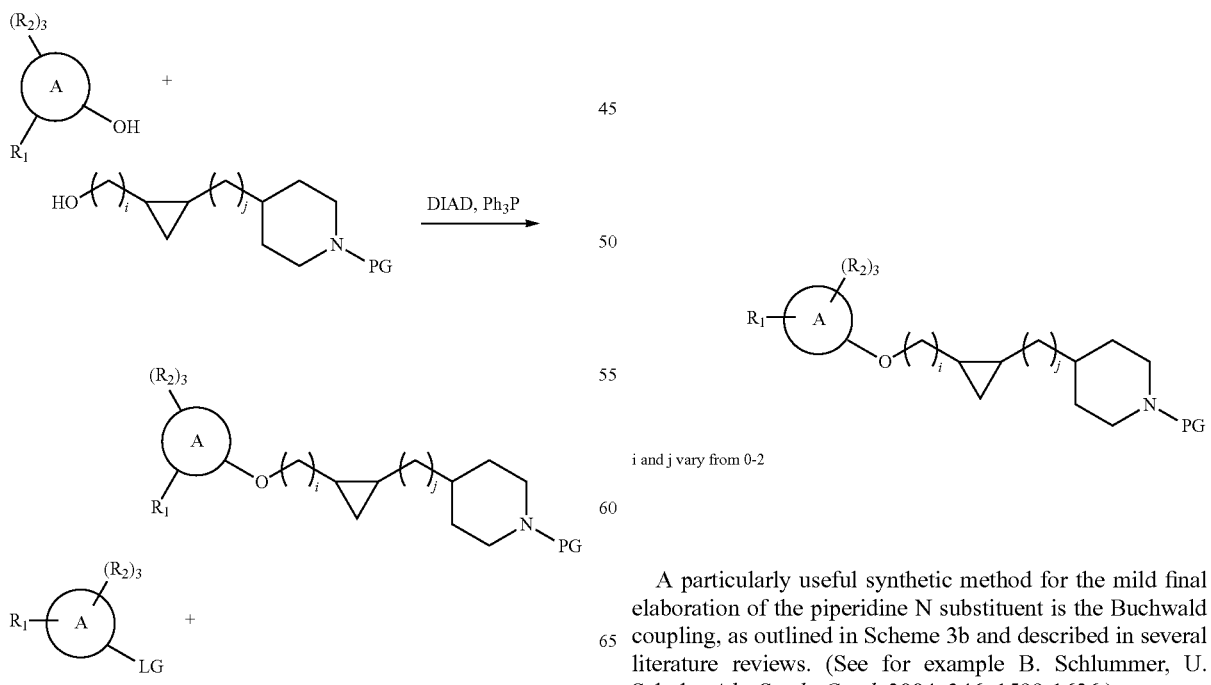

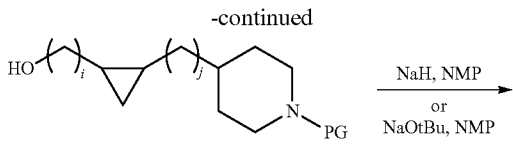

A particularly useful synthetic method for the mild final elaboration of the piperidine N substituent is the Buchwald coupling, as outlined in Scheme 3b and described in several literature reviews. (See for example B. Schlummer, U. Scholtz *Adv. Synth. Catal.* 2004, 346, 1599-1626.)

SCHEME 3b

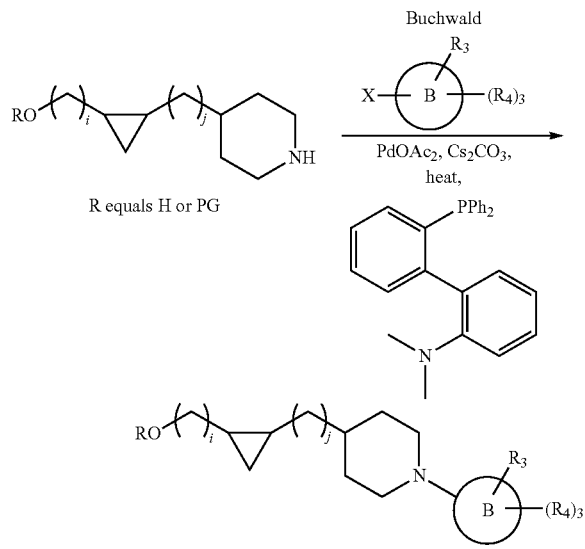

R equals H or PG

SCHEME 6

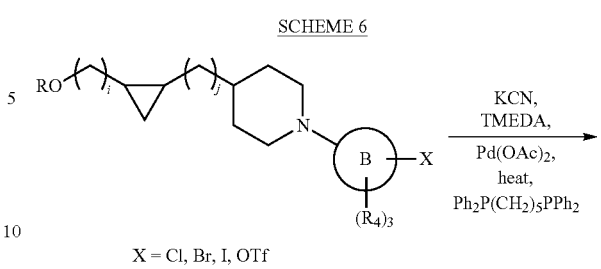

X = Cl, Br, I, OTf

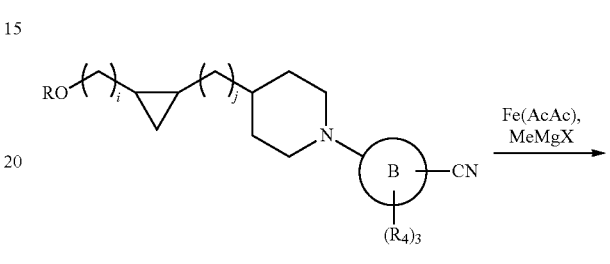

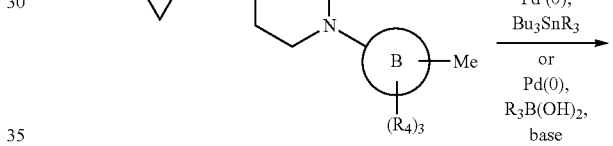

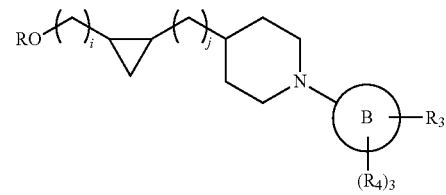

i and j vary from 0-2
R is H or PG

For some substitution patterns, it is more expedient to introduce the piperidine N substituent by de novo ring synthesis. The well known pyrimidine synthesis shown in Scheme 5 is one example of a broad variety of such methods.

SCHEME 5

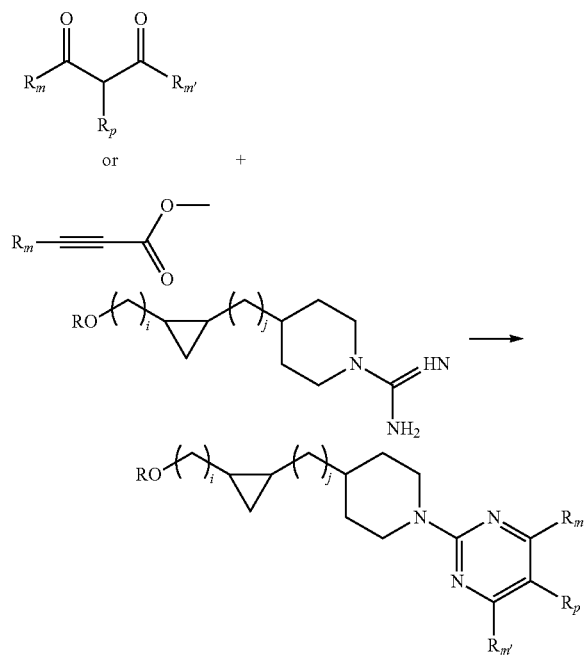

The meta and para substituents; $R_m$, $R_p$ and $R_{m'}$ are selected from $R_3$ and $R_4$
R is H or PG When the N-Aryl or N-heteroaryl residue is substituted with an X group (where X=Cl, Br, I or OTf) it is possible to further functionalize the residue utilizing iron or palladium organometallic mediated coupling reactions. Methods with extraordinarily broad applicability are metal mediated couplings outlined in Scheme 6.

Solvents specified as "dry" or "anhydrous" may be commercial anhydrous solvent or solvent distilled from the appropriate drying agent under inert gas. (See *Purification of Laboratory Chemicals* D. D. Perrin, Elsevier Science.) Cyclopropanation reactions are run under rigorous exclusion of air in distilled solvent. Note the exotherm warning reported by A. B. Charette, et al in *JACS* 120, 46, 11943-11952, page 11945.

Many examples are prepared as the racemic mixture and separated by chromatography on chiral stationary phase. Several commercially available stationary phases are suitable for this purpose. Commercial Chiralpak IA 4.6×250 mm, 5µ columns are typically used for analytical work and semi-prep

EXAMPLES

Preparative Example 1

Preparation of rac cis tert-Butyl 4-[2-(2-hydroxyethyl)cyclopropyl]piperidine-1-carboxylate, i.e. (tert-butyl 4-[(1S,2R)-2-(2-hydroxyethyl)cyclopropyl]piperidine-1-carboxylate and tert-butyl 4-[(1R,2S)-2-(2-hydroxyethyl)cyclopropyl]piperidine-1-carboxylate)

Step 1. Preparation of tert-Butyl 4-[(1Z)-4-(benzyloxy)but-1-en-1-yl]piperidine-1-carboxylate

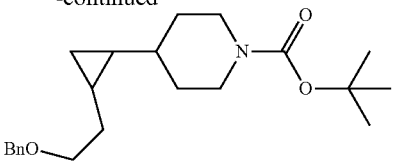

(3-Benzyloxypropyl)triphenylphosphonium bromide (2.88 g, 5.86 mmol) was suspended in 15 mL THF and cooled to 0° C. Sodium bis(trimethylsily)amide (1M in THF, 5.63 mL, 5.63 mmol) was added dropwise. The mixture turned deep orange. tert-Butyl 4-formylpiperidine-1-carboxylate (1 g, 4.69 mmol) in 3 mL THF was added after 5 minutes. Color faded to slight yellow. The reaction was stirred at room temperature for 1.5 hours, before quenching with saturated aqueous ammonium chloride solution. The aqueous layer was extracted twice with ethyl acetate. The organic layers were combined, washed with water and brine, dried over sodium sulfate, filtered, concentrated and purified by passing through a 40 gram Biotage silica gel cartridge using 20% EtOAc/hexanes to afford the product as colorless oil. NMR integration indicated >20:1 Z/E selectivity. LRMS calc: 345.2; obs: 346.5 (M+1).

Step 2. rac-tert-butyl 4-{2-[2-(benzyloxy)ethyl]cyclopropyl}piperidine-1-carboxylate, i.e. (tert-butyl 4-{(1S,2R)-2-[2-(benzyloxy)ethyl]cyclopropyl}piperidine-1-carboxylate and tert-butyl 4-{(1R,2S)-2-[2-(benzyloxy)ethyl]cyclopropyl}piperidine-1-carboxylate)

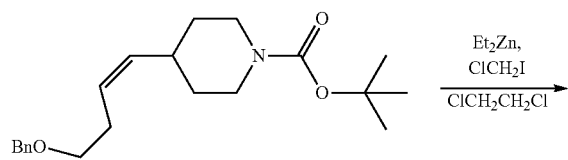

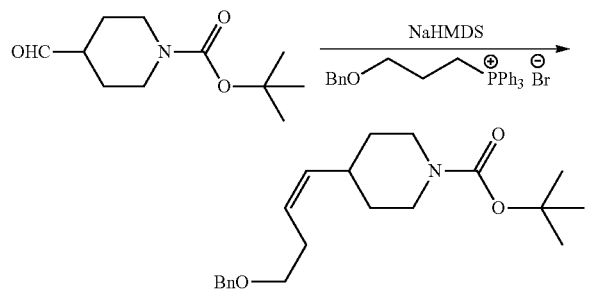

Dichloroethane (5 mL) was degassed and purged with argon three times before diethylzinc solution (1M in hexanes, 1.74 mL, 1.74 mmol) was added. The solution was cooled to −20° C. Chloroiodomethane (613 mg, 3.47 mmol) was added dropwise while maintaining internal temperature below −15° C. After stirring for 10 minutes at −20° C., tert-butyl 4-[(1Z)-4-(benzyloxy)but-1-en-1-yl]piperidine-1-carboxylate (from step 1, this Example 200 mg, 0.579 mmol) in degassed dichloroethane (1 mL) was added dropwise. The reaction was stirred at −20° for 10 minutes before slowly warming to RT. The reaction mixture was cooled to −10° C. after 1 hour. A 1:4 mixture of saturated aqueous ammonium chloride and aqueous ammonium hydroxide (28% w/w) was slowly introduced to quench excess reagents. The mixture was stirred at room temperature for 3 hours. The aqueous layer was separated and extracted twice with dichloromethane. The combined organic layers were washed with brine, dried over sodium sulfate, concentrated and purified by column chromatography eluting with 25% EtOAc/hexanes to give the product as colorless oil. LRMS calc: 359.25; obs: 360.5 (M+1).

Step 3. rac cis tert-Butyl 4-[2-(2-hydroxyethyl)cyclopropyl]piperidine-1-carboxylate, i.e. (tert-butyl 4-[(1S,2R)-2-(2-hydroxyethyl)cyclopropyl]piperidine-1-carboxylate and tert-butyl 4-[(1R,2S)-2-(2-hydroxyethyl)cyclopropyl]piperidine-1-carboxylate)

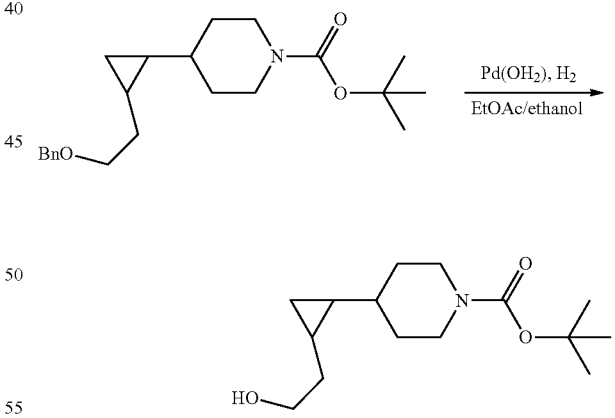

Racemic-cis tert-butyl 4-{2-[2-(benzyloxy)ethyl]cyclopropyl}piperidine-1-carboxylate from step 2 (140 mg, 039 mmol) was dissolved in 5 mL ethyl acetate and ethanol (1:1). The solution was degassed and purged with nitrogen 3 times, before palladium hydroxide (20% on carbon, 54.6 mg, 0.08 mmol) was added. The mixture was degassed and purged with hydrogen three times. The reaction was stirred under a hydrogen balloon at room temperature for 1 hour and filtered through a small plug of silica gel to remove catalyst. The silica gel plug was thoroughly washed with acetone. The eluent was concentrated to give the crude product, which was used without further purification. LRMS talc: 269.2; obs: 270.2 (M+1).

Preparative Example 2

Preparation of cis tert-butyl 4-[2-(2-hydroxyethyl)cyclopropyl]piperidine-1-carboxylate Step 1 Preparation of tert-butyl 4-[(4R)-5-(benzyloxy)-4-hydroxypent-1-yn-1-yl]piperidine-1-carboxylate

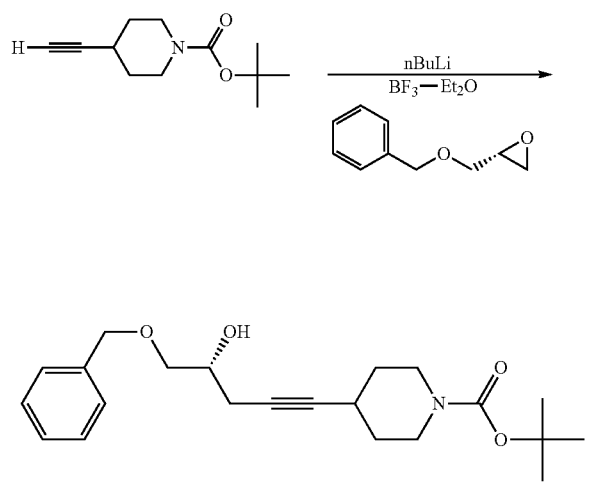

Commercially available tert-butyl 4-ethynylpiperidine-1-carboxylate was dissolved in 40 ml of THF and cooled to −78° C. forming a white slurry. Titrated n-BuLi (2.2 M in hexanes, 23.9 ml, 52.6 mmol) was added dropwise with stirring. The clear colorless solution was stirred at −78° C. for 5 minutes. A solution of the R-(+) benzyl glycidyl epoxide (8.63 g, 52.6 mmol) in THF (20 ml) was added dropwise. BF₃ etherate (8.43 g, 59.7 mmol) was then added dropwise with a syringe and the solution stirred at −78° C. for 1 hour. Sat'd aq. NH₄Cl was added (100 ml), the mixture warmed to RT, diluted with water to dissolve any remaining solids, and extracted with iPrOAc (3×100 ml). The organic fractions were combined, washed with brine, dried over MgSO₄, filtered and stripped. Crude product was purified by chromatography on SiO₂ eluting with 30% EtOAc:Hexanes. The alcohol was repurified by chromatography on a C18 reversed phase column (12-100% water:acetonitrile 0.1% TEA as two runs.). Product containing fractions were combined, reduced in volume by approximately 50%,—made basic by addition of sat'd aq. NaHCO₃, water was added to dissolve some white solids, and the mixture extracted with iPrOAc (3×100). The organic fractions were combined, washed with brine, dried over MgSO₄, filtered, and stripped.

Step 2 Preparation of tert-butyl 4-[(1Z,4R)-5-benzyloxy)-4-hydroxypent-1-en-1-yl]piperidine-1-carboxylate

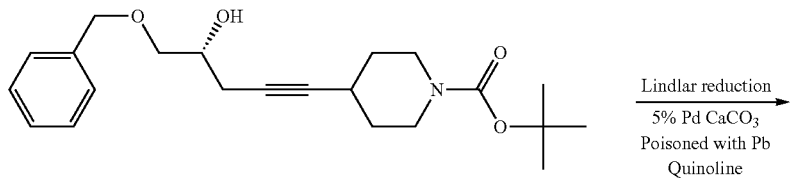

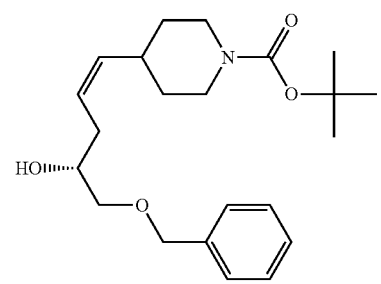

The alcohol from step 1 of this example (9.1 g, 24.4 mmol) was dissolved in EtOAc (100 ml) and quinoline (0.48 ml, 4.03 mmol) was added. Lindlar's catalyst (1.04 g) was added and the vessel evacuated and refilled three times with H₂. The slurry was stirred under a H₂ atmosphere for 40 min. The SM was completely consumed. The mixture was filtered through celite and rinsed with EtOAc (4×50 ml). The volume of EtOAc was reduced ~80% in vac. The remaining solution was diluted with ether (100 ml) and washed with 2N HCl (100 ml). The aqueous fraction was re-extracted with ether (2×50 ml), organics combined and washed with 15 ml 2 N HCl. The organic fraction was washed with sat'd aq. NaHCO₃, brine, dried over MgSO₄, filtered, and stripped. The resulting oil was purified by chromatography on SiO₂ 30% eluting with EtOAc:Hexanes.

Step 3: Preparation of tert-butyl 4-{(1R,2S)-2-[(2R)-3-(benzyloxy)-2-hydroxypropyl]cyclopropyl}piperidine-1-carboxylate

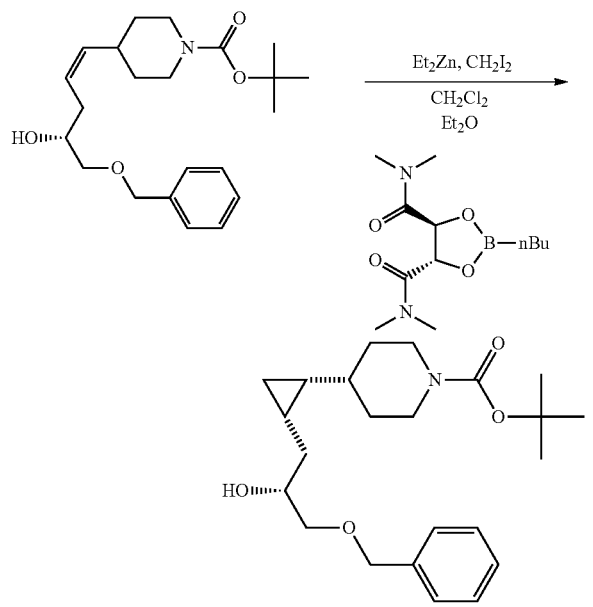

Dichloromethane stabilized with EtOH was distilled from CaH₂ under N₂ and sparged with N₂ to maintain oxygen free solvents.

A 500 ml 3N round bottom flask was equipped with an addition funnel topped with a 3 way stopcock and internal thermal couple. The apparatus was evacuated and backfilled with N₂ 4 times. To this degassed vessel was added 20 mL DCM, Diethyl Ether (5.06 g, transferred by weight) and a solution of Et₂Zn (8.43 g, 68.2 mmol, in 30 ml DCM) under a N₂ atmosphere. The solution was cooled to −20° C. and a solution of CH₂I₂ (36.5 g, 136 mmol, in 20 ml DCM) was added dropwise. The temperature is monitored with an internal temperature probe. The rate of addition was altered to maintain a constant −20° C. internal temperature. A fine precipitate forms after the addition is ~80% complete. The mixture was stirred for 10 minutes.

A solution of the commercially available (S,S) dioxaborolane ligand (7.37 g, 27.3 mmol) in DCM (20 mL) was added. The mixture was stirred for 10 minutes. The precipitate dissolves yielding a clear solution. A solution of the alkene from step 2 of this example (8.53 g, 22.7 mmol) in DCM (20 mL)

was added. The solution was warmed to 0° C. and stirred for 24 hours. The solution remains clear after stirring for 24 hours. The reaction was quenched after 24 hr by addition of 50 ml of sat'd aq. NH₄O. The mixture was placed in a separatory funnel, 250 ml DCM and 200 ml 10% HCl (aq) added, shaken, and the layers separated. The aqueous layer was re-extracted with DCM (2×150 ml), the organic layers combined, transferred to a Morton flask. 2N NaOH (300 ml) and 50 ml of 30% H₂O₂ were added. The biphasic solution was stirred vigorously for 12 hours. The layers were separated and the aqueous phase was re-extracted with DCM (2×150 ml), the organic phases were combined, washed with 10% HCl (aq, 250 ml), 1N Na₂S₂O₃ (250 ml), sat'd NaHCO₃ (250 ml), brine (250 ml), dried over MgSO₄, filtered and stripped. The material was purified by chromatography on SiO₂ eluting with 30% EtOAc:Hexanes. The desired product is obtained as a mixture with the minor diastereomer and the residual SM. The desired diastereomer was isolated by chromatography on Chiralpak IA stationary phase.

Step 4 Preparation of cis tert-butyl 4-[2-(2-hydroxyethyl)cyclopropyl]piperidine-1-carboxylate

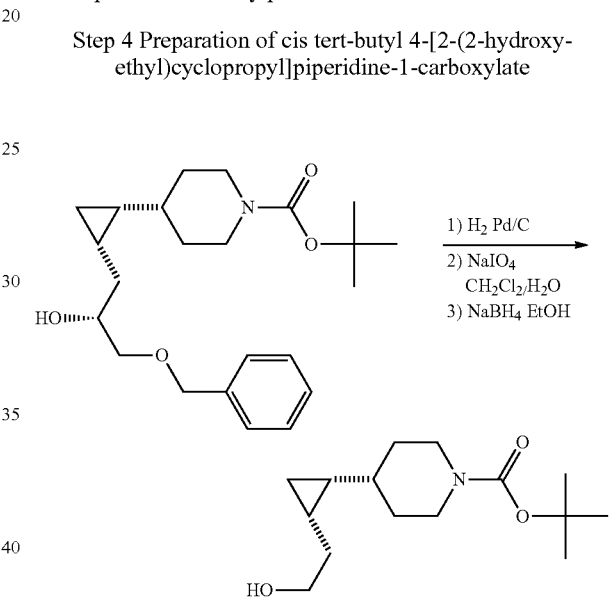

The tert-butyl 4-{(1R,2S)-2-[(2R)-3-(benzyloxy)-2-hydroxypropyl]cyclopropyl}piperidine-1-carboxylate from step 3 of this example (4.3 g, 11 mmol) was transferred to a Parr shaker pressure tube in 55 ml 1:1 EtOAc/Ethanol with 0.88 mgs Aldrich palladium hydroxide (20% wt on carbon-Degussa type E101). The mixture was shaken at 50 psig hydrogen on a Parr shaker. HPLC check at 30 min. indicated complete conversion. The product was filtered through Celite, washed with ethanol, and reduced to an oil i. vac.

The crude debenzylation product was dissolved in CH₂Cl₂ (56 ml) and cooled in ice. Sodium periodate (4.77 g, 22.3 mmol) was dissolved in water (56 ml) and added slowly dropwise. The milky mixture was stirred vigorously at 0° C. HPLC indicated complete cleavage at 30 min. at 0° C. The reaction mixture was diluted with brine and CH₂Cl₂. The mixture was extracted three times with CH₂Cl₂, dried over MgSO₄ and reduced i. vac.

The crude aldehyde was redissolved in EtOH (56 ml), sodium borohydride (0.422 g, 11.2 mmol) was added as a solid and the mixture stirred at RT. The reduction is complete in 30 min. Saturated aq NH₄Cl aq (70 ml) was added to quench, and the mixture reduced to a paste i. vac. The result was diluted with water (350 ml), and iPrOAc. The mixture was extracted with iPrOAc (3×), washed with brine, dried over MgSO₄, filtered and reduced i. vac. The crude product was purified by chromatography on SiO₂ eluting with 40% EtOAc:Hexanes.

Preparative Example 3

Preparation of rac trans tert-butyl 4-[2-(2-hydroxyethyl)cyclopropyl]piperidine-1-carboxylate, i.e. (tert-butyl 4-[(1R,2R)-2-(2-hydroxyethyl)cyclopropyl]piperidine-1-carboxylate and tert-butyl 4-[(1S,2S)-2-(2-hydroxyethyl)cyclopropyl]piperidine-1-carboxylate)

Step 1: tert-Butyl-4-[(1E)-3-methoxy-3-oxoprop-1-en-1-yl]piperidine-1-carboxylate

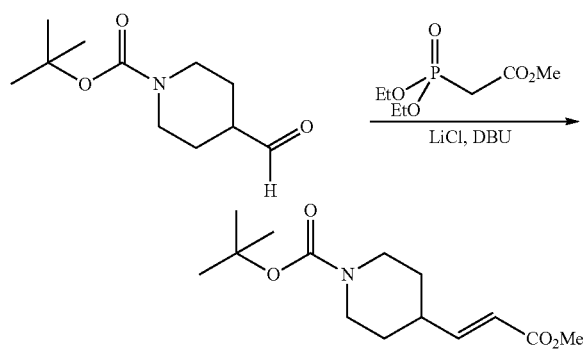

Lithium chloride (1.013 gram, 1.23 eq.) was suspended in 100 mL HPLC grade acetonitrile. Methyl (diethoxyphosphoryl)acetate (4.33 gram, 1.06 eq.) was added slowly at room temperature, followed by DBU (3.14 gram, 1.06 eq.) and the indicated commercially available aldehyde (4.14 gram, 1 eq.) in acetonitrile (10 mL). The mixture was stirred at room temperature for 3 hours. Excess solvent was removed i. vac. The residue was diluted with water (100 mL) and was extracted with ether (50 mL×3). The combined organic layers were dried over sodium sulfate, filtered, and concentrated to give the crude ester as pale yellow oil, which was used in the next step without further purification.

Step 2: tert-Butyl 4-[(1E)-3-hydroxyprop-1-en-1-yl]piperidine-1-carboxylate

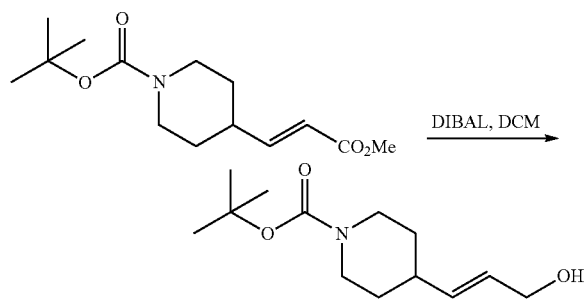

1 M DiBAl—H in dichloromethane (42 mL, 2.2 eq.) was added slowly, via an addition funnel, over 20 min to a well stirred solution of the α,β-unsaturated ester from step 1 of this example (5.14 gram, 1 eq.) in anhydrous DCM (100 mL) under argon atmosphere at −78° C. The resulting solution was warmed to 0° C. after completion of addition and was kept at that temperature for 30 min. The reaction was cooled back to −78° C. and 4 mL MeOH was added slowly to quench the excess DiBAl-H. The cold solution was further stirred at −78° C. for 10 min before pouring into 150 mL saturated aqueous Rochelle (sodium potassium tartrate) salts solution. The mixture was vigorously stirred at room temperature for 3 hours until it turned clear. The organic layer was separated, dried over sodium sulfate, filtered and concentrated i. vac. The residue was further purified by column chromatography using acetone/hexanes (20%, isocratic) to give the desired product as colorless oil.

Step 3: tert-Butyl 4-[(1E)-3-benzyloxy)prop-1-en-1-yl]piperidine-carboxylate

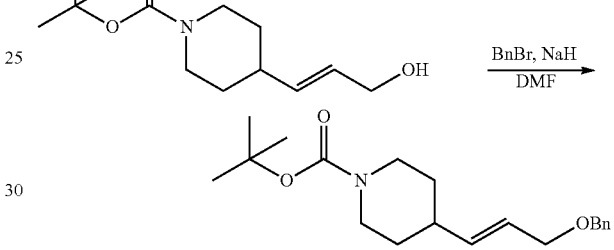

Sodium hydride (60% in mineral oil, 2.73 g, 1.1 eq.) was suspended in anhydrous DMF (180 mL) and cooled to 0° C. The allylic alcohol from step 2 of this example (15 g, 1 eq.) in anhydrous DMF (20 mL) was added slowly. The mixture was stirred at room temperature for 15 min under nitrogen atmosphere. Benzyl bromide (8.13 mL, 1.1 eq.) was then added dropwise. The mixture was stirred at room temperature for 2 hours. The reaction was diluted with 300 mL water and 200 mL EtOAc. The aqueous layer was separated and extracted twice using EtOAc (50 mL×2). The combined organic layers were dried over sodium sulfate, concentrated and purified by column chromatography eluting with EtOAc/hexanes (15%, isocratic) to give the desired benzyl ether as colorless oil.

Step 4: rac trans tert-Butyl 4-{2-[(benzyloxy)methyl]cyclopropyl}piperidine-1-carboxylate, i.e. tert-butyl 4-{(1S,2R)-2-[(benzyloxy)methyl]cyclopropyl}piperidine-1-carboxylate and tert-butyl 4-{(1R,2S)-2-[(benzyloxy)methyl]cyclopropyl}piperidine-1-carboxylate)

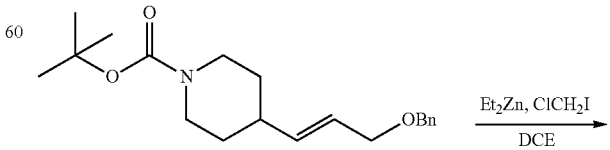

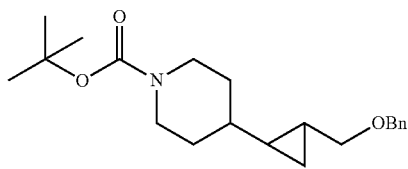

Anhydrous dichloroethane (130 mL) in a 500 mL round bottom flask was degassed and backfilled with argon three times. Diethylzinc (1 M in DCM, 87 mL, 5 eq.) was added rapidly via a syringe under argon. The solution was cooled to −18° C. Chloroiodomethane (12.61 mL, 10 eq.) was added, via a syringe, at a rate such that the internal temperature remained below −10° C. The reaction mixture was stirred at −18° C. for 10 min. A white precipitate was observed. The benzyl protected allylic alcohol from step 3 of this example (6 g, 1 eq.) in anhydrous DCE (30 mL) was added slowly while maintaining internal temperature below −5° C. The reaction was stirred at −18° C. and was monitored by LC-MS. The reaction generally finished within 10-30 min. Upon completion the reaction was quenched, while cold, with 100 mL aqueous saturated ammonium chloride solution and 50 mL 28% aqueous ammonium hydroxide. The mixture was warmed to room temperature and stirred vigorously until both phases became clear. The organic phase was separated, dried over sodium sulfate, concentrated and purified by column chromatography eluting with EtOAc/hexanes (15%, isocratic) to give the product as a colorless oil.

Step 5: rac trans tert-Butyl 4-[2-(hydroxymethyl)cyclopropyl]piperidine-1-carboxylate, i.e. tert-butyl 4-[(1S,2R)-2-(hydroxymethyl)cyclopropyl]piperidine-1-carboxylate and tert-butyl 4-[(1R,2S)-2-(hydroxymethyl)cyclopropyl]piperidine-1-carboxylate

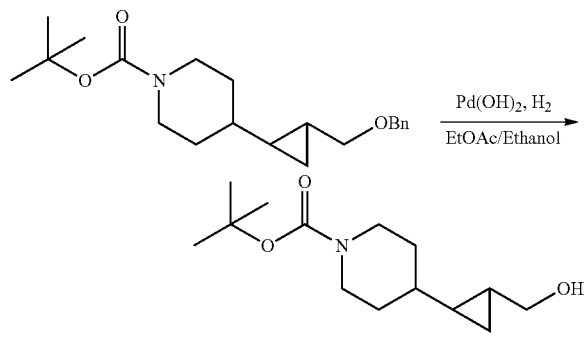

The benzyl protected hydroxyethylcyclopropane from step 4 of this example (6 g, 1 eq.) was dissolved in a mixture of HPLC grade EtOAc (75 mL) and ethanol (75 mL). The solution was degassed and backfilled with nitrogen, before Pd(OH)$_2$ (20 w % on carbon, 2.34 g, 0.2 eq.) was added. The reaction vessel was degassed and backfill with hydrogen three times. The reaction mixture was rigorously stirred under a 1 L hydrogen balloon and was monitored by LC-MS. The deprotection is typically complete within 2 hours. The mixture was then filtered through a plug of silica gel (100 g) and was washed thoroughly with 50% EtOAc/hexanes (1 L). Concentration gave the cyclopropanol as colorless oil.

Step 6: trans rac-tert-Butyl 4-(2-formylcyclopropyl)piperidine-1-carboxylate, i.e. tert-butyl 4-[(1S,2R)-2-formylcyclopropyl]piperidine-1-carboxylate and tert-butyl 4-[(1R,2S)-2-formylcyclopropyl]piperidine-1-carboxylate

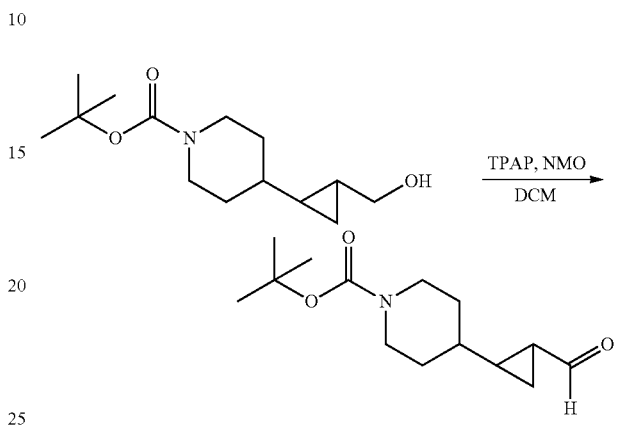

A mixture of the hydroxyethylcyclopropane from step 5 of this example (9 g, 1 eq.), powdered 4 Å activated molecular sieves (18 g) and N-methylmorpholine oxide (6.19 g, 1.5 eq.) was stirred in anhydrous DCM. (200 mL) under nitrogen for 15 min at room temperature. TPAP (1.24 g, 0.1 eq.) was added in one portion. The reaction was exothermic and ice-bath was used occasionally to maintain internal temperature around room temperature. The mixture was stirred at room temperature for 1 hour. The reaction was diluted with 500 mL ether and stirred for 10 min. The mixture was filtered through a plug of silica gel (200 g) which was washed thoroughly with 50% acetone/hexanes (2 L). Concentration afforded the aldehyde as colorless oil.

Step 7: trans rac trans tert-Butyl 4-(2-vinylcyclopropyl)piperidine-1-carboxylate, i.e. tert-butyl 4-[(1S,2S)-2-vinylcyclopropyl]piperidine-1-carboxylate and tert-butyl 4-[(1R,2R)-2-vinylcyclopropyl]piperidine-1-carboxylate

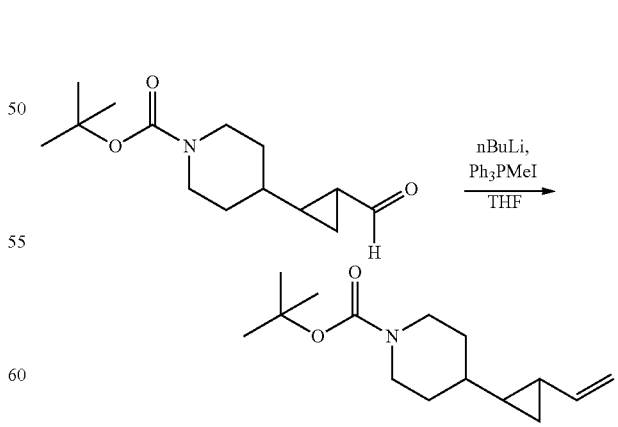

Triphenylmethyl phosphonium iodide (1.92 g, 1.2 eq.) was suspended in anhydrous THF (7 mL) under nitrogen and cooled to −78° C. n-BuLi (1.6 M, 2.84 mL, 1.15 eq.) was added slowly and the mixture was stirred for 15 min. The suspension turned yellow. The aldehyde from step 6 of this example (1 g, 1 eq.) in anhydrous THF (3 mL) was added slowly. The reaction was warmed to room temperature and stirred for 30 min. Saturated aqueous ammonium chloride was added. The aqueous layer was extracted twice with EtOAc. The combined extracts were dried over sodium sulfate, concentrated and purified by column chromatography eluting with EtOAc/hexanes (15%, isocratic) to give the desired olefin as colorless oil.

Step 8: rac-trans-tert-butyl 4-[2-(2-hydroxyethyl)cyclopropyl]piperidine-1-carboxylate, i.e. tert-butyl 4-[(1R,2R)-2-(2-hydroxyethyl)cyclopropyl]piperidine-1-carboxylate and tert-butyl 4-[(1S,2S)-2-(2-hydroxyethyl)cyclopropyl]piperidine-1-carboxylate

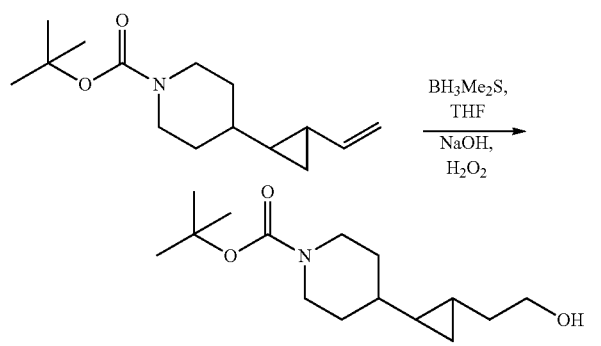

Borne dimethylsulfide complex (1.0 M in THF, 0.7 mL, 0.5 eq.) was dissolved in anhydrous THF (2 mL) and cooled in 0° C. The olefin from step 7 of this example (350 mg, 1 eq.) in anhydrous THF (0.8 mL) was added slowly. The mixture was stirred at room temperature for 2 hours. Aqueous sodium hydroxide solution (5 M, 1.5 mL) was added very slowly. Significant gas evolution was observed. The reaction vessel was cooled using an ice-bath as necessary. Hydrogen peroxide solution (30%, 1.39 mL) was added slowly. The mixture was stirred at room temperature for 2 hours. Water (3 mL) was added. The mixture was extracted three times with EtOAc. The combined organic layers were washed with brine, dried over sodium sulfate, concentrated and purified by column chromatography using EtOAc/hexanes (40%, isocratic) to give the desired final product as colorless oil.

Preparative Example 4

Preparation of rac trans tert-butyl 4-{[2-(hydroxymethyl)cyclopropyl]methyl}piperidine-1-carboxylate, i.e. (tert-butyl 4-{[(1R,2R)-2-(hydroxymethyl)cyclopropyl]methyl}piperidine-1-carboxylate and tert-butyl 4-{[(1S,2S)-2-(hydroxymethyl)cyclopropyl]methyl}piperidine-1-carboxylate

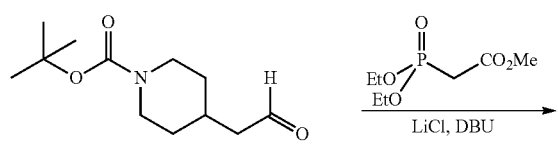

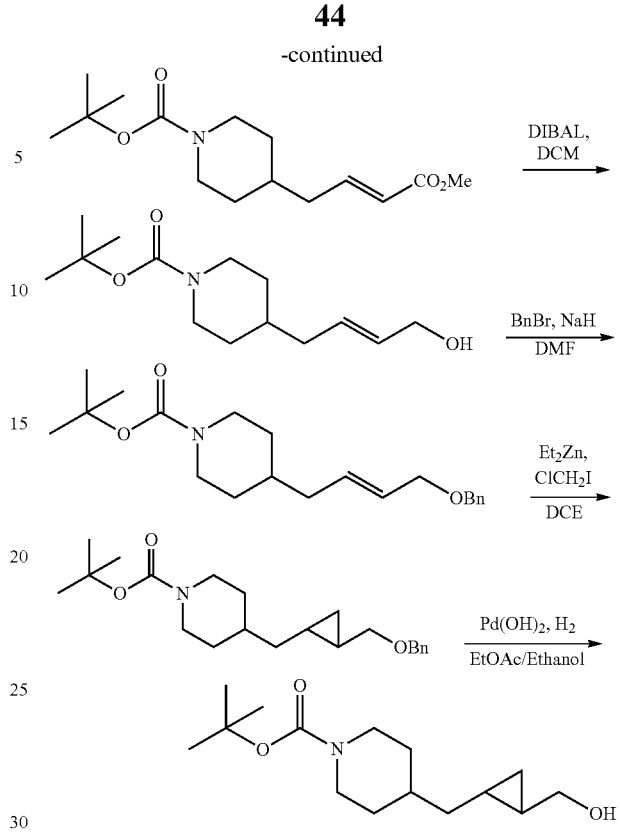

The title compound was prepared from tert-butyl 4-(2-oxoethyl)piperidine-1-carboxylate by a route analogous to the preparation of Example 3, steps 1-5, as indicated in the scheme above.

Separation of Enantiomers on Chiral Stationary Phase tert-butyl 4-{[(1S,2S)-2-(hydroxymethyl)cyclopropyl]methyl}piperidine-1-carboxylate and tert-butyl 4-{[(1R,2R)-2-(hydroxymethyl)cyclopropyl]methyl}piperidine-1-carboxylate

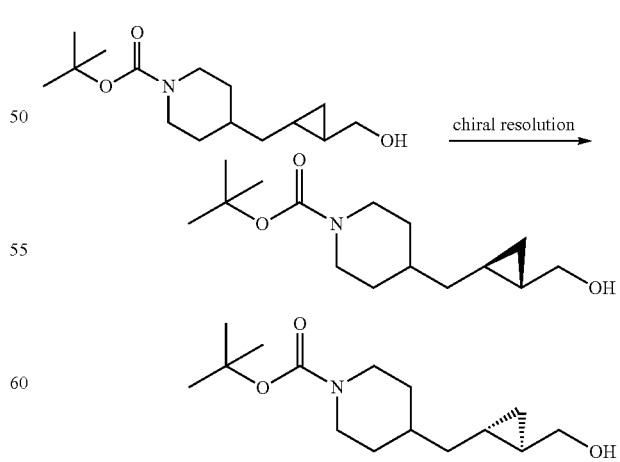

The title enantiomers were obtained by resolving rac trans tert-butyl 4-{[2-(hydroxymethyl)cyclopropyl]methyl}piperidine-1-carboxylate on a chiralpak IA 21.2×250 mm under SFC conditions (50 mL/min, 100 bar, 12% MeOH/$CO_2$), 35° C. Retention time—faster enantiomer (tert-butyl 4-{[(1S,2S)-2-(hydroxymethyl)cyclopropyl]methyl}piperidine-1-carboxylate): T=2.89 min; slower enantiomer (tert-butyl 4-{[(1R,2R)-2-(hydroxymethyl)cyclopropyl]methyl}piperidine-1-carboxylate): T=3.43 min.

Preparative Example 5

Preparation of rac cis tert-butyl 4-{[2-(hydroxymethyl)cyclopropyl]methyl}piperidine-1-carboxylate, i.e. tert-butyl 4-{[(1S,2R)-2-(hydroxymethyl)cyclopropyl]methyl}piperidine-1-carboxylate and tert-butyl 4-{[(1R,2S)-2-(hydroxymethyl)cyclopropyl]methyl}piperidine-1-carboxylate Step 1: tert-butyl 4-(3,3-dibromoprop-2-en-1-yl)piperidine-1-carboxylate

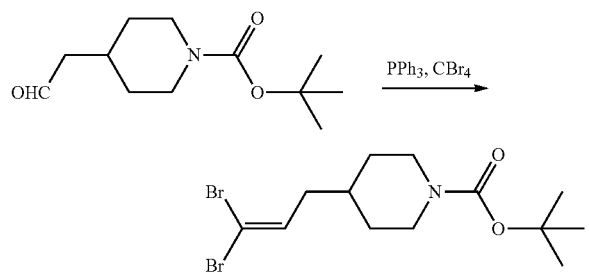

Carbon tetrabromide (46.7 g, 141 mmol) was dissolved in 200 mL dichloromethane. The solution was cooled in an ice-water bath and triphenylphosphine (73.9 g, 282 mmol) in 200 mL dichloromethane was introduced via an addition funnel over 20 min. The reaction mixture was stirred at 0° C. for 10 min and a solution of tert-butyl 4-(2-oxoethyl)piperidine-1-carboxylate (16 g, 70.4 mmol) in 100 mL dichloromethane was added via an addition funnel. The solution was stirred at 0° C. for 1 hour. Water (250 mL) was added and aqueous layer was extracted 3 times with 100 mL dichloromethane. The combined organic layer was washed with brine, dried over sodium sulfate, filtered and concentrated. 300 mL ether was added to the residue, and the resulting suspension was filtered. The solid was washed 3 times with 150 mL ether. The combined filtrate was concentrated and passed through a plug of silica gel, washed thoroughly with 10% acetone/hexanes to afford yellow oil which was used without further purification.

Step 2: tert-butyl 4-(4-hydroxybut-2-yn-1-yl)piperidine-1-carboxylate

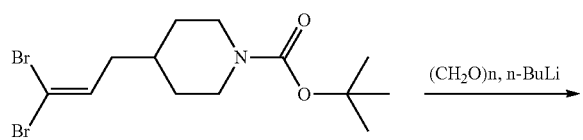

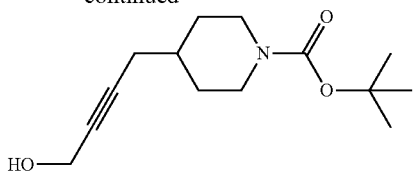

tert-Butyl 4-(3,3-dibromoprop-2-en-1-yl)piperidine-1-carboxylate from step 1 of this Example (19.5 g, 50.9 mmol) was dissolved in THF (170 mL) and cooled to −78° C. n-BuLi (2.5 M in hexanes, 46.8 mL, 117 mmol) was added slowly, maintaining internal temperature below −65° C. The mixture was stirred for additional 30 min, before paraformaldehyde (4.59 g, 152.7 mmol) was added in one portion. The reaction was stirred at −78° C. for 30 min and warmed to room temperature and allowed to stir at RT for 1 hour. Saturated aqueous ammonium chloride was added, and the aqueous layer was extracted 3 times with ethyl acetate. Column chromatography eluting with 30% acetone/hexanes afforded the product as colorless oil.

Step 3: tert-butyl 4-[(2Z)-4-hydroxybut-2-en-1-yl]piperidine-1-carboxylate

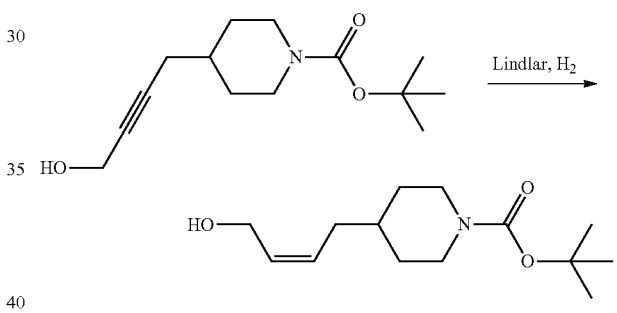

tert-Butyl 4-(4-hydroxybut-2-yn-1-yl)piperidine-1-carboxylate from step 2 of this example (10.6 g, 41.8 mmol) was dissolved in 200 mL MeOH and 3,6-Dithia-1,8-octanediol (191 mg, 1.05 mmol) was added, followed by Lindlar's catalyst (5% w/w, 4.45 g, 2.1 mmol). The reaction vessel was degassed and back filled with hydrogen 3 times and further stirred under a hydrogen balloon at room temperature for 1 hour. The reaction was filtered through Celite and concentrated under vacuum to afford the crude product as colorless oil which was used directly in the next step.

Step 4-8: Preparation of rac cis tert-butyl 4-{[2-(hydroxymethyl)cyclopropyl]methyl}piperidine-1-carboxylate, i.e. tert-butyl 4-{[(1S,2R)-2-(hydroxymethyl)cyclopropyl]methyl}piperidine-1-carboxylate and tert-butyl 4-{[(1R,2S)-2-hydroxymethyl)cyclopropyl]methyl}piperidine-1-carboxylate

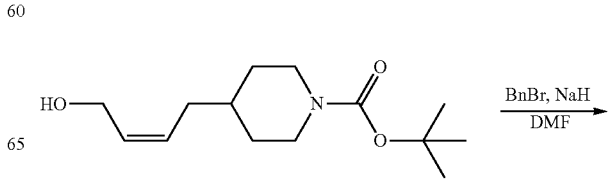

-continued

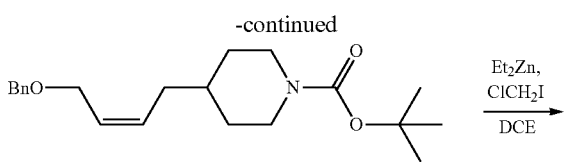

The title compound was prepared from tert-butyl 4-[(2Z)-4-hydroxybut-2-en-1-yl]piperidine-1-carboxylate, step 3 of this example, by procedures analogous to the preparation of Example 3, steps 3-5, as indicated in the scheme above.

Example 6

Preparation of rac cis-5-chloro-2-[4-(2-{2-[4-(methylsulfonyl)phenoxy]ethyl}cyclopropyl)piperidin-1-yl]pyrimidine, i.e., 5-chloro-2-[(4-((1S,2R)-2-{2-[4-(methylsulfonyl)phenoxy]ethyl}cyclopropyl)piperidin-1-yl]pyrimidine and 5-chloro-2-[4-((1R,2S)-2-{2-[4-(methylsulfonyl)phenoxy]ethyl}cyclopropyl)piperidin-1-yl]pyrimidine Step 1. Preparation of 2,5-dichloropyrimidine

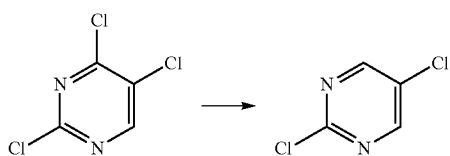 [SMILES: Clc1ncc(Cl)c(Cl)n1 ; Clc1cnc(Cl)nc1]

2,4,5-Trichloropyrimidine (25 g, 136 mmol) and zinc (26.7 g, 409 mmol, granular) were combined and THF (100 ml) added. The slurry was stirred at RT, glacial acetic acid was added (11.7 ml, 204 mmol) and the mixture heated at reflux for 2 hours. The mixture was cooled to RT, diluted with DCM (100 ml) and filtered through celite. The solution was then concentrated i. vac. The crude material was dissolved in DCM (100 ml), sated NaHCO$_3$ was added in small portions and shaken until the pH of the aqueous phase was 8. Then the pH was adjusted to 10 using 1N NaOH (aq), shaken and the layers separated. The organic fraction was dried over MgSO$_4$, filtered, and the volatiles removed i. vac. The material was purified by chromatography on SiO$_2$ eluting with 2% EtOAc: Hexanes.

Step 2. rac cis-2-{2-[1-(5-Chloropyrimidin-2-yl)piperidin-4-yl]cyclopropyl}ethanol

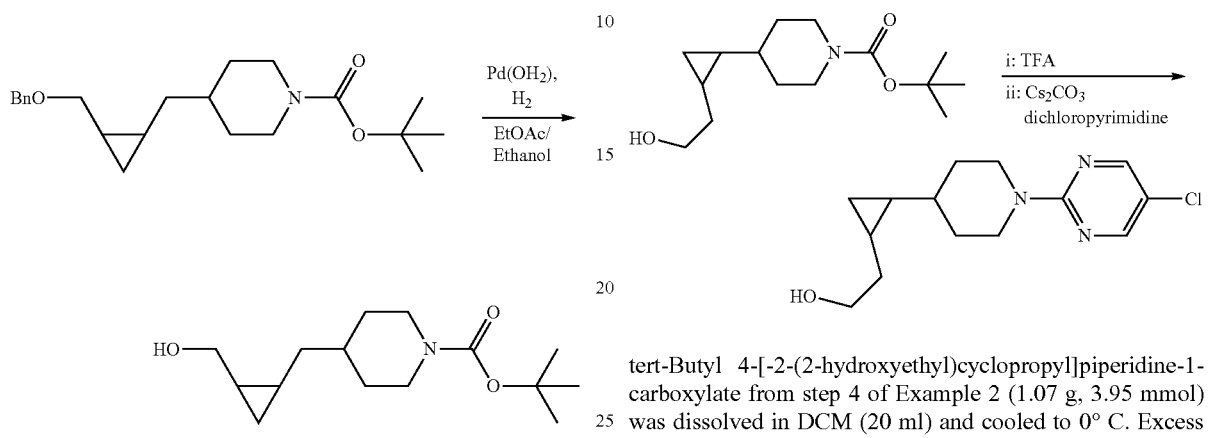

tert-Butyl 4-[-2-(2-hydroxyethyl)cyclopropyl]piperidine-1-carboxylate from step 4 of Example 2 (1.07 g, 3.95 mmol) was dissolved in DCM (20 ml) and cooled to 0° C. Excess TFA (20 ml) was added dropwise and the solution was stirred at 0° C. for 30 minutes. HPLC-MS shows no SM remaining. The volatiles were removed under vacuum. Residual TFA was further removed by stripping twice from DCM followed by drying i. vac. The resulting material was transferred to a pear-shaped flask in DCM and the volatiles removed i. vac.

The crude piperidine was dissolved in DMF (9 ml, 0.44 M) with the dichloropyrimidine from step 1 of this example (0.59 g, 3.95 mmol) and cesium carbonate (7.08 g, 21.7 mmol, 5.5 eq) was added. The mixture was stirred at RT for 6.0 hrs. The mixture was poured into 150 ml water and extracted with iPrOAc (3×100 ml). The organic phases were washed with brine, dried over Na$_2$SO$_4$, filtered and stripped. Crude material was purified by column chromatography on SiO$_2$ eluting with 40% EtOAc:Hexanes. LRMS calc: 281.1; obs: 282.2 (M+1).

Step 2b. 2-{(1S,2R)-2-[1-(5-chloropyrimidin-2-yl)piperidin-4-yl]cyclopropyl}ethanol

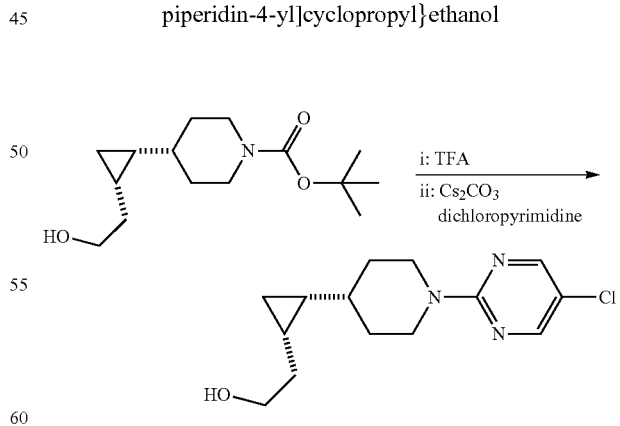

tert-butyl 4-[(1R,2S)-2-(2-hydroxyethyl)cyclopropyl]piperidine-1-carboxylate from step 4 of Example 2 (1.07 g, 3.95 mmol) was dissolved in DCM (20 ml) and cooled to 0° C. Excess TFA (20 ml) was added dropwise and the solution was stirred at 0° C. for 30 minutes. The volatiles were removed under vacuum. Residual TFA was further removed by stripping twice from DCM followed by drying i. vac. The resulting material was transferred to a pear-shaped flask in DCM and the volatiles removed i. vac.

The crude piperidine was dissolved in DMF (9 ml, 0.44 M) with the dichloropyrimidine from step 1 of this example (0.59 g, 3.95 mmol) and cesium carbonate (7.08 g, 21.7 mmol, 5.5 eq) was added. The mixture was stirred at RT for 6.0 hrs. The mixture was poured into 150 ml water and extracted with iPrOAc (3×100 ml). The organic phases were washed with brine, dried over $Na_2SO_4$, filtered and stripped. Crude material was purified by column chromatography on $SiO_2$ eluting with 40% EtOAc:Hexanes. LRMS calc: 281.1; obs: 282.2 (M+1).

Step 3. rac cis-5-chloro-2-[4-(2-{2-[4-(methylsulfonyl)phenoxy]ethyl}cyclopropyl)piperidin-1-yl]pyrimidine, i.e., 5-chloro-2-[4-((1S,2R)-2-{2-[4-(methylsulfonyl)phenoxy]ethyl}cyclopropyl)piperidin-1-yl]pyrimidine and 5-chloro-2-[4-((1R,2S)-2-{2-[4-(methylsulfonyl)phenoxy]ethyl}cyclopropyl)piperidin-1-yl]pyrimidine

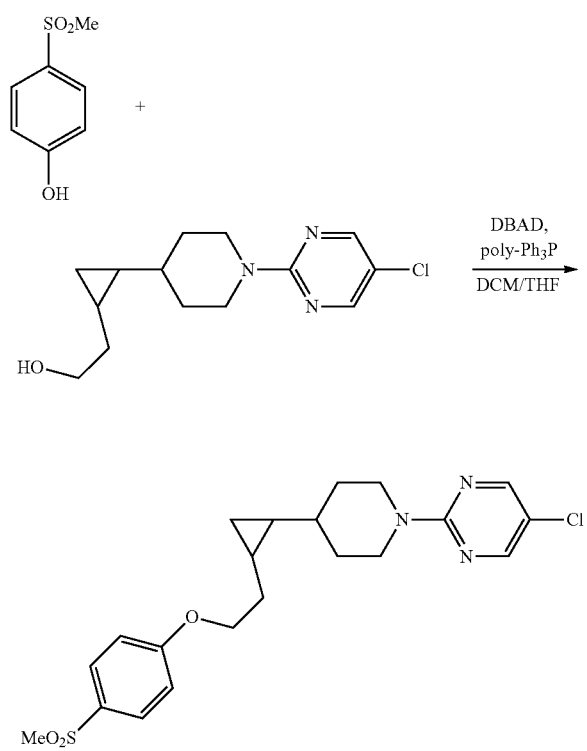

rac-2-{2-[1-(5-Chloropyrimidin-2-yl)piperidin-4-yl]cyclopropyl}ethanol from step 2 of this example (40 mg, 0.142 mmol), polymer-supported triphenylphosphine (3 mmol/g, 177 mg, 0.532 mmol) and 4-(methylsulfonyl)phenol (29.3 mg, 0.17 mmol) were mixed in 3 mL dichloromethane and THF (1:1). The mixture was cooled to 0° C. and DBAD was added. The cooling bath was removed and the reaction was stirred for 1 hour. The polymer was removed by filtration and was washed thoroughly with acetone. The filtrate was concentrated and purified by column chromatography through a 24 gram silica gel cartridge eluting with 15-30% EtOAc/hexanes to give the product as a white solid. LRMS calc: 435.1; obs: 436.6 (M+1).

Example 6a

Preparation of rac-cis 5-chloro-2-{-4-[2-(2-{[5-(methylsulfonyl)pyridin-2-yl]oxy}ethyl)cyclopropyl]piperidin-1-yl}pyrimidine

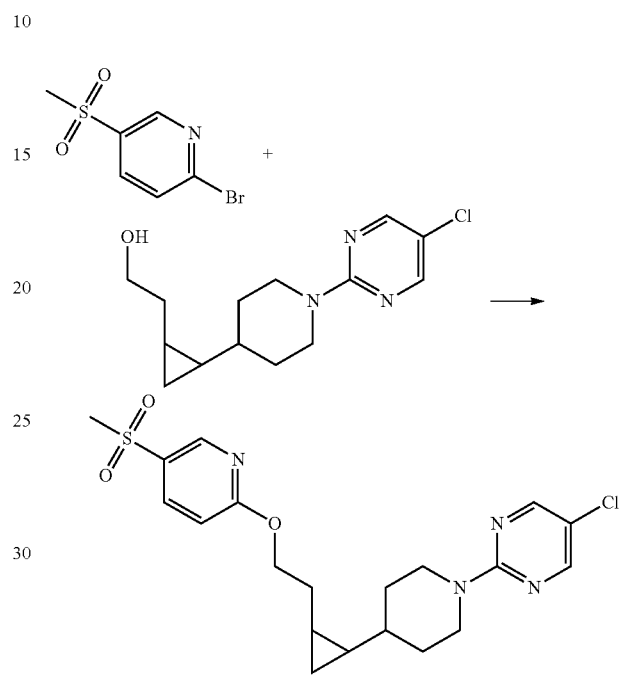

rac-cis-2-{2-[1-(5-Chloropyrimidin-2-yl)piperidin-4-yl]cyclopropyl}ethanol from step 2 of example 6 (338 mg, 1.2 mmol) was dissolved in DMF (0.7 ml, 0.38 M). NaI (60% in oil, 144 mg, 3.6 mmol) was added and the mixture was stirred for 10 min at RT. 2-Bromo-5-(methylsulfonyl)pyridine (340 mg, 1.44 mmol) was added and the mixture stirred at RT 2½ hours. The mixture was diluted with 75 ml water and extracted with iPrOAc (3×50 ml), adding brine to break the layers. Organic phases were combined, washed with brine, dried over $Na_2SO_4$, filtered and stripped. The product was purified by chromatography on $SiO_2$ (40 g) eluting with 40% EtOAc:Hexanes.

Material is further purified by RPHPLC. Elution gradient 10-100%:Water:Acetonitrile+0.1% TFA.

LRMS calc: 436.13; obs: 436.93 (M+1).

Example 6b

Preparation of 5-chloro-2-{-4-[(1R,2S)-2-(2-{[5-(methylsulfonyl)pyridin-2-yl]oxy}ethyl)cyclopropyl]piperidin-1-yl}pyrimidine

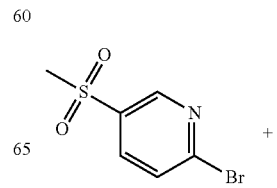

-continued

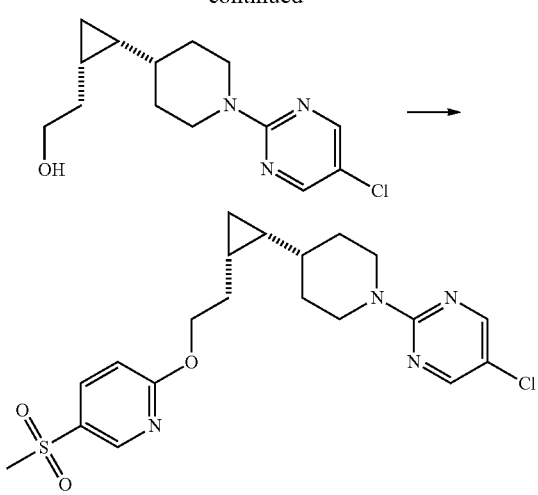

2-{(1S,2R)-2-[1-(S-chloropyrimidin-2-yl)piperidin-4-yl]cyclopropyl}ethanol from step 2b of example 6 (338 mg, 1.2 mmol) was dissolved in DMF (0.7 ml, 0.38 M). NaH (60% in oil, 144 mg, 3.6 mmol) was added and the mixture was stirred for 10 min at RT. 2-Bromo-5-(methylsulfonyl)pyridine (340 mg, 1.44 mmol) was added and the mixture stirred at RT 2½ hours. The mixture was diluted with 75 ml water and extracted with iPrOAc (3×50 ml), adding brine to break the layers. Organic phases were combined, washed with brine, dried over $Na_2SO_4$, filtered and stripped. The product was purified by chromatography on $SiO_2$ (40 g) eluting with 40% EtOAc:Hexanes. Material is further purified by RPHPLC. Elution gradient 10-100%:Water:Acetonitrile+0.1% TPA.

LRMS calc: 436.13; obs: 436.93 (M+1).

Compounds reported in Table 1 can be prepared by a general procedures analogous to those described in Examples 6 and 6a above. Analogs designated chiral are prepared from the single enantiomer of the alcohol of Example 6 Step 2 prepared from cis tert-butyl 4-[2-(2-hydroxyethyl)cyclopropyl]piperidine-1-carboxylate of Example 2 Step 4. Phenols which are not commercially available were prepared as described in Examples 56-81c below.

TABLE 1

| Examples | Chemical name | Chemical Structure | (M + 1) |
|---|---|---|---|
| Example 7 | rac cis-5-chloro-2-[4-(2-{2-[3-(methylsulfonyl)phenoxy]ethyl}cyclopropyl)piperidin-1-yl]pyrimidine | 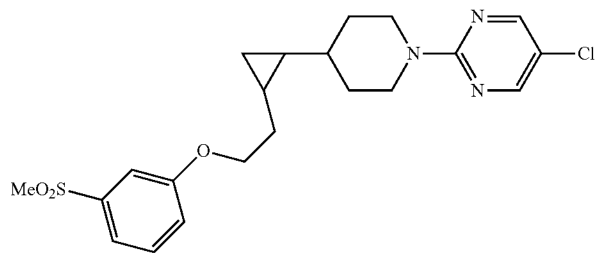 [SMILES: CS(=O)(=O)c1cccc(OCCC2CC2C2CCN(c3ncc(Cl)cn3)CC2)c1] | 436.16 |
| Example 8 | rac cis-5-chloro-2-[4-(2-{2-[3-(5-methyl-1,3,4-oxadiazol-2-yl)phenoxy]ethyl}cyclopropyl)piperidin-1-yl]pyrimidine | 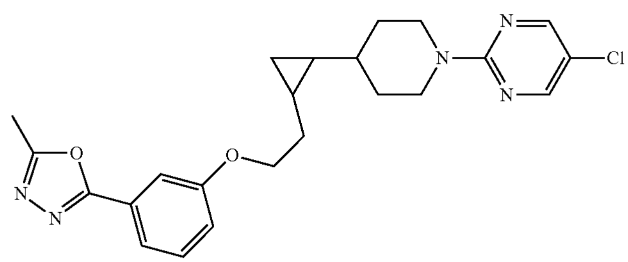 [SMILES: Cc1nnc(-c2cccc(OCCC3CC3C3CCN(c4ncc(Cl)cn4)CC3)c2)o1] | 440.63 |
| Example 9 | rac cis-5-chloro-2-[4-(2-{2-[3-(1H-1,2,4-triazol-1-yl)phenoxy]ethyl}cyclopropyl)piperidin-1-yl]pyrimidine | 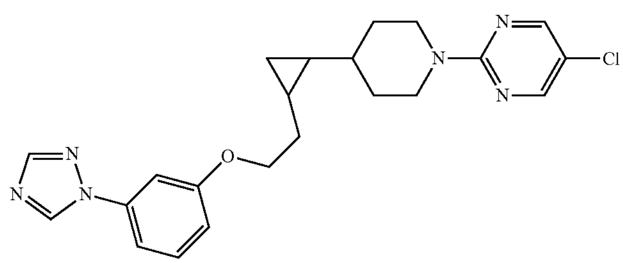 [SMILES: Clc1cnc(N2CCC(C3CC3CCOc3cccc(-n4cncn4)c3)CC2)nc1] | 425.2 |
| Example 10 | rac cis-5-chloro-2-[4-(2-{2-[3-(1,3,4-oxadiazol-2-yl)phenoxy]ethyl}cyclopropyl)piperidin-1-yl]pyrimidine | 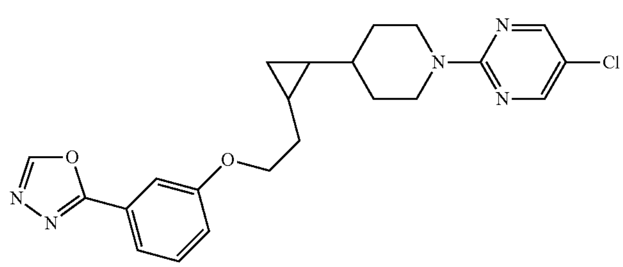 [SMILES: Clc1cnc(N2CCC(C3CC3CCOc3cccc(-c4nnco4)c3)CC2)nc1] | 424.61 |

TABLE 1-continued

| Examples | Chemical name | Chemical Structure | (M + 1) |
| --- | --- | --- | --- |
| Example 11 | rac cis-4-(2-{2-[1-(5-chloropyrimidin-2-yl)piperidin-4-yl]cyclopropyl}ethoxy)-N-cyclopropyl-2-fluorobenzamide | 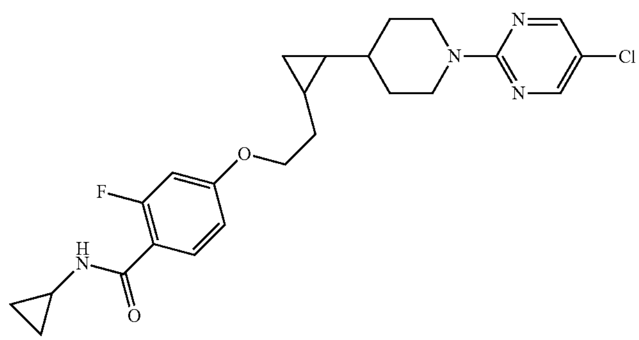 [SMILES: O=C(NC1CC1)c1ccc(OCCC2CC2C2CCN(c3ncc(Cl)cn3)CC2)cc1F] | 459.16 |
| Example 12 | rac cis-4-(2-{2-[1-(5-chloropyrimidin-2-yl)piperidin-4-yl]cyclopropyl}ethoxy)-2-fluorobenzonitrile | 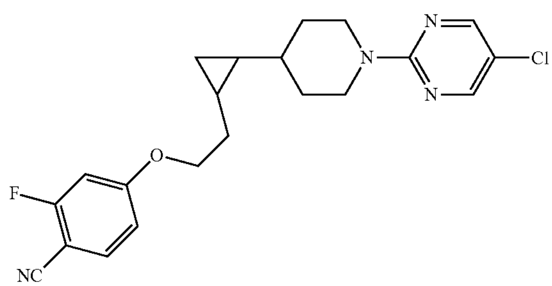 [SMILES: N#Cc1ccc(OCCC2CC2C2CCN(c3ncc(Cl)cn3)CC2)cc1F] | 401.58 |
| Example 13 | rac cis-5-chloro-2-[4-(2-{2-[4-(cyclopropylsulfonyl)phenoxy]ethyl}cyclopropyl)piperidin-1-yl]pyrimidine | 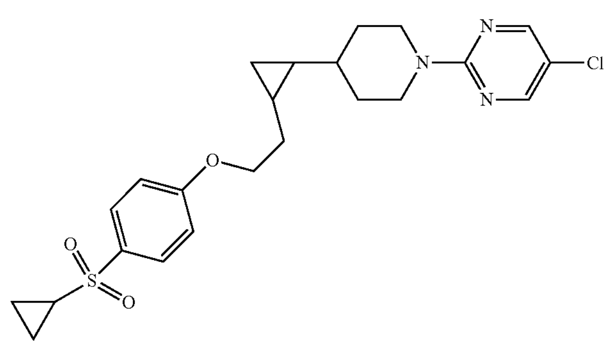 [SMILES: O=S(=O)(c1ccc(OCCC2CC2C2CCN(c3ncc(Cl)cn3)CC2)cc1)C1CC1] | 462.67 |
| Example 14 | rac cis-5-chloro-2-[4-(2-{2-[3-fluoro-4-(5-methy-1,3,4-oxadiaxol-2-yl)phenoxy]ethyl}cyclopropyl)piperidin-1-yl]pyrimidine | 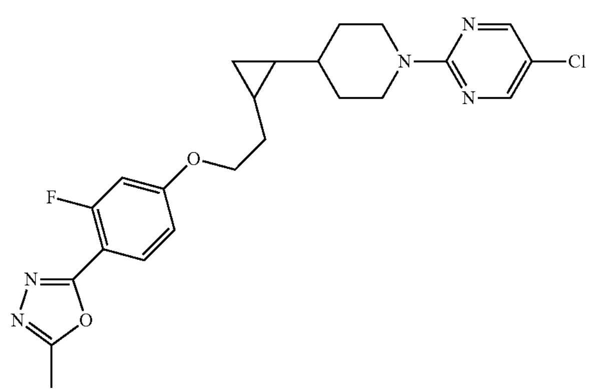 [SMILES: Cc1nnc(-c2ccc(OCCC3CC3C3CCN(c4ncc(Cl)cn4)CC3)cc2F)o1] | 458.63 |

TABLE 1-continued

| Examples | Chemical name | Chemical Structure | (M + 1) |
|---|---|---|---|
| Example 15 | rac cis-5-chloro-2-[4-(2-{2-[4-(1,3,4-oxadiazol-2-yl)phenoxy]ethyl}cyclopropyl)piperidin-1-yl]pyrimidine | 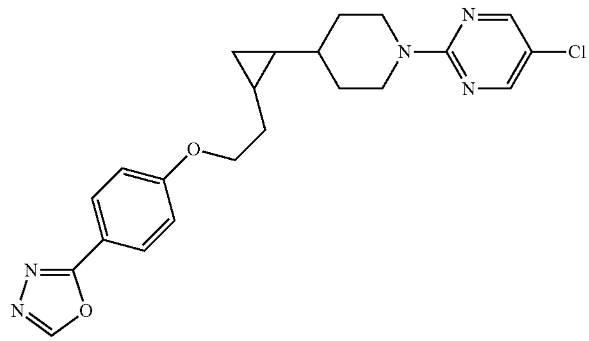 [SMILES: Clc1cnc(N2CCC(C3CC3CCOc3ccc(-c4nnco4)cc3)CC2)nc1] | 426.61 |
| Example 16 | rac cis-5-chloro-2-[4-(2-{2-[4-(5-methyl-1,3,4-oxadiazol-2-yl)phenoxy]ethyl}cyclopropyl)piperidin-1-yl]pyrimidine | 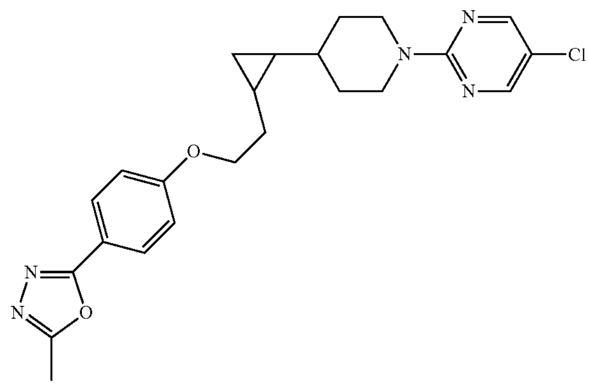 [SMILES: Cc1nnc(-c2ccc(OCCC3CC3C3CCN(c4ncc(Cl)cn4)CC3)cc2)o1] | 440.62 |
| Example 17 | rac cis-5-chloro-2-[4-(2-{2-[4-(1,2,4-oxadiazol-3-yl)phenoxy]ethyl}cyclopropyl)piperidin-1-yl]pyrimidine | 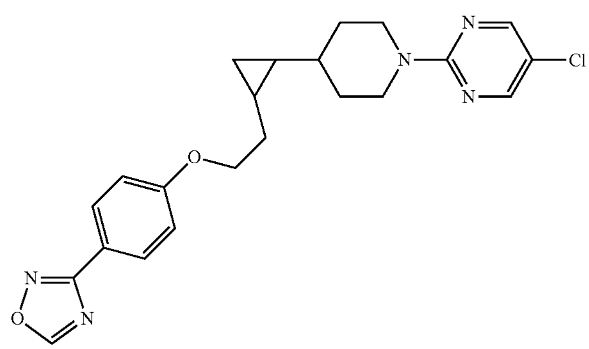 [SMILES: Clc1cnc(N2CCC(C3CC3CCOc3ccc(-c4ncon4)cc3)CC2)nc1] | 426.63 |
| Example 18 | rac cis-5-chloro-2-[4-(2-{2-[4-(1,2,4-oxadiazol-5-yl)phenoxy]ethy]}cyclopropyl)piperidin-1-yl]pyrimidine | 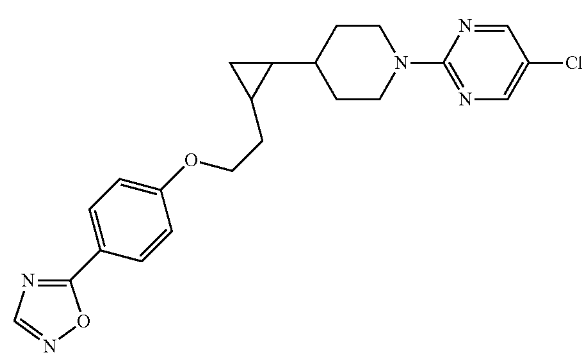 [SMILES: Clc1cnc(N2CCC(C3CC3CCOc3ccc(-c4ncno4)cc3)CC2)nc1] | 426.61 |

TABLE 1-continued

| Examples | Chemical name | Chemical Structure | (M + 1) |
| --- | --- | --- | --- |
| Example 19 | rac cis-5-chloro-2-[4-(2-{2-[4-(1,3-oxazol-4-yl)phenoxy]ethyl}cyclopropyl)piperidin-1-yl]pyrimidine | 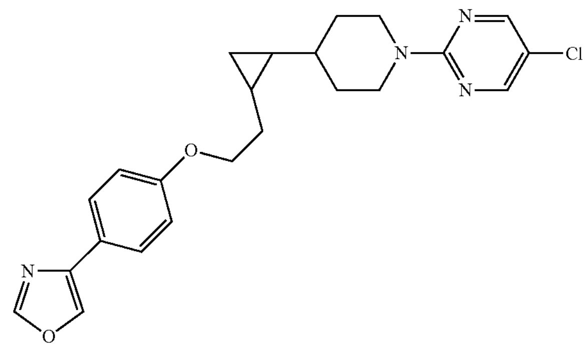 [SMILES: Clc1cnc(N2CCC(C3CC3CCOc3ccc(-c4cocn4)cc3)CC2)nc1] | 425.64 |
| Example 20 | rac cis-5-chloro-2-(4-{2-[2-(4-isoxazol-4-yl)phenoxy]ethyl]cyclopropyl}piperidin-1-yl)pyrimidine | 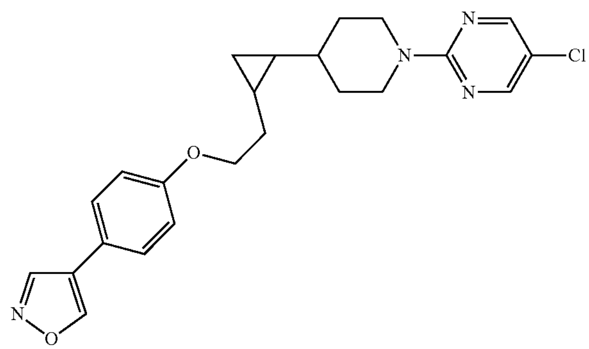 [SMILES: Clc1cnc(N2CCC(C3CC3CCOc3ccc(-c4cnoc4)cc3)CC2)nc1] | 425.15 |
| Example 21 | rac cis-5-chloro-2-(4-{2-[2-(4-isoxazol-5-yl)phenoxy]ethyl]cyclopropyl}piperidin-1-yl)pyrimidine | 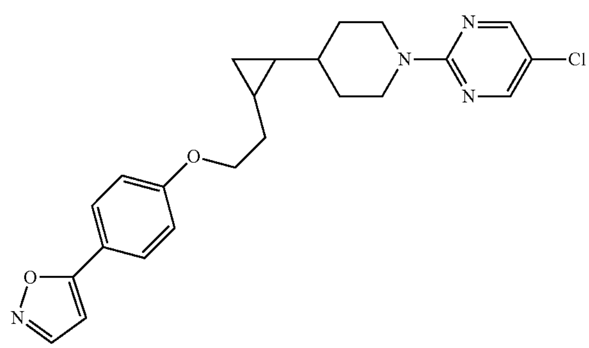 [SMILES: Clc1cnc(N2CCC(C3CC3CCOc3ccc(-c4ccno4)cc3)CC2)nc1] | 425.64 |
| Example 22 | rac cis-5-chloro-2-[4-(2-{2-[4-(1H-pyrazol-3-yl)phenoxy]ethyl}cyclopropyl)piperidin-1-yl]pyrimidine | 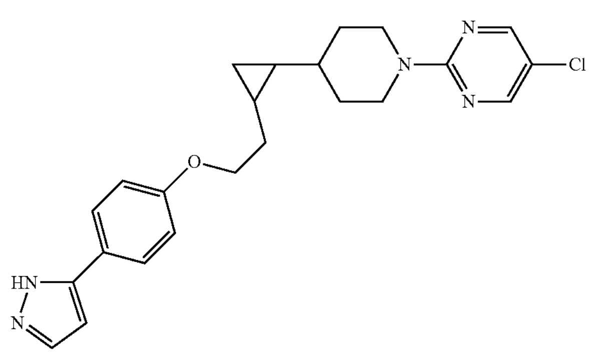 | 424.18 |

TABLE 1-continued

| Examples | Chemical name | Chemical Structure | (M + 1) |
|---|---|---|---|
| Example 23 | rac cis-5-chloro-2-[4-(2-{2-[4-(1H-pyrazol-4-yl)phenoxy]ethyl}cyclopropyl)piperidin-1-yl]pyrimidine | 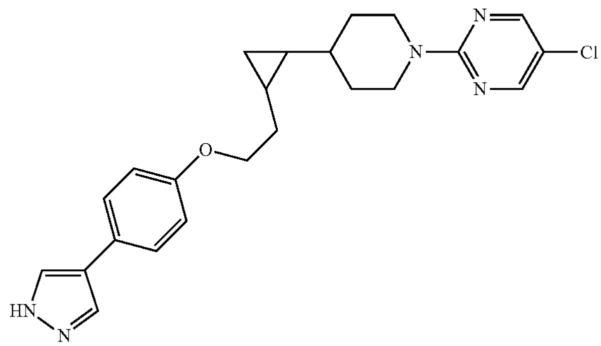 [SMILES: Clc1cnc(N2CCC(C3CC3CCOc3ccc(-c4cn[nH]c4)cc3)CC2)nc1] | 424.66 |
| Example 24 | rac cis-5-chloro-2-[4-(2-{2-[4-(1H-pyrazol-1-yl)phenoxy]ethyl}cyclopropyl)piperidin-1-yl]pyrimidine | 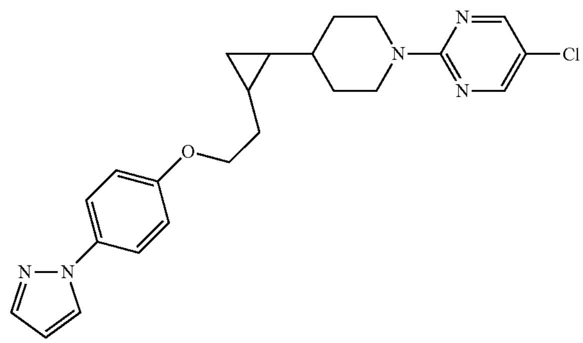 [SMILES: Clc1cnc(N2CCC(C3CC3CCOc3ccc(-n4cccn4)cc3)CC2)nc1] | 424.59 |
| Example 25 | rac cis-5-chloro-2-[4-(2-{2-[4-(1H-1,2,4-triazol-1-yl)phenoxy]ethyl}cyclopropyl)piperidin-1-yl]pyrimidine | 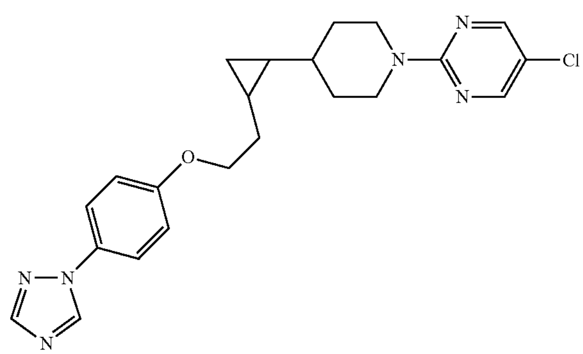 [SMILES: Clc1cnc(N2CCC(C3CC3CCOc3ccc(-n4cncn4)cc3)CC2)nc1] | 425.6 |
| Example 26 | rac cis-5-chloro-2-[4-(2-{2-[4-(4H-1,2,4-triazol-4-yl)phenoxy]ethyl}cyclopropyl)piperidin-1-yl]pyrimidine | 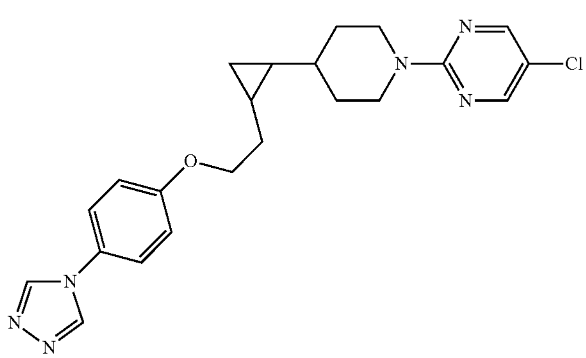 [SMILES: Clc1cnc(N2CCC(C3CC3CCOc3ccc(-n4cnnc4)cc3)CC2)nc1] | 425.64 |

TABLE 1-continued

| Examples | Chemical name | Chemical Structure | (M + 1) |
|---|---|---|---|
| Example 27 | rac cis-5-chloro-2-[4-(2-{2-[4-(1H-1,2,3-triazol-1-yl)phenoxy]ethyl}cyclopropyl)piperidin-1-yl]pyrimidine | 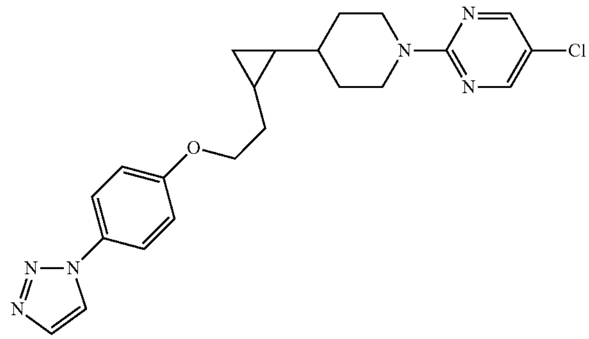 [SMILES: Clc1cnc(N2CCC(C3CC3CCOc3ccc(-n4ccnn4)cc3)CC2)nc1] | 425.21 |
| Example 27b | rac-cis-5-fluoro-2-[4-(2-{2-[4-(1H-1,2,3-triazol-1-yl)phenoxy]ethyl}cyclopropyl)piperidin-1-yl]pyrimidine | 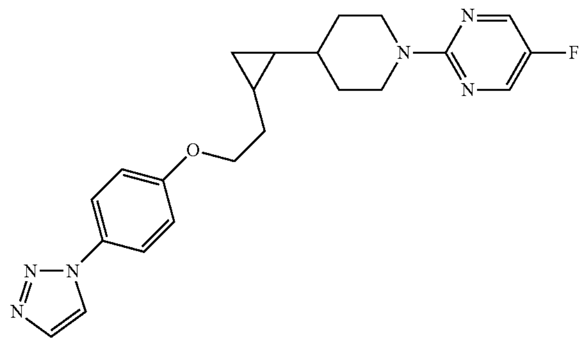 [SMILES: Fc1cnc(N2CCC(C3CC3CCOc3ccc(-n4ccnn4)cc3)CC2)nc1] | 408.9 |
| Example 27c | rac cis-5-methyl-2-[4-(2-{2-[4-(1H-1,2,3-triazol-1-yl)phenoxy]ethyl}cyclopropyl)piperidin-1-yl]pyrimidine | 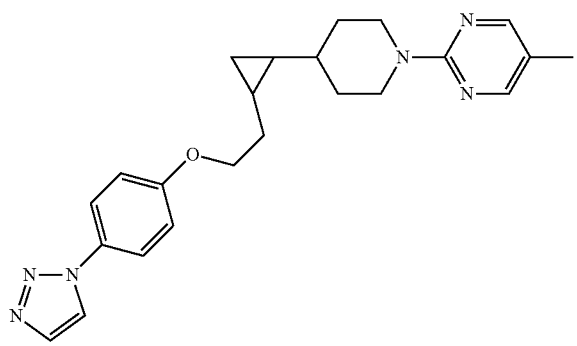 [SMILES: Cc1cnc(N2CCC(C3CC3CCOc3ccc(-n4ccnn4)cc3)CC2)nc1] | 405.2 |
| Example 28 | rac cis-5-chloro-2-[4-(2-{2-[4-(2H-1,2,3-triazol-2-yl)phenoxy]ethyl}cyclopropyl)piperidin-1-yl]pyrimidine | 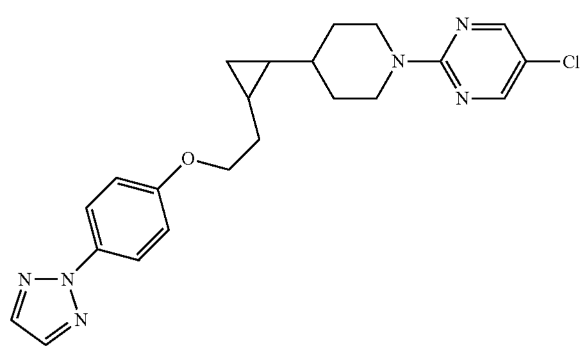 [SMILES: Clc1cnc(N2CCC(C3CC3CCOc3ccc(-n4nccn4)cc3)CC2)nc1] | 425.64 |

TABLE 1-continued

| Examples | Chemical name | Chemical Structure | (M + 1) |
| --- | --- | --- | --- |
| Example 29 | rac cis-5-chloro-2-[4-(2-{2-[4-(1H-1,2,3-triazol-5-yl)phenoxy]ethyl}cyclopropyl)piperidin-1-yl]pyrimidine | 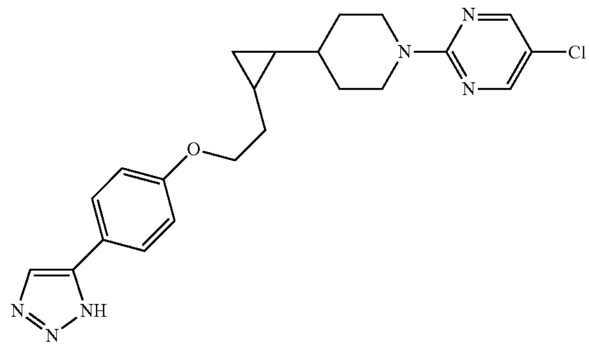 [SMILES: Clc1cnc(N2CCC(C3CC3CCOc3ccc(-c4cnn[nH]4)cc3)CC2)nc1] | 425.64 |
| Example 30 | rac cis-5-chloro-2-[4-(2-{2-[4-(1H-tetrazol-1-yl)phenoxy]ethyl}cyclopropyl)piperidin-1-yl]pyrimidine | 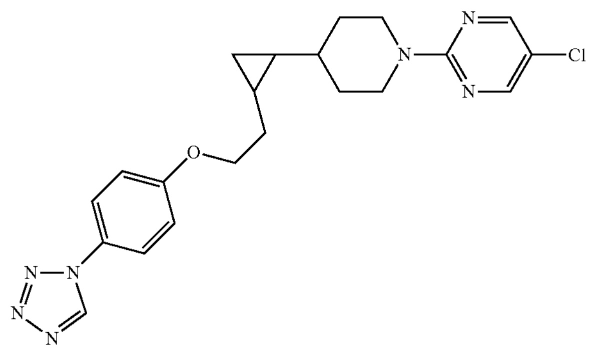 [SMILES: Clc1cnc(N2CCC(C3CC3CCOc3ccc(-n4cnnn4)cc3)CC2)nc1] | 426.6 |
| Example 30b | rac cis-5-chloro-2-[4-(2-{2-[3-fluoro-4-(1H-tetrazol-1-yl)phenoxy]ethyl}cyclopropyl)piperidin-1-yl]pyrimidine | 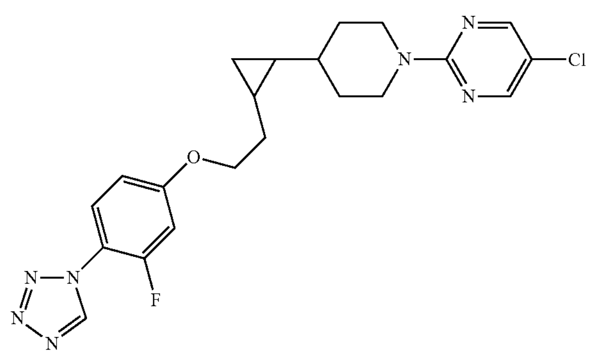 [SMILES: Fc1cc(OCCC2CC2C2CCN(c3ncc(Cl)cn3)CC2)ccc1-n1cnnn1] | 444.0 |
| Example 30d | rac cis-5-chloro-2-[4-(2-{2-[3-fluoro-4-(1H-tetrazol-1-yl)phenoxy]ethyl}cyclopropyl)piperidin-1-yl]pyrimidine | 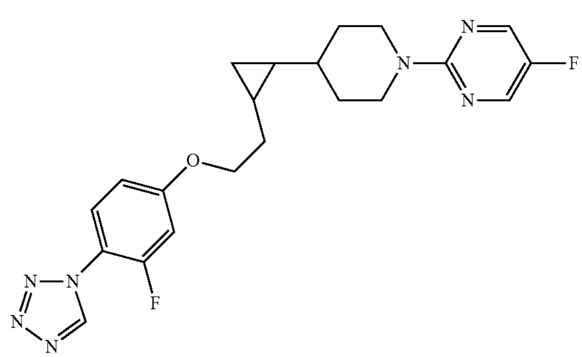 [SMILES: Fc1cnc(N2CCC(C3CC3CCOc3ccc(-n4cnnn4)c(F)c3)CC2)nc1] | 428.1 |

TABLE 1-continued

| Examples | Chemical name | Chemical Structure | (M + 1) |
|---|---|---|---|
| Example 30e | rac cis-2-[4-(2-{2-[3-fluoro-4-(1H-tetrazol-1-yl)phenoxy]ethyl)cyclopropyl)piperidin-1-yl]-5-methylpyrimidine | 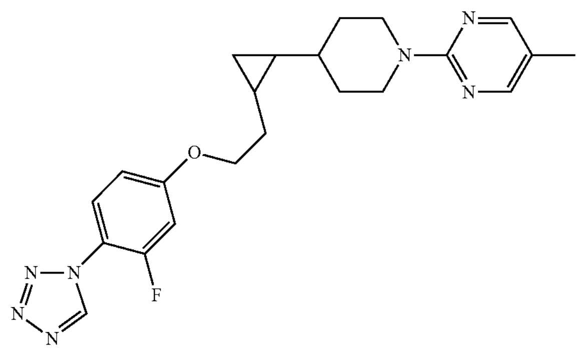 [SMILES: Cc1cnc(N2CCC(C3CC3CCOc3ccc(-n4cnnn4)c(F)c3)CC2)nc1] | 424.1 |
| Example 31 | rac cis-5-chloro-2-[4-(2-{2-[4-(2H-tetrazol-2-yl)phenoxy]ethyl}cyclopropyl)piperidin-1-yl]pyrimidine | 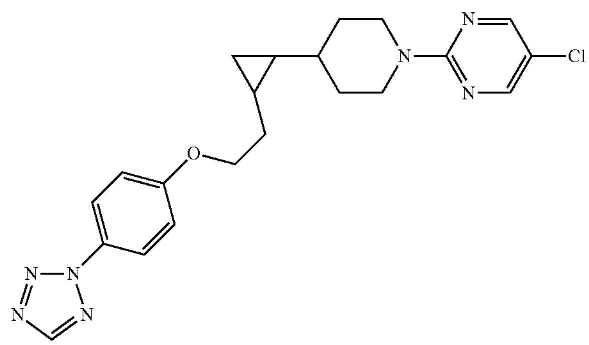 | 426.5 |
| Example 31a | rac cis-5-chloro-2-[4-(2-{2-[4-(5-methyl-2H-tetrazol-2-yl)phenoxy]ethyl}cyclopropyl)piperidin-1-yl]pyrimidine | 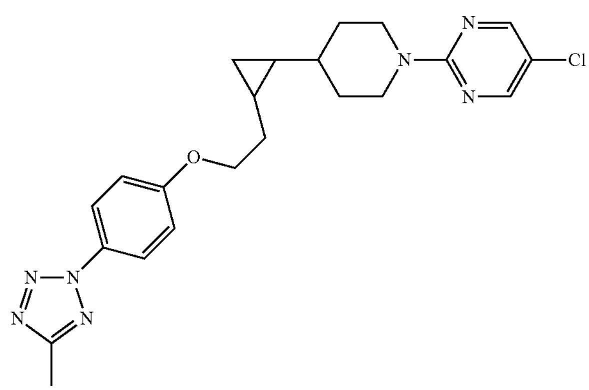 [SMILES: Cc1nnn(-c2ccc(OCCC3CC3C3CCN(c4ncc(Cl)cn4)CC3)cc2)n1] | 440.0 |
| Example 31b | rac cis-5-chloro-2-[4-(2-{2-[4-(5-methyl-1H-tetrazol-1-yl)phenoxy]ethyl}cyclopropyl)piperidin-1-yl]pyrimidine | 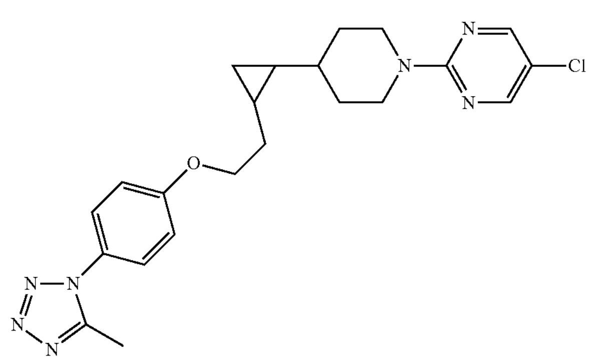 [SMILES: Cc1nnnn1-c1ccc(OCCC2CC2C2CCN(c3ncc(Cl)cn3)CC2)cc1] | 440.0 |

TABLE 1-continued

| Examples | Chemical name | Chemical Structure | (M + 1) |
|---|---|---|---|
| Example 32 | rac cis-5-chloro-2-[4-(2-{2-[3-fluoro-4-(5-methyl-1,3,4-oxadiazol-2-yl)phenoxy]ethyl}cyclopropyl)piperidin-1-yl]pyrimidine | 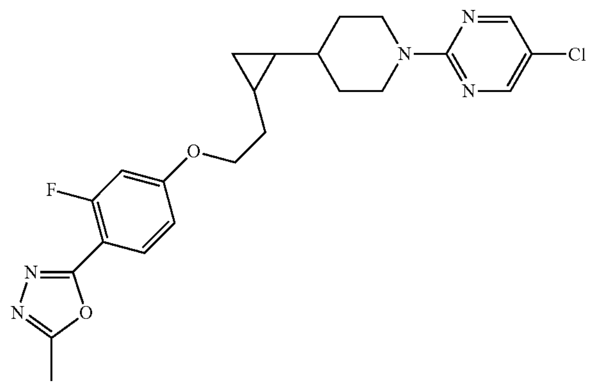 [SMILES: Cc1nnc(-c2ccc(OCCC3CC3C3CCN(c4ncc(Cl)cn4)CC3)cc2F)o1] | 458.63 |
| Example 33 | Chiral-cis-5-chloro-2-[4-(2-{2-[4-(methylsulfinyl)phenoxy]ethyl}cyclopropyl)piperidin-1-yl]pyrimidine | 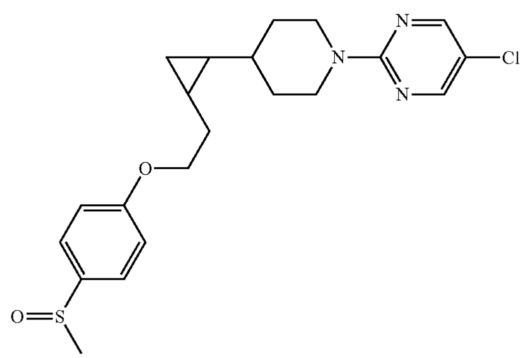 | 420.60 |
| Example 34 | Chiral-cis-6-(2-{2-[1-(5-chloropyrimidin-2-yl)piperidin-4-yl]cyclopropyl}ethoxy)-2-methylpyrimidine-4-carbonitrile | 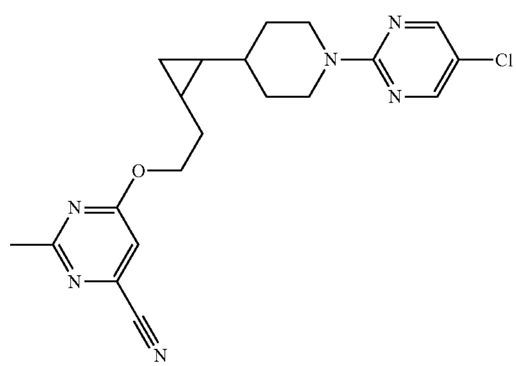 [SMILES: Cc1nc(C#N)cc(OCCC2CC2C2CCN(c3ncc(Cl)cn3)CC2)n1] | 399.60 |
| Example 35 | Rac-cis-1-[4-(2-{2[1-(5-chloropyrimidin-2-yl)piperidin-4-yl]cyclopropyl}ethoxy)phenyl]ethanone | 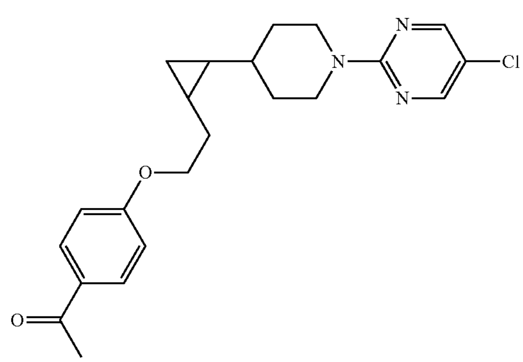 [SMILES: CC(=O)c1ccc(OCCC2CC2C2CCN(c3ncc(Cl)cn3)CC2)cc1] | 400.63 |

TABLE 1-continued

| Examples | Chemical name | Chemical Structure | (M + 1) |
|---|---|---|---|
| Example 36 | Rac-cis-2-methyl-6-(2-{2-[1-(5-methylpyrazin-2-yl)piperidin-4-yl]cyclopropyl}ethoxy)pyrimidine-4-carbonitrile | 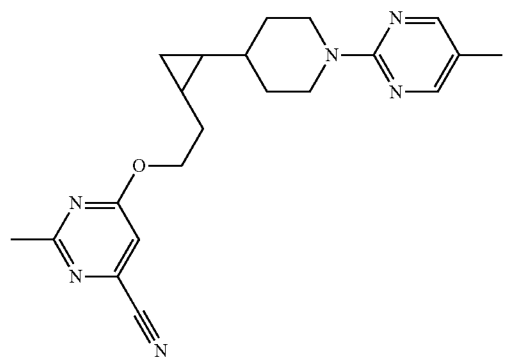 | 379.71 |
| Example 37 | Rac-cis-6-(2-{2-[1-(5-chloropyrimidin-2-yl)piperidin-4-yl]cyclopropyl}ethoxy)pyrimidine-4-carbonitrile | 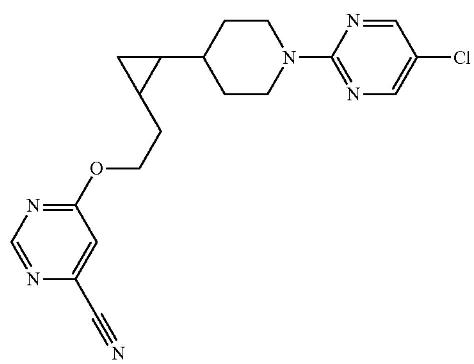 [SMILES: N#Cc1cc(OCCC2CC2C2CCN(c3ncc(Cl)cn3)CC2)ncn1] | 385.63 |
| Example 38 | Rac-cis-4-(2-{2-[1-(5-chloropyrimidin-2-yl)piperidin-4-yl]cyclopropyl}ethoxy)pyrimidine-2-carbonitrile | 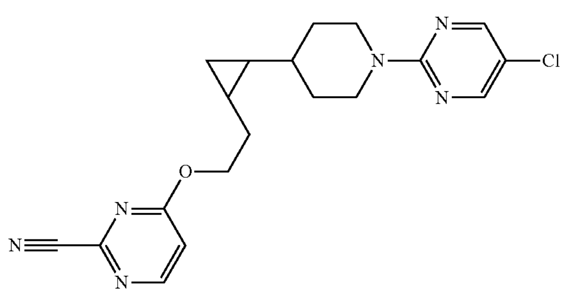 [SMILES: N#Cc1nccc(OCCC2CC2C2CCN(c3ncc(Cl)cn3)CC2)n1] | 385.63 |
| Example 39 | Chiral-cis-2-methyl-6-(2-{2-[1-(5-methylpyrimidin-2-yl)piperidin-4-yl]cyclopropyl}ethoxy)pyrimidine-4-carbonitrile | 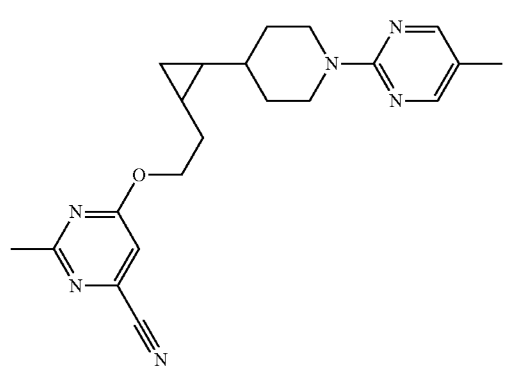 | 379.71 |

TABLE 1-continued

| Examples | Chemical name | Chemical Structure | (M + 1) |
| --- | --- | --- | --- |
| Example 40 | Rac-cis-2-methyl-6-(2-{2-[1-(5-methylpyrimidin-2-yl)piperidin-4-yl]cyclopropyl}ethoxy)pyrimidine-4-carbonitrile | 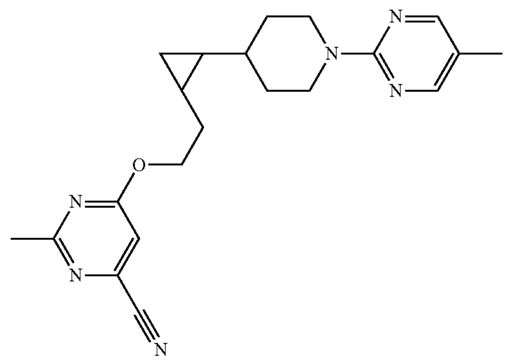 | 379.22 |
| Example 41 | Rac-cis-2,4-dimethyl-6-(2-{2-[1-(5-methylpyrimidin-2-yl)piperidin-4-yl]cyclopropyl}ethoxy)pyrimidine | 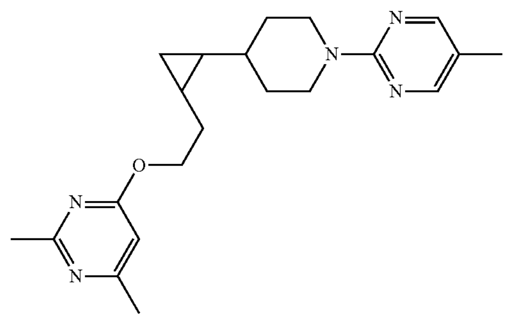 | 368.67 |
| Example 42 | Rac-cis-6-(2-{2-[1-(5-chloro-4-methylpyrimidin-2-yl)piperidin-4-yl]cyclopropyl}ethoxy)-2-methylpyrimidine-4-carbonitrile | 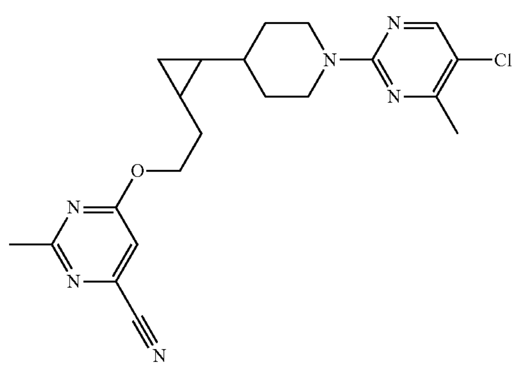 [SMILES: Cc1nc(C#N)cc(OCCC2CC2C2CCN(c3ncc(Cl)c(C)n3)CC2)n1] | 413.17 |
| Example 43 | Rac-cis-6-(2-{2-[1-(5-chloropyridin-2-yl)piperidin-4-yl]cyclopropyl}ethoxy)-2-methylpyrimidine-4-carbonitrile | 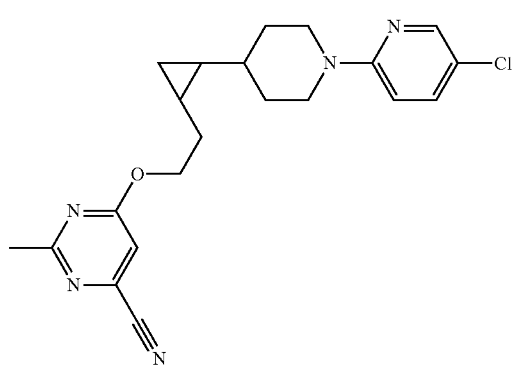 [SMILES: Cc1nc(C#N)cc(OCCC2CC2C2CCN(c3ccc(Cl)cn3)CC2)n1] | 398.58 |

TABLE 1-continued

| Examples | Chemical name | Chemical Structure | (M + 1) |
| --- | --- | --- | --- |
| Example 44 | Rac-cis-6-(2-{2-[1-(4,5-dimethylpyrimidin-2-yl)piperidin-4-yl]cyclopropyl}ethoxy)-2-methylpyrimidine-4-carbonitrile | 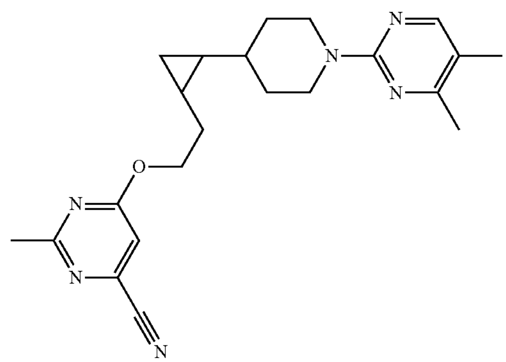 | 393.64 |
| Example 45 | Rac-cis-6-(2-{2-[1-(5-chloro-4-methylpyridin-2-yl)piperidin-4-yl]cyclopropyl}ethoxy)-2-methylpyrimidine-4-carbonitrile | 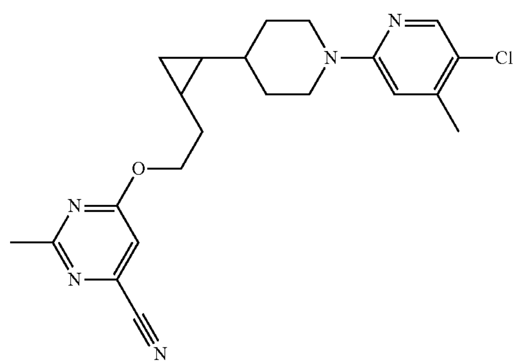 | 412.11 |
| Example 46 | Rac-cis-6-(2-{2-[1-(5-fluoro-4-methylpyrimidin-2-yl)piperidin-4-yl]cyclopropyl}ethoxy)-2-methylpyrimidine-4-carbonitrile | 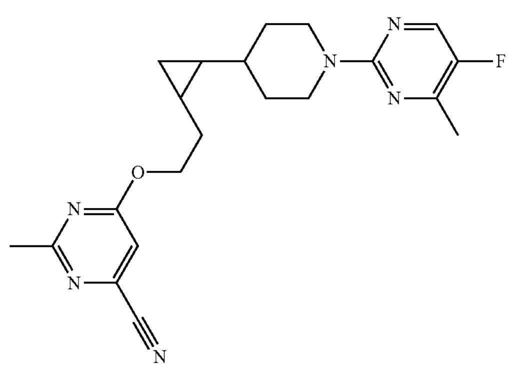 | 397.13 |
| Example 47 | Rac-cis-2-methyl-6-[2-(2-{1-[5-(trifluoromethyl)pyridin-2-yl]piperidin-4-yl}cyclopropyl)ethoxy]pyrimidine-4-carbonitrile | 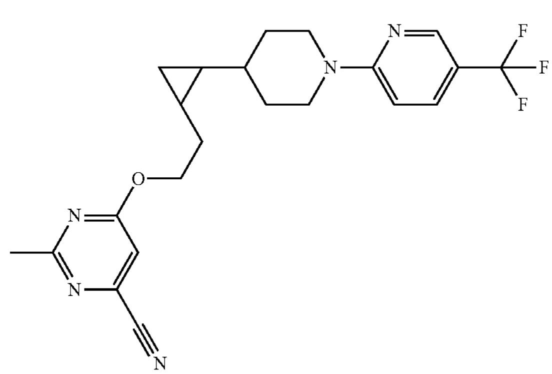 [SMILES: Cc1nc(C#N)cc(OCCC2CC2C2CCN(c3ccc(C(F)(F)F)cn3)CC2)n1] | 432.65 |

TABLE 1-continued

| Examples | Chemical name | Chemical Structure | (M + 1) |
| --- | --- | --- | --- |
| Example 48 | Rac-cis-5-chloro-2-(4-{2-[2-(pyridin-3-yloxy)ethyl]cyclopropyl}piperidin-1-yl)pyrimidine | 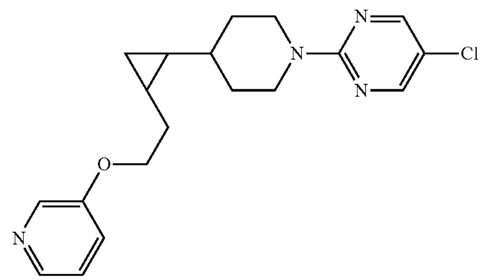 [SMILES: Clc1cnc(N2CCC(C3CC3CCOc3cccnc3)CC2)nc1] | 359.60 |
| Example 49 | Rac-cis-5-chloro-2-(4-{2-[2-(pyrimidin-4-yloxy)ethyl]cyclopropyl}piperidin-1-yl)pyrimidine | 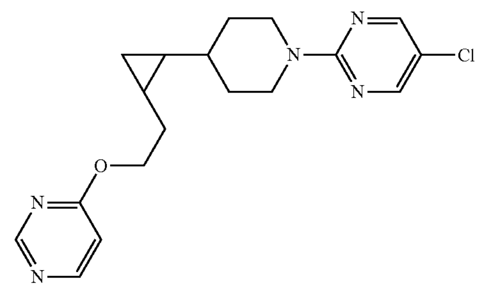 | 360.59 |
| Example 50 | Rac-cis-5-(2-{2-[1-(5-chloropyrimidin-2-yl)piperidin-4-yl]cyclopropyl}ethoxy)nicotinonitrile | 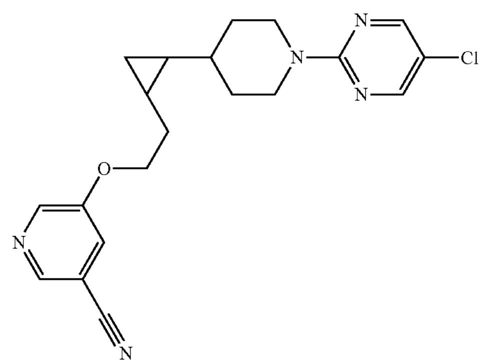 [SMILES: N#Cc1cncc(OCCC2CC2C2CCN(c3ncc(Cl)cn3)CC2)c1] | 384.57 |
| Example 51 | Rac-cis-6-(2-{2-[1-(5-chloropyrimidin-2-yl)piperidin-4-yl]cyclopropyl}ethoxy)-2-methylpyrimidine-4-carbonitrile | 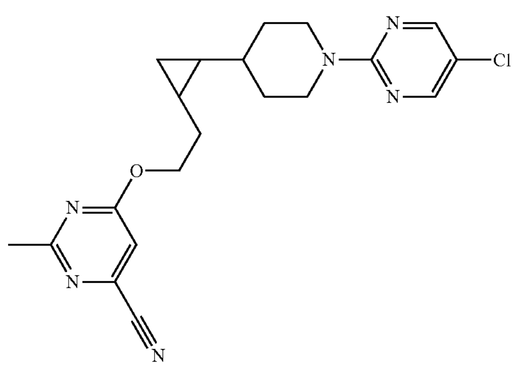 [SMILES: Cc1nc(C#N)cc(OCCC2CC2C2CCN(c3ncc(Cl)cn3)CC2)n1] | 399.59 |
| Example 52 | Rac-cis-4-(2-{2-[1-(5-chloropyrimidin-2-yl)piperidin-4-yl]cyclopropyl}ethoxy)-6-methylpyrimidine-2-carbonitrile | 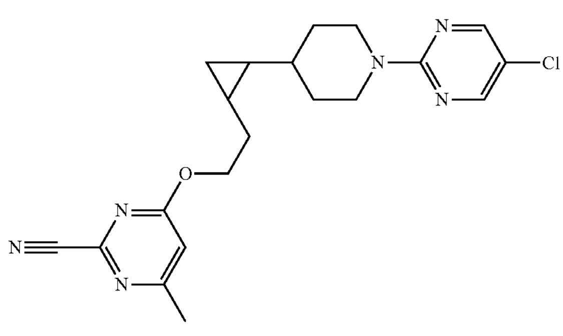 [SMILES: Cc1cc(OCCC2CC2C2CCN(c3ncc(Cl)cn3)CC2)nc(C#N)n1] | 399.58 |

TABLE 1-continued

| Examples | Chemical name | Chemical Structure | (M + 1) |
| --- | --- | --- | --- |
| Example 53 | Rac-cis-6-(2-{2-[1-(5-fluoropyrimidin-2-yl)piperidin-4-yl]cyclopropyl}ethoxy)-2-methylpyrimidine-4-carbonitrile | 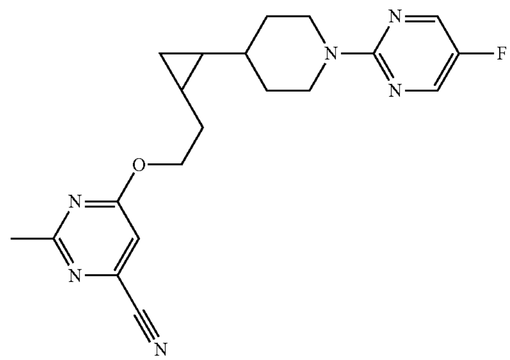 [SMILES: Cc1nc(C#N)cc(OCCC2CC2C2CCN(c3ncc(F)cn3)CC2)n1] | 383.65 |
| Example 54 | Rac-cis-5-(2-{2-[1-(5-chloropyrimidin-2-yl)piperidin-4-yl]cyclopropyl}ethoxy)pyridine-2-carbonitrile | 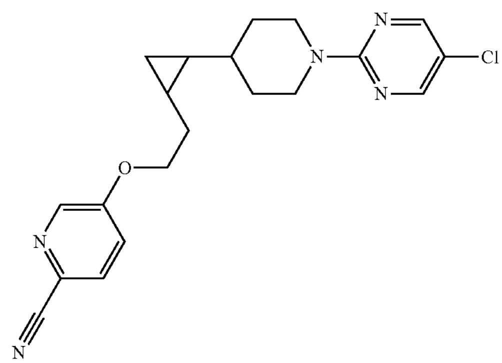 [SMILES: N#Cc1ccc(OCCC2CC2C2CCN(c3ncc(Cl)cn3)CC2)cn1] | 384.10 |
| Example 55 | Rac-cis-5-chloro-2-(4-{2-[2-(pyridin-4-yloxy)ethyl]cyclopropyl}piperidin-1-yl)pyrimidine | 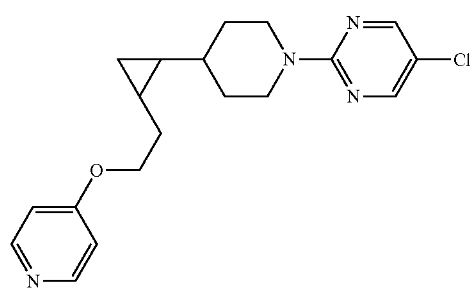 [SMILES: Clc1cnc(N2CCC(C3CC3CCOc3ccncc3)CC2)nc1] | 359.54 |
| Example 55a | Chiral cis-5-chloro-2-{4-[2-(2-{[5-(1H-1,2,3-triazol-1-yl)pyridin-2-yl]oxy}ethyl)cyclopropyl]piperidin-1-yl}pyrimidine | 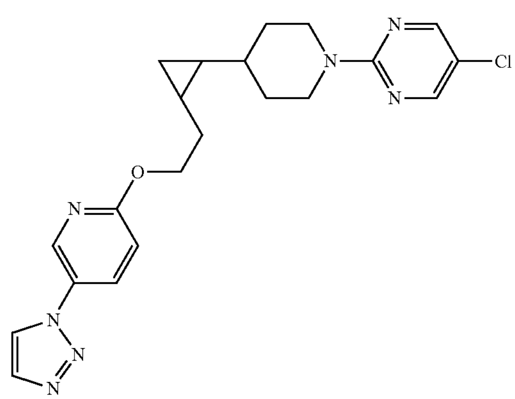 [SMILES: Clc1cnc(N2CCC(C3CC3CCOc3ccc(-n4ccnn4)cn3)CC2)nc1] | 426.14 |

Preparations of non-commercial phenol starting materials for examples in Table I are reported below.

Preparative Example 56

Preparation of 3-(methylsulfonyl)phenol

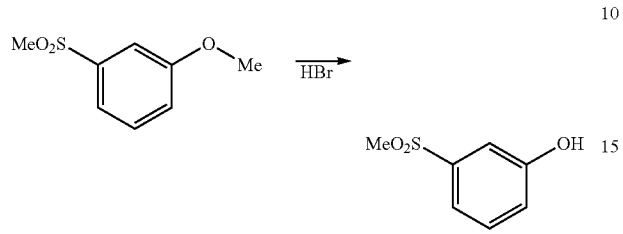

1-Methoxy-3-(methylsulfonyl)benzene (300 mg, 1.61 mmol) was suspended in 1.6 mL aqueous hydrobromic acid (48% w/w) and 1.6 mL acetic acid. The mixture was heated under reflux for 24 hours. The reaction was cooled back to room temperature and concentrated. The residue was purified by column chromatography through a 40 gram biotage silica gel cartridge eluting with 40-70% ethyl acetate/hexanes (gradient) to give the product as white solid. LRMS calc: 172.0; obs: 173.2 (M+1).

The following phenols were prepared similarly:

Preparative Example 57

Preparation of 3-(1,3,4-oxadiazol-2-yl)phenol

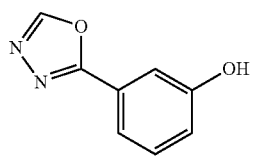 [SMILES: Oc1cccc(-c2nnco2)c1]

The target phenol was synthesized by a procedure analogous to Example 56 from commercially available 2-(3-methoxyphenyl)-1,3,4-oxadiazole.

Preparative Example 58

Preparation of 4-(1,3-oxazol-4-yl)phenol

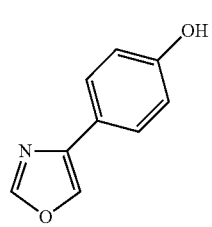 [SMILES: Oc1ccc(-c2cocn2)cc1]

The target phenol was synthesized by a procedure analogous to Example 56 from commercially available 4-(4-methoxyphenyl)-1,3-oxazole.

Preparative Example 59

Preparation of 4-(1H-pyrazol-5-yl)phenol

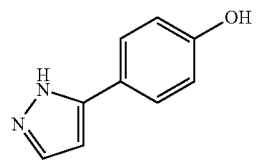 [SMILES: Oc1ccc(-c2ccn[nH]2)cc1]

The target phenol was synthesized by a procedure analogous to Example 56 from commercially available 5-(4-methoxyphenyl)-1H-pyrazole.

Preparative Example 60

Preparation of 4-(1H-pyrazol-1-yl)phenol

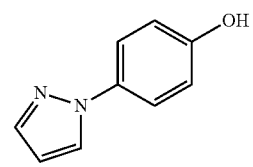 [SMILES: Oc1ccc(-n2cccn2)cc1]

The target phenol was synthesized by a procedure analogous to Example 56 from commercially available 1-(4-methoxyphenyl)-1H-pyrazole.

Preparative Example 61

Preparation of 3-(methylsulfonyl)phenol

Step 1: 2-{3-[(4-methoxybenzyl)oxy]phenyl}-5-methyl-1,3,4-oxadiazole

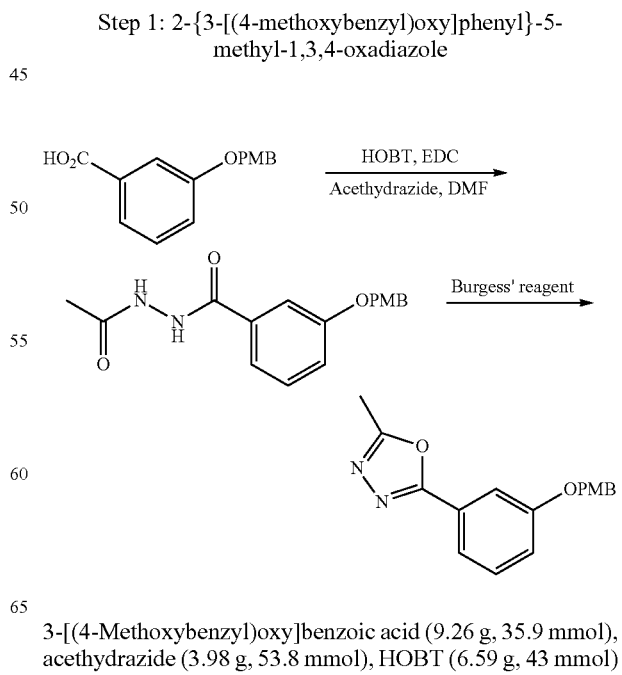

3-[(4-Methoxybenzyl)oxy]benzoic acid (9.26 g, 35.9 mmol), acethydrazide (3.98 g, 53.8 mmol), HOBT (6.59 g, 43 mmol)

and EDC (10.3 g, 53.8 mmol) were weighed into a 200 mL RB flask. DMF (60 mL) was added. The mixture was stirred vigorously at room temperature. The solid dissolved within 5 min. LC-MS showed complete consumption of the acid after 30 min. DMF was removed at 60° C. under vacuum. The residue was treated with 100 mL EtOAc/water (1/1) and was allowed to stand overnight. The solid was collected via filtration and washed with EtOAc. The crude N'-acetyl-3-[(4-methoxybenzyl)oxy]benzohydrazide (8 g) was suspended in 100 mL THF and was heated under reflux in the presence of Burgess' reagent (12.8 g, 53.8 mmol) for 1 hour. The solution was cooled and directly passed through a plug of silica gel (300 gram) which was washed thoroughly with 20% acetone/hexanes. The eluent was concentrated to give the crude product as white solid.

Step 2: 3-(5-methyl-1,3,4-oxadiazol-2-yl)phenol

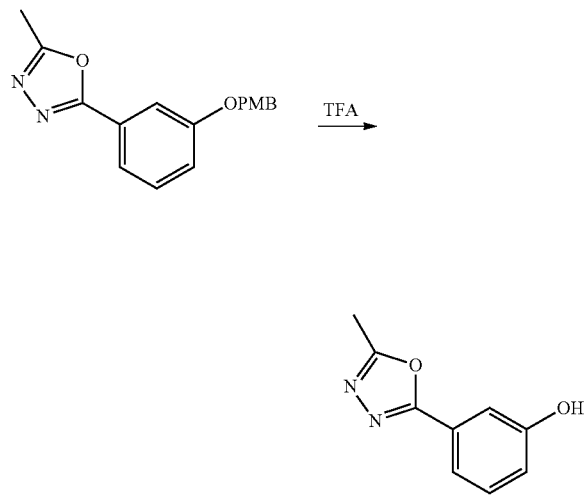

2-{3-[(4-Methoxybenzyl)oxy]phenyl}-5-methyl-1,3,4-oxadiazole (100 mg, 0.338 mmol) was treated with 0.5 mL TFA and was stirred at room temperature for 10 min. Excess TFA was removed under vacuum and the residue was purified by column chromatography using a 24 gram biotage silica gel cartridge eluting with 20-50% ethyl acetate/hexanes (gradient) to give the product as white solid. LRMS calc: 176.1; obs: 177.2 (M+1).

Preparative Example 62

Preparation of 3-fluoro-4-(5-methyl-1,3,4-oxadiazol-2-yl)phenol

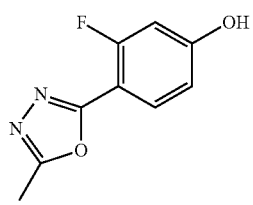

The title phenol was prepared from 4-[(4-Methoxybenzyl)oxy]benzoic acid by a protocol analogous to that of Example 61.

Preparative Example 63

Preparation of 3-(1H-1,2,4-triazol-1-yl)phenol

Step 1: 1-[3-(benzyloxy)phenyl]-1H-1,2,4-triazole

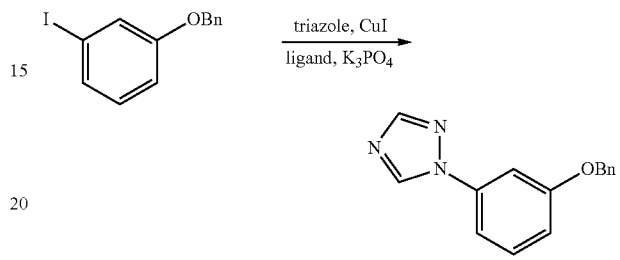

To a sealable pressure tube, were added CuI (31 mg, 0.16 mmol), 1H-1,2,4-triazole (245 mg, 3.55 mmol), Potassium phosphate (1.37 g, 6.45 mmol), 1-(benzyloxy)-3-iodobenzene (1 g, 3.22 mmol), and a stir bar. The reaction vessel was fitted with a rubber septum, evacuated and back-filled with argon, and this sequence was repeated. DMF (3.22 mmol) and N,N'-dimethylethylene diamine (28 mg, 0.322 mmol) were then added successively under a stream of argon. The reaction tube was crimp sealed with a fresh PTFE septum (caution: build-up of pressure possible; use a safety shield) and immersed in a preheated oil bath at 110° C. for 24 h with magnetic stirring. The reaction mixture was removed from heating, allowed to attain ambient temperature, diluted with ethyl acetate (2-3 mL), filtered through a plug of silica gel, and eluted with additional ethyl acetate (10-20 mL). The filtrate was concentrated and the resulting residue was purified by chromatography on silica gel (80 gram biotage silica gel cartridge, 40-60% EtOAc hexanes) to provide the desired product as white solid. LRMS calc: 251.3; obs: 252.4 (M+1).

Step 2: 3-(1H-1,2,4-triazol-1-yl)phenol

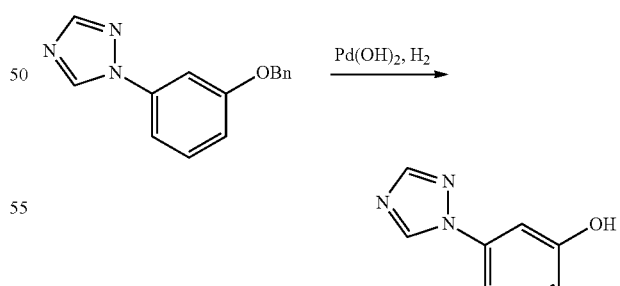

1-[3-(benzyloxy)phenyl]-1H-1,2,4-triazole (250 mg, 0.995 mmol) was dissolved in 5 mL methanol. The solution was degassed and backfilled with nitrogen. Palladium on carbon (10% w/w, 106 mg, 0.1 mmol) was then added. The reaction vessel was degassed and backfilled with hydrogen 3 times and stirred under a hydrogen balloon at room temperature. The reaction was stirred overnight. It was then diluted with 5 mL acetone and filtered through a plug of silica gel (5 g), which was washed thoroughly with acetone. Concentration afforded the product as white solid. LRMS calc: 161.1; obs: 162.2 (M+1).

Preparative Example 64

Preparation of 4-(cyclopropylsulfonyl)phenol

Step 1: 1-(cyclopropylthio)-4-methoxybenzene

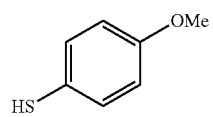 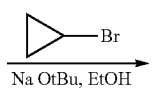

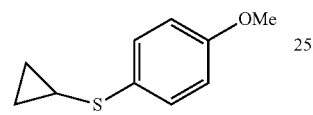

To a solution of sodium t-butoxide (317 mg, 3.3 mmol) in 15 mL EtOH at 0° C. was slowly added 4-methoxybenzenethiol (420 mg, 3 mmol). After completion of addition, the reaction was stirred at RT for 1 hour before cooling down to 0° C. Bromocyclopropane (417 mg, 3.45 mmol) was added slowly, and the mixture was brought to reflux for one hour, cooled and concentrated. Water (1 mL) was added and the mixture was extract with ethyl acetate. The organic phases were dried and purified by column chromatography eluting with 20% ethyl acetate/hexanes to give the desired product.

Step 2: 1-(cyclopropylsulfonyl)-4-methoxybenzene

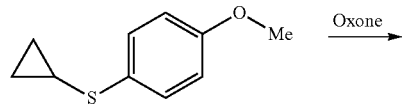

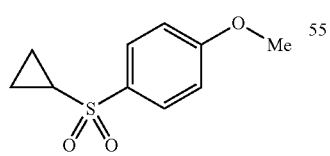

1-(cyclopropylthio)-4-methoxybenzene (300 mg, 1.66 mmol) was dissolved in 8 mL MeOH and Water (1:1). Oxone (4.9 g, 6.66 mmol) was added and the mixture was stirred overnight. 1N HCl was used to dissolve the salts and ethyl acetate was added to extract the product. The organic extract was washed with 1N HCl (3×) and brine, dried over sodium sulfate, and the solvent was removed under reduced pressure to obtain the crude product which is used without further purification.

Step 3: 4-(cyclopropylsulfonyl)phenol

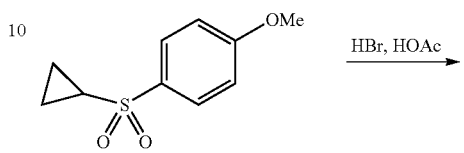

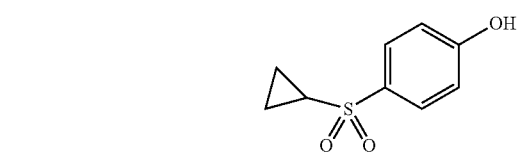

The title phenol was prepared by cleavage of the methyl ether from step 2 of this example by a procedure analogous to Example 56.

Preparative Example 65

Preparation of 4-(1,2,4-oxadiazol-3-yl)phenol

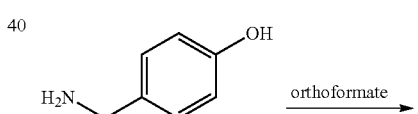

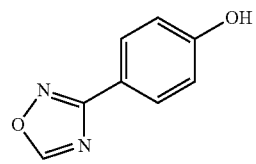

N',4-Dihydroxybenzenecarboximidamide (1.28 g, 8.4 mmol) was suspended in 3 mL ethanol and 3 mL trimethylorthoformate in a 20 mL biotage microwave reaction tube. The mixture was sealed and microwaved at 150° C. for 10 min. The solvent was removed by concentration and the residue was purified by column chromatography eluting with 20% DCM/ hexanes to give the desired product as white solid. LRMS calc: 162.0; obs: 163.2 (M+1).

Preparative Example 66

Preparation of 4-(1,2,4-oxadiazol-5-yl)phenol

Step 1: N-[(1E)-(dimethylamino)methylene]-4-hydroxybenzamide

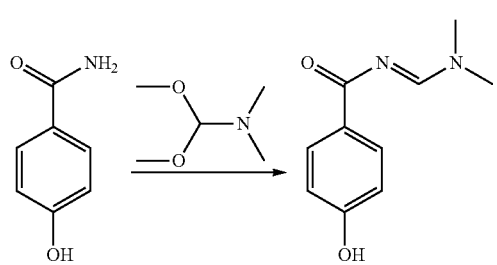

A solution of 4-hydroxybenzamide (5.58 g, 40 mmol) in 15 mL of dimethylformamide dimethyl acetal was stirred at 120° C. for 1.5 h with distillation of the product methanol. After cooling, the solid was collected and tritrarated with diethyl ether, DCM to give desired product.

Step 2: 4-(1,2,4-oxadiazol-5-yl)phenol

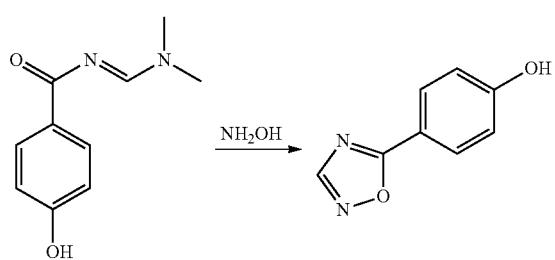

To a solution of hydroxylamine hydrochloride (354 mg, 5.1 mmol) in an a mixture of aqueous 5N sodium hydroxide solution (1 mL, 5 mmol), acetic acid (10 mL) and dioxane (8.5 mL) was added the N-[(1E)-(dimethylamino)methylene]-4-hydroxybenzamide from step 1 of this Example (815 mg, 4.24 mmol). The reaction was stirred at 90° C. for 3 hrs. Upon cooling to room temperature, the solvent was removed under vacuum and residue was purified by column chromatography on an 80 gram biotage silica gel cartridge eluting with 20-50% ethyl acetate/hexanes (gradient) to give the product as white solid. LRMS calc: 162.0; obs: 163.2 (M+1).

Preparative Example 67

Preparation of 4-isoxazol-4-ylphenol

Step 1: 4-(4-methoxyphenyl)isoxazole

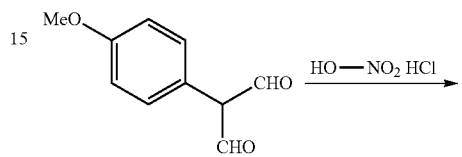

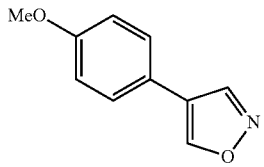

The (4-methoxyphenyl)malonaldehyde (2.5 g, 14 mmol) was heated under reflux with hydroxylamine hydrochlorid (1.46 g, 21 mmol) in ethanol (28 mL) for 2 hours. Ethanol was removed under vacuum and the residue was purified by column chromatography through a 115 gram biotage silica gel cartridge eluting with 20-50% EtOAc/hexanes to give pale oil, which solidified upon standing overnight.

Step 2: 4-isoxazol-4-ylphenol

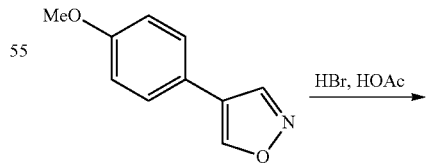

The title phenol was prepared by cleavage of the methyl ether from step 1 of this example by a procedure analogous to Example 56.

Preparative Example 68

Preparation of 4-isoxazol-5-ylphenol

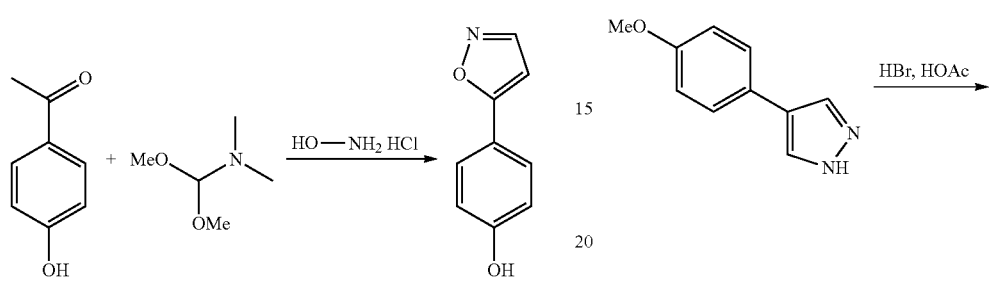

1-(4-hydroxyphenyl)ethanone (5 g, 36.7 mmol) was heated in dimethylformamide dimethyl acetal (6.56 g, 55 mmol) at 100° C. overnight. The solution turned dark red. Volatile solvent was removed under high vacuum. The crude 3-(dimethylamino)-1-(4-hydroxyphenyl)prop-2-en-1-one was dissolved in ethanol, followed by addition of hydroxylamine hydrochloride salt. The mixture was heated under reflux for 3 hours. The solvent was removed under vacuum. The residue was purified twice by column chromatography through 120 g biotage silica gel cartridges eluting with 10-40% EtOAc/hexanes (gradient) and 20% ethyl acetate/hexanes (isocratic) to give the product as white solid. LRMS calc: 161.1; obs: 162.2 (M+1).

Preparative Example 69

Preparation of 4-(1H-pyrazol-4-yl)phenol

Step 1: 4-(4-methoxyphenyl)-1H-pyrazole

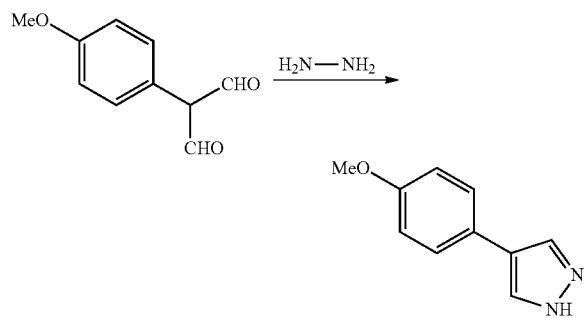

The (4-methoxyphenyl)malonaldehyde (1.5 g, 8.42 mmol) was dissolved in ethanol (10 mL), followed by addition of hydrazine (540 mg g, 16.8 mmol). The pale yellow solution was heated in a microwave sealed tube at 110° C. overnight. Large amount of white crystalline solid formed. The reaction mixture was cooled to 0° C. The white solid was collected by filtration and was washed with 5 mL of ice-cold ethanol to give the desired product, which was further dried under high vacuum pump.

Step 2: 4-(4-methoxyphenyl)-1H-pyrazole

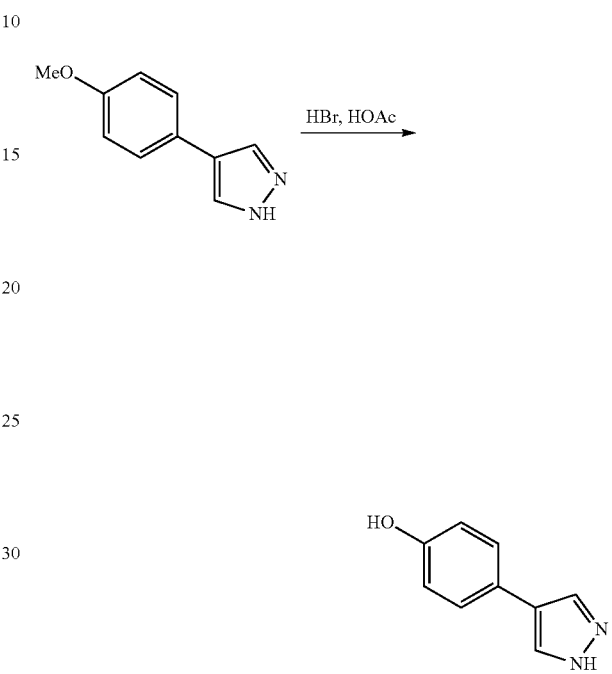

The title phenol was prepared by cleavage of the methyl ether from step 1 of this example by a procedure analogous to Example 56.

Preparative Example 70

Preparation of 4-(4H-1,2,4-triazol-4-yl)phenol

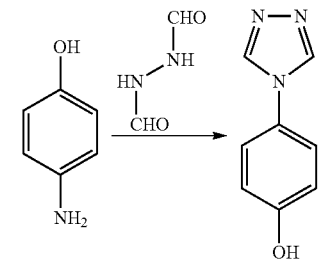

4-aminophenol (1 g, 9.16 mmol) and bisformyl hydrazine (888 mg, 10.08 mmol) were dissolved in a mixture of toluene (30 mL) and DMF (3 mL), followed by addition of pTSA (1.92 g, 10.08 mmol). The mixture was heated under reflux for 3 hours. Upon cooling, the mixture separated to two layers. The upper toluene layer was discarded. The lower dark DMF layer was directly purified by column chromatography using a 115 gram biotage silica gel cartridge eluting with 20-40 ethyl acetate/hexanes (gradient) to give the product as pale yellow solid. LRMS tale: 161.1; obs: 162.4 (M+1).

Preparative Example 71

Preparation of 4-(1H-1,2,3-triazol-1-yl)phenol and 4-(2H-1,2,3-triazol-2-yl)phenol Step 1: 1-[4-(benzyloxy)phenyl]-1H-1,2,3-triazole and 2-[4-benzyloxy)phenyl]-2H-1,2,3-triazole

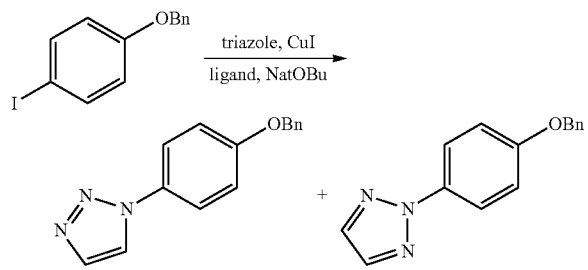

To sealable pressure tube were added CuI (614 mg, 3.22 mmol), 1H-1,2,3-triazole (668 mg, 9.67 mmol), sodium t-butoxide (1.085 g, 9.67 mmol), 1-(benzyloxy)-4-iodobenzene (1 g, 3.22 mmol), and a stir bar. The reaction vessel was fitted with a rubber septum, was evacuated and back-filled with argon, and this sequence was repeated. The N,N'-dimethylethylene diamine (853 mg, 9.67 mmol) and NMP (6.45 mL) were then added successively under a stream of argon. The reaction tube was crimp sealed with a fresh PTFE septum (caution: build-up of pressure possible; use a safety shield) and immersed in a preheated oil bath at 130° C. for 3 h and the solution was stirred magnetically. The reaction mixture was removed from heating, allowed to attain ambient temperature, diluted with ethyl acetate (8 mL), saturated ammonia chloride (8 mL) and 28% aqueous ammonium hydroxide (2 mL). The mixture was vigorously stirred for 30 min and filtered through celite. The filtrate was separated. The aqueous layer was further extracted with ethyl acetate. The organic layers were combined, washed with water, brine, dried over sodium sulfate, concentrated and the resulting residue was purified by silica gel column chromatography (115 gram biotage silica gel cartridge, 10-20% then 40-60% ethyl acetate/hexanes) to separate two regio-isomers as white solid. The more polar fraction was 1-[4-(benzyloxy)phenyl]-1H-1,2,3-triazole.

LRMS calc: 251.1; obs: 252.5 (M+1). The less polar fraction was 2-[4-(benzyloxy)phenyl]-2H-1,2,3-triazole. LRMS calc: 251.3; obs: 252.4 (M+1).

Step 2: 4-(1H-1,2,3-triazol-1-yl)phenol

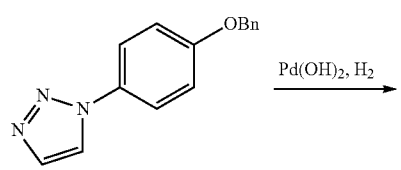

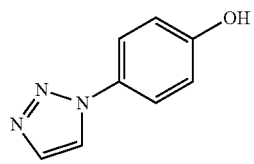

1-[4-(benzyloxy)phenyl]-1H-1,2,3-triazole (200 mg, 0.8 mmol) was dissolved in 1.6 mL of a mixture of ethyl acetate and ethanol (1:1). The solution was degassed and purged with nitrogen. Palladium hydroxide (20% w/w on carbon, 55.9 mg, 0.08 mmol) was added and the reaction was degassed and purged with hydrogen three times. The hydrogenation was continued at room temperature under a hydrogen balloon overnight. The catalyst was removed by filtration through a plug of silica gel, which was washed thoroughly with acetone. Concentration afforded the product as white solid. LRMS calc: 161.1; obs: 162.2 (M+1).

Step 2': 4-(2H-1,2,3-triazol-2-yl)phenol

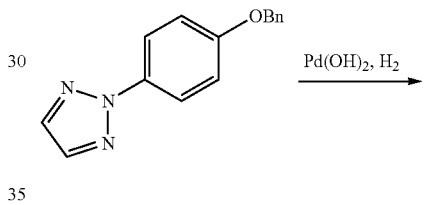

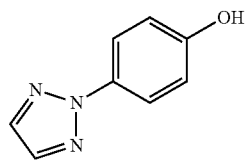

2-[4-(benzyloxy)phenyl]-2H-1,2,3-triazole (400 mg, 1.6 mmol) was dissolved in 3.2 mL of a mixture of ethyl acetate and ethanol (1:1). The solution was degassed and purged with nitrogen. Palladium hydroxide (20% w/w on carbon, 110 mg, 0.16 mmol) was added and the reaction was degassed and purged with hydrogen three times. The hydrogenation was continued at room temperature under a hydrogen balloon for 1 hour. The catalyst was removed by filtration through a plug of silica gel, which was washed thoroughly with acetone.

Concentration afforded the product as white solid. LRMS calc: 161.1; obs: 162.2 (M+1).

Preparative Example 71a

Preparation of 5-(1H-1,2,3-triazol-1-yl)-2-hydroxypyridine

Step 1: 5-Iodo-2-(4'-methoxybenzyloxy)pyridine

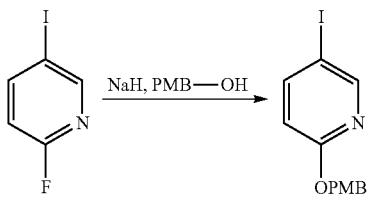

4-Methoxybenzyl alcohol (6.51 g, 47.1 mole) in 15 mL DMF was added to a stirring suspension of sodium hydride (1.973 g, 49.3 mmol) in DMF at 0° C. After 10 minutes a solution of 2-fluoro-5-iodopyridine (10 g, 44.8 mmol) in 15 mL DMF was added dropwise using an addition funnel. The reaction slowly reached room temperature, and was allowed to stir for 18 hours. The homogenous yellow solution was cooled again and quenched with about 50 ml of water. The suspension was then partitioned between ethyl acetate (200 mL) and water (150 mL). The aqueous was extracted a second time with ethyl acetate and the combined organic layers were washed with water three times and with brine twice. The organic layer was dried over sodium sulfate, filtered and evaporated. When the evaporation neared completion a white solid precipitated. Triturated with the addition of hexanes. The solid was filtered and dried on the filter. Repeated partial evaporation trituration and filtration of the resulting white solids gave the title compound.

NMR (CDCl$_3$): δ 8.35 (d, 1H, J=2.3 Hz), δ 7.77 (dd, 1H, J=8.7, 1.3 Hz), δ 7.37 (d, 2H,), δ 7.26 (s, CHCl$_3$), δ 6.90 (d, 2H), δ 6.61 (d, 1'-1, J=8.7 Hz), δ 5.26 (s, 2H), δ 3.81 (s 3H).

Step 2: 5-Azido-2-(4'-methoxybenzyloxy)pyridine

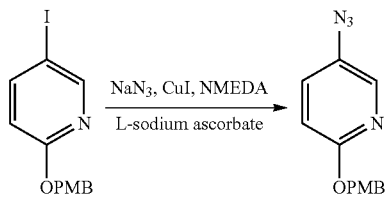

5-Iodo-2-(4'-methoxybenzyloxy)pyridine from step 1 of this example (682 mg, 2.0 mmol), sodium azide (260 mg, 4.00 mmol), copper (1) iodide (38.1 mg, 0.200 mmol) and L-ascorbic acid sodium salt (19.81 mg, 0.100 mmol) were added to a sealable high pressure vessel. The vessel was evacuated and purged with nitrogen, then ethanol (2.75 ml) and water (1.25 ml) were added. N,N-dimethylethylenediamine (31.9 μl, 0.300 mmol) was then added via microliter syringe. The top was sealed and the reaction heated to 100° C. A safety shield was placed in front of the reaction as a precaution. After 90 minutes, the reaction was cooled to room temperature. Reaction was judged to be complete by TLC, so the reaction was partitioned between ethyl acetate and water. The aqueous was extracted again with ethyl acetate, and the combined organics washed again with water. The organic layer was dried over sodium sulfate, filtered and evaporated to give the crude product. The material was purified by column chromatography on a Biotage 40 g SiO$_2$ column, eluting with 5-25% ethyl acetate/heptane to give the title compound as a light tan solid.

NMR (CDCl$_3$): δ 7.92 (d, J=3.0 Hz), δ 7.38 (d, 2H,), δ 7.28 (dd, 1H, J=8.9, 3.0 Hz), δ 7.26 (s, CHCl$_3$), δ 6.90 (d, 2H), δ 6.78 (d, 1H, J=8.7 Hz), δ 5.27 (s, 2H), δ 3.81 (s 3H).

Step 3: 5-(1H-1,2,3-triazol-1-yl)-2-(4'-methoxybenzyloxy)pyridine

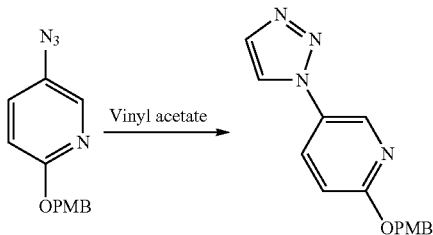

5-Azido-2-(4'-methoxybenzyloxy)pyridine from step 2 of this example (55 mg, 0.215 mmol) and vinyl acetate (692 μl, 7.51 mmol) were mixed in a flame dried high pressure sealable vessel. The reaction vessel was evacuated and charged with nitrogen, sealed, and heated to 100° C. for 15 hours. The reaction was cooled to room temperature and TLC indicated that the reaction was complete. Minimal dichloromethane was added to the reaction (just enough to dissolve solids that formed upon cooling) and the solution added to a Biotage 25 g SiO$_2$ column, eluting with 20-50% ethyl acetate/heptane to give the title compound as a white solid.

LRMS: calc: 282.1 obs: 282.9 (M+1).

NMR (CDCl$_3$): δ 8.50 (d, 1H, J=2.7 Hz), δ 7.97 (dd, 1H, J=8.9, 2.7 Hz), δ 7.93 (d, 1H, J=0.9 Hz), δ 7.87 (d, 1H, J=1.0 Hz), δ 7.41 (d, 2H,), δ 7.26 (s, CHCl$_3$), δ 6.93 (m, 3H), δ 5.37 (s, 2H), δ 3.82 (s 3H).

Step 4: 5-(1H-1,2,3-triazol-1-yl)-2-hydroxypyridine

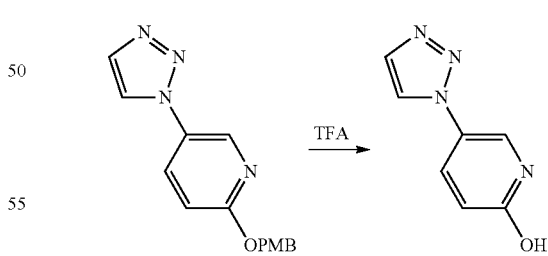

5-(1H-1,2,3-triazol-1-yl)-2-(4'-methoxybenzyloxy)pyridine from step 3 of this example (890 mg, 3.15 mmol) was dissolved in dichloromethane (11 ml). Trifluoroacetic acid (3.64 ml, 47.3 mmol) was added and the mixture stirred at RT. Within 10 minutes the reaction had turned light purple. The reaction mixture was evaporated 40 minutes after TFA addition, then reconstituted in CH$_2$Cl$_2$/heptane and evaporated again. The residue was purified by column chromatography on a Biotage 40 g SiO$_2$ column, eluting with 0-15% methanol in CH$_2$Cl$_2$ to give a white solid. The white solid was suspended in acetone and filtered over celite to remove silica from the crude. The filtrate was then evaporated and pumped on high vacuum overnight to give the title compound as a complex with acetone.

LRMS: calc: 162.1 obs: 162.9 (M+1)

NMR (CD$_3$OD): δ 8.38 (d, 1H, J=1.1 Hz), δ 8.03 (s, 1H), δ 8.02 (d, 1H, J=9 Hz), δ 7.87 (d, 1H, J=0.9 Hz), δ 6.69 (d, 1H, J=10.5 Hz), δ 2.15 (acetone).

Preparative Example 71b

Preparation of 5-chloro-2-{4-[(1R,2S)-2-(2-{[5-(1H-1,2,3-triazol-1-yl)pyridin-2-yl]oxy}ethyl)cyclopropyl]piperidin-1-yl}pyrimidine Step 1: 5-Azido-2-fluoropyridine

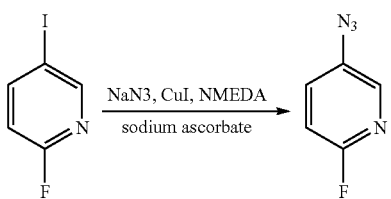 [SMILES: Fc1ccc(I)cn1 ; [N-]=[N+]=Nc1ccc(F)nc1]

2-Fluoro-5-iodopyridine (1.12 g, 5 mmol), sodium azide (390 mg, 6.00 mmol), copper(I) iodide (95 mg, 0.500 mmol) and L-ascorbic acid sodium salt (49.5 mg, 0.250 mmol) were added to a flame dried sealable reaction vessel. The vessel was evacuated and purged with nitrogen. Ethanol (7 mL) and water (3 ml) were added to the reaction vessel, which was then evacuated and purged again with nitrogen. N,N'-Dimethylethylenediamine (80 µl, 0.750 mmol) was added to the vessel via microliter syringe. The top was screwed on and the reaction heated to 100° C. A safety shield was placed in front of the reaction as a precaution. The reaction was monitored by TLC, which indicated consumption of starting material after 45 minutes. The reaction was diluted with water and extracted with ethyl acetate twice. The combined organics were washed three times with water and once with brine. The organic was dried over sodium sulfate, filtered and evaporated to give 630 mg of crude material, which contains azide, starting material, and another impurity. This was carried on to the next step without purification. $^1$H NMR (CDCl$_3$): δ 7.95 (d, 1H), 7.45 (m, 1H), 7.26 (s, CDCl$_3$), 6.95 (dd, 1H).

Step 2: 5-(1H-1,2,3-triazol-1-yl)-2-fluoropyridine

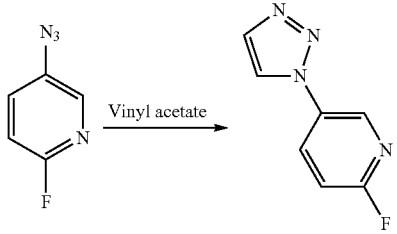 [SMILES: [N-]=[N+]=Nc1ccc(F)nc1 ; Fc1ccc(-n2ccnn2)cn1]

5-Azido-2-fluoropyridine (262 mg, 1.9 mmol) and vinyl acetate (4.0 mL, 43 mmol) were mixed in a flame dried high pressure sealable vessel. The reaction vessel was evacuated and charged with nitrogen, sealed, and heated to 100° C. for 15 hours. The reaction was cooled to room temperature and TLC indicated that the reaction was complete. Minimal dichloromethane was added to the reaction (just enough to dissolve solids that formed upon cooling) and the solution directly chromatographed on silica gel (Biotage size 40S column), eluting with 20-50% ethyl acetate/heptane to give the title compound as a white solid.

LRMS: talc: 164.05 obs: 164.95 (M+1). $^1$H NMR (CDCl$_3$): δ 8.60 (d, 1H), 8.27 (m, 1H), 8.03 (d, 1H), 7.91 (d, 1H), 7.26 (s, CDCl3), 7.15 (dd, 1H).

Preparative Example 72

Preparation of 4-(1H-1,2,3-triazol-5-yl)phenol

Step 1: 4-[4-(benzyloxy)phenyl]-1H-1,2,3-triazole

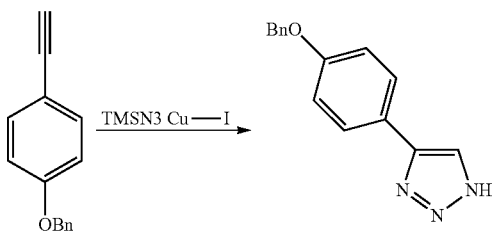

Trimethylsilyl azide (415 mg, 3.6 mmol) was added to a DMF (4.3 mL) and MeOH (0.48 mL) solution containing CuI (22.9 mg, 0.12 mmol) and 1-(benzyloxy)-4-ethynylbenzene (500 mg, 2.4 mmol) under Ar in a pressure tube (caution: build-up of pressure possible; use a safety shield). The reaction mixture was stirred at 100° C. for 12 h. The mixture was cooled to room temperature and filtered through a short silica gel pad and concentrated. The residue was purified by recrystallization from DCM.

Step 2: 4-(1H-1,2,3-triazol-5-yl)phenol

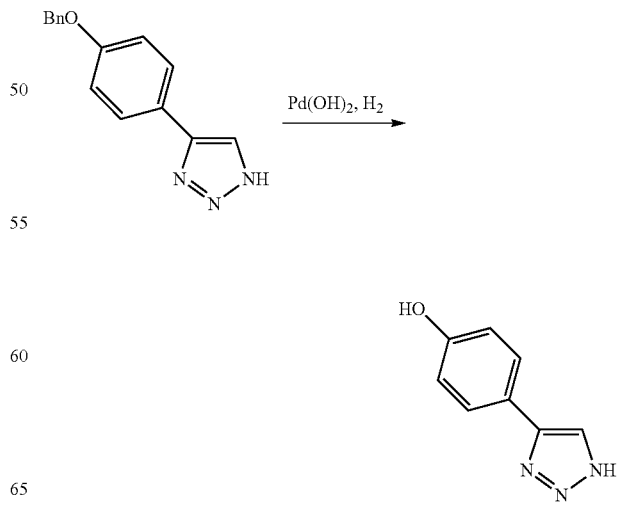

95

The title phenol was prepared by cleavage of the benzyl ether from step 1 of this Example by a procedure analogous to Example 71, step 2.

Preparative Example 73

Preparation of 4-1H-tetrazol-1-yl)phenol

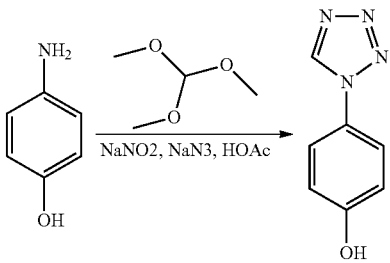

Trimethylorthoformate (9.34 g, 88 mmol) was added to a flask charged with the 4-hydroxyaniline (3 g, 27.5 mmol) followed by sodium nitrite (1.9 g, 27.5 mmol) and acetic acid (50 mL). The mixture was heated to 80° C. for 2 hrs, the reaction was removed from the heating bath and transferred to an Erlenmeyer flask. The flask was cooled to 0° C. with an ice bath upon which water (25 mL) and aqueous HCl solution (6M, 11 mL) were added. Sodium azide (2.234 g, 34.4 mmol) in water (as 3M solution) was added slowly to the reaction mixture. The resulting precipitate was collected and dried under vacuum to give the desired product. LRMS calc: 162.1; obs: 163.2 (M+1).

Preparative Example 73a

Preparation of 3-fluoro-4-(1H-tetrazol-1-yl)phenol

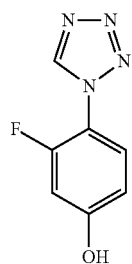 [SMILES: Oc1ccc(-n2cnnn2)c(F)c1]

96

The title compound was prepared from 4-amino-3-fluorophenol, by a procedure analogous to that described for Example 73

Preparative Example 75

Preparation of 4-(2H-tetrazol-2-yl)phenol

Step 1: 2-(4-nitrophenyl)-2H-tetrazole

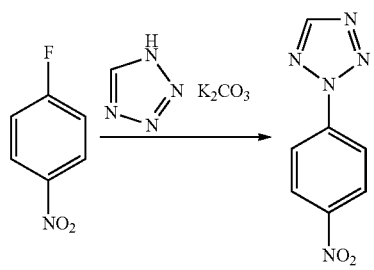

1H-tetrazole in acetonitrile solution (0.45M, 19 mL, 8.5 mmol) was combined with 4-fluoro-nitrobenzene (1 g, 7.09 mmol) in a 40 mL pressure tube, followed by addition of potassium carbonate. The tube was sealed and heated at 110° C. overnight (caution: build-up of pressure possible; use a safety shield). Pressure buildup was observed. The pressure was released carefully. The reaction was concentrated to dryness and diluted with water. The aqueous mixture was extracted 4 times with DCM. The combine organic layers were dried over sodium sulfate, filtered, concentrated and purified by column chromatography through a 40 gram biotage silica gel cartridge eluted with 5-20% ethyl acetate/hexanes (gradient) to give the product as white solid. LRMS talc: 191.0; obs: 192.3 (M+1).

Step 2: 4-(2H-tetrazol-2-yl)aniline

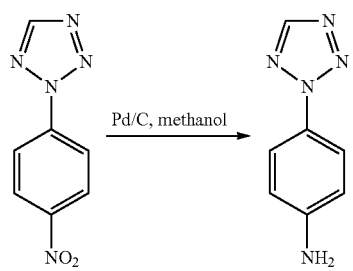

2-(4-Nitrophenyl)-2H-tetrazole (200 mg, 1.05 mmol) was suspended in ethanol (1 mL). Ethyl acetate (1 mL) was added to improved solubility. The solution was degassed and purged with nitrogen 3 times before palladium on carbon (10% w/w, 223 mg, 0.2 mmol) was added. The mixture was degassed and purged with hydrogen 3 times and stirred under a hydrogen balloon for 2 hours. The reaction was diluted with acetone and passed through a plug of silica gel, which was washed thoroughly with acetone. The filtrated was concentrated to give the crude product which was used as isolated.

Step 3: 4-(2H-tetrazol-2-yl)phenol

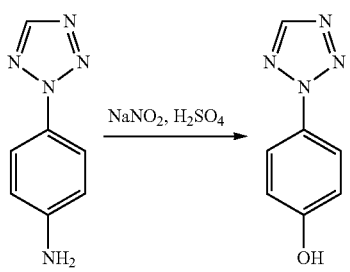

The crude 4-(2H-tetrazol-2-yl)aniline (60 mg, 0372 mmol) was suspended in water (2 mL) and sulfuric acid (0.2 mL) before cooling to 0° C. An aqueous solution of sodium nitrite (26 mg, 0.565 mmol) in water (2 mL) was added. The mixture was stirred at 0° C. for 30 min. Additional water (1 mL) and sulfuric acid (0.37 mL) was added and the mixture heated at 120° C. for 1 hour. The reaction was then cooled and extracted 3 times with ethyl acetate. The combined organic layers were washed with brine, dried over sodium sulfate, filtered, concentrated and purified by preparative TLC eluting with 30% ethyl acetate/hexanes to give the desired phenol product as yellow solid. LRMS calc: 162.1; obs: 163.2 (M+1).

Preparative Example 75a

Preparation of 4-(5-methyl-2H-tetrazol-2-yl)phenol and 4-(5-methyl-1H-tetrazol-1-yl)phenol Step 1: 5-methyl-2-(4-nitrophenyl)-2H-tetrazole and 5-methyl-1-(4-nitrophenyl)-1H-tetrazole

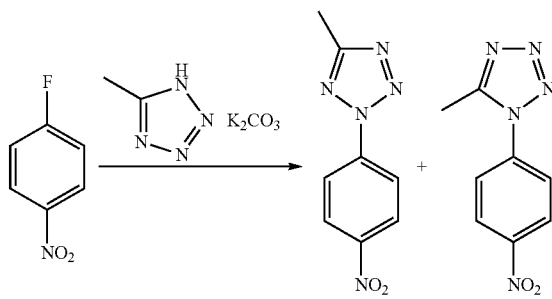

5-methyl-1H-tetrazole (715 mg, 8.5 mmol) was dissolved in DMF (7 mL) in a 40 mL biotage microwave tube. 4-fluoronitrobenzene (1 g, 7.09 mmol) was added, followed by addition of potassium carbonate (1.175 g, 8.5 mmol). The tube was crimp sealed and heated at 110° C. for 4 hours (caution: build-up of pressure possible; use a safety shield). TLC indicated complete consumption of starting materials. Most DMF was removed under vacuum. Water (50 mL) was added. Large amount of brown solid formed (1 gram) and was collected by filtration. The solid was further purified by column through a 80 gram biotage silica gel cartridge using 30-75% ethyl acetate/hexanes to give clean fraction of 5-methyl-2-(4-nitrophenyl)-2H-tetrazole, LRMS calc: 205.1; obs: 206.3 (W+1).

The mother liquor after the filtration was extracted 4 times with DCM. The combined organic phases were dried over sodium sulfate, filtered, concentrated and purified by column chromatography through a 80 gram biotage silica gel cartridge using 30-75% ethyl acetate/hexanes to afford 5-methyl-1-(4-nitrophenyl)-1H-tetrazole, LRMS calc: 205.1; obs: 206.3 (M+1).

Step 2: 4-(5-methyl-2H-tetrazol-2-yl)aniline and 4-(5-methyl-1H-tetrazol-1-yl)aniline

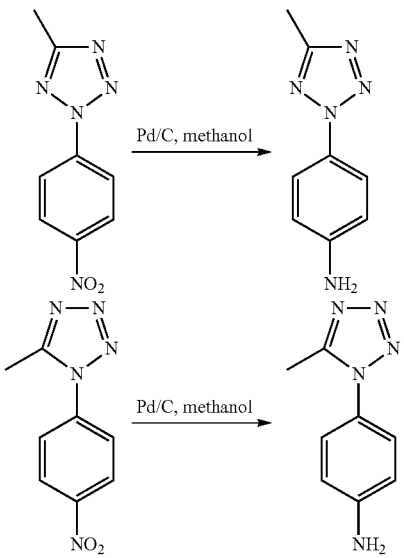

5-Methyl-2-(4-nitrophenyl)-2H-tetrazole (200 mg, 0.975 mmol) was suspended in methanol (15 mL). The solution was degassed and purged with nitrogen 3 times before palladium on carbon (10% w/w, 51.9 mg, 0.049 mmol) was added. The mixture was degassed and purged with hydrogen 3 times and stirred under a hydrogen balloon for 2 hours. The reaction was diluted with acetone and passed through a plug of silica gel, which was washed thoroughly with acetone. The filtrated was concentrated to give the crude product 4-(5-methyl-2H-tetrazol-2-yl)aniline which was used as isolated.

4-(5-Methyl-1H-tetrazol-1-yl)aniline was synthesized under identical conditions.

Step 3. 4-(5-methyl-2H-tetrazol-2-yl)phenol and 4-(5-methyl-1H-tetrazol-1-yl)phenol

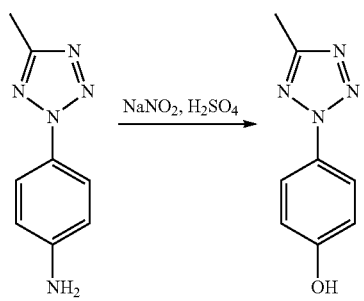

99

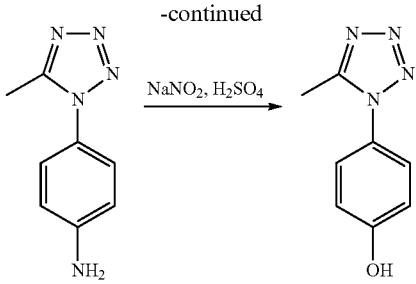

The title compounds were synthesized by a procedure analogous to Example 75, step 3.

Preparative Example 76

Preparation of 6-hydroxy-2-methylpyrimidine-4-carbonitrile

Step 1: 4-chloro-6-[(4-methoxybenzyl)oxy]-2-methylpyrimidine

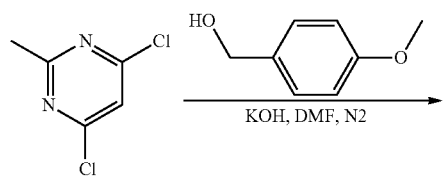

4-Methoxybenzyl alcohol (1.66 g, 12 mmol) was dissolved in DMF (20 mL). Potassium hydroxide (2.31 g, 36 mmol, 87%) was added and stirred at room temperature for 10 min followed by cooling to 0° C. 4,6-dichloro-2-methylpyrimidine (2.15 g, 13.2 mmol) was dissolved in DMF (4 mL) and added to the solution drop-wise. The internal temperature was controlled under 2° C. The reaction solution was kept at 0° C. for 2 h, then allowed to warm slowly to 16° C. over 1 hr. The reaction was diluted with ethyl acetate (50 mL), washed with brine (50 mL×2), dried over MgSO$_4$, filtered and concentrated i. vac. The crude mixture was purified by chromatography on silica gel (eluting 7.7% ethyl acetate/hexane) to yield the titled compound as a colorless oil. LC-MS (M+1): 265.51, (M+23): 287.52.

Step 2: 6-[(4-methoxybenzyl)oxy]-2-methylpyrimidine-4-carbonitrile

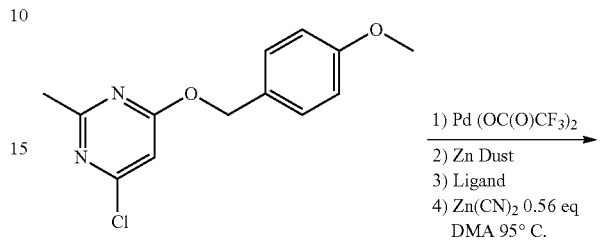

The starting 4-chloro-6-[(4-methoxybenzyl)oxy]-2-methylpyrimidine from step 1 of this example (3.7 g 14 mmol), palladium trifluoroacetate (0.2 g, 0.6 mmol), racemic-2-(di-t-butylphosphino)-1,1-binaphthyl ligand (0.49 g, 1.23 mmol), zinc dust (0.17 g, 2.65 mmol) and zinc cyanide (0.92 g, 7.8 mmol) were added to a flask (100 mL), and dimethylacetamide (73 mL) was added. The flask was evacuated and back filled with N$_2$ (3 times), and reaction solution was stirred at room temperature for 30 min. The reaction was then heated to 95° C. for 30 min and monitored until starting material was consumed. The reaction was cooled to room temperature, diluted with ethyl acetate (100 mL), washed with brine (50 mL, ×2), dried over MgSO$_4$, filtered and concentrated i. vac. The crude pale yellow oil was purified by chromatography on silica gel (eluting 7.7% ethyl acetate/hexane) to yield the titled compound as a white solid. LC-MS (M+23): 278.

Step 3: 6-hydroxy-2-methylpyrimidine-4-carbonitrile

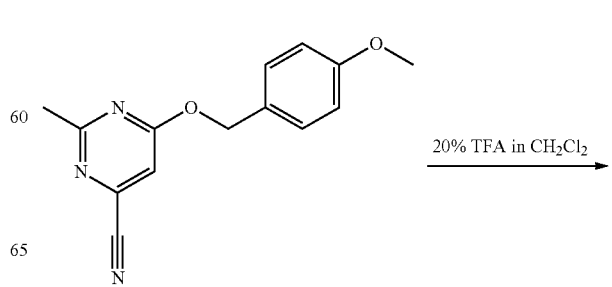

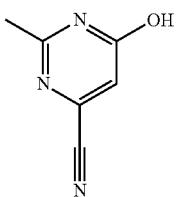

The 6-[(4-methoxybenzyl)oxy]-2-methylpyrimidine-4-carbonitrile from step 2 of this example (2.8 g, 11 mmol) was dissolved in DCM (9.1 mL) and TFA (1.8 mL) was added via syringe drop-wise. The reaction was allowed to proceed 10 min. at room temperature and was concentrated to near dryness, without heating, under vacuum. The residue was dissolved in DCM (10 mL), and saturated NaHCO$_3$ solution (aq, 5 mL) was added to adjust pH to ~7. Acetic acid (1 mL) was then added to the solution to adjust pH to ~4 and the mixture was concentrated to dryness i. vac. The residue was purified by chromatography on silica gel using gradient elution: starting at 30% ethyl acetate/hexane, then switching to 5% methanol/DCM to yield the titled compound as a white solid. LC-MS (M+1): 136.16.

Preparative Example 76a

Preparation of 6-chloro-2-methylpyrimidine-4-carbonitrile

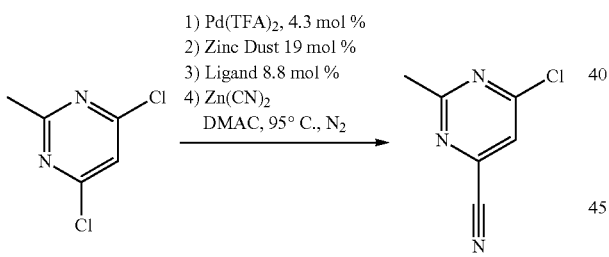

The 4,6-dichloro-2-methyl-pyrimidine (10 g, 60 mmol), palladium (II) trifluoroacetate (0.86 g, 2.6 mmol), zinc dust (65.3 g, 11.4 mmol), rac-2-(di-t-butylphosphino)-1,1'-binaphthyl (2.1 g, 5.3 mmol), zinc cyanide (3.95 g, 33.7 mmol) and dimethyl acetamide (316 ml) were added to a 500 mL, flame-dried flask. The vessel was evacuated and back-filled with N$_2$ (3×). The mixture was stirred under N$_2$ for 30 min. at RT, then heated to 95° C. After 2.5 hours the mixture was diluted with EtOAc (300 mL), and washed with water (300 mL×3). The organic fractions were combined, dried over MgSO$_4$, filtered, and the volatiles removed in vac. The residue was dissolved in EtOAc (100 mL), washed with water (50 ml), and the layers separated. The aqueous phase was then extracted with EtOAc (50 mL), the organic fractions combined, dried over MgSO$_4$, filtered, and the volatiles removed in vac. The crude mixture was purified by chromatography on silica gel (eluting 1:19 ethyl acetate:hexane) to yield the titled compound as a colorless oil. $^1$H NMR (CD$_3$OD): 8.235 (s, 1H), 2.816 (s, 3H).

The following phenol precursors were prepared similarly:

Preparative Example 77

Preparation of 4-hydroxy-6-methylpyrimidine-2-carbonitrile

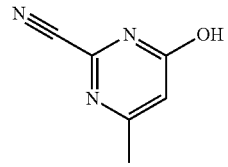

The titled compound was prepared from 2,4-dichloro-6-methylpyrimidine by a procedure analogous to that described for Example 76.

LC-MS (M+1): 136.16.

Preparative Example 78

Preparation of 6-hydroxypyrimidine-4-carbonitrile

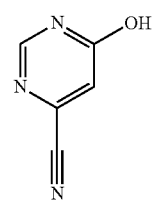

The title compound was prepared from 4,6-dichloropyrimidine by a procedure analogous to that described for Example 76.

LC-MS (M+1): 122.07.

Preparative Example 79

Preparation of 4-hydroxypyrimidine-2-carbonitrile

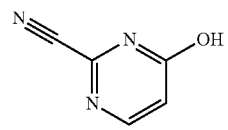

The title compound was prepared from 2,4-dichloropyrimidine by a procedure analogous to that described for Example 76.

LC-MS (M+1): 122.06.

Preparative Example 80

Preparation of 5-hydroxynicotinonitrile

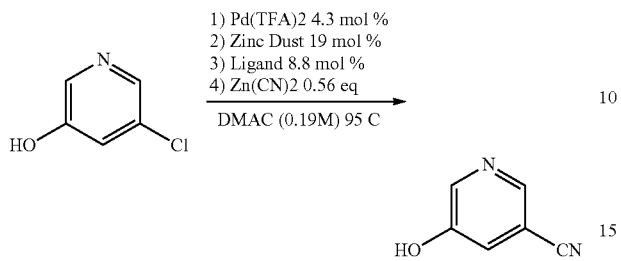

The title compound was prepared from 5-chloropyridin-3-ol by a procedure analogous to that described for Example 76, step 2.

LC-MS (M+1): 121.08.

Preparative Example 81

Preparation of 5-hydroxypyridine-2-carbonitrile

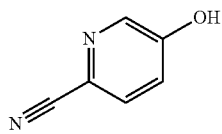

The title compound was prepared from 6-chloropyridin-3-ol by a procedure analogous to that described for Example 76, step 2.

LC-MS (M+1): 121.08.

Preparative Example 81a

Preparation of 2-{2-[1-(5-chloro-4-methylpyrimidin-2-yl)piperidin-4-yl]cyclopropyl}ethanol

Step 1: Preparation of 2,5-dichloro-4-methylpyrimidine

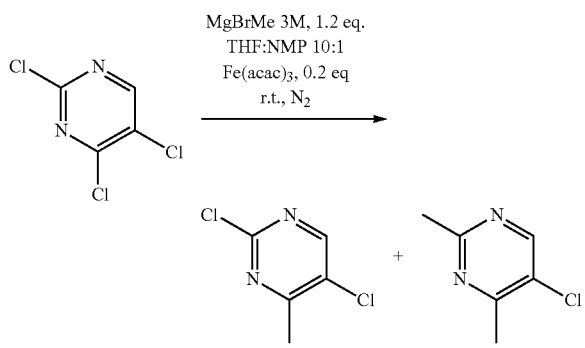

2,4,5-trichloropyrimidine (1.83 g, 10 mmol) was dissolved in THF:NMP (10:1, 100 mL) at room temperature and iron(III) acetylacetonate (0.71 g, 2.0 mmol) was added under $N_2$. MgBrMe (3M, 12 mmol) was added drop-wise via syringe. The mixture was cooled to RT, progress was verified by LC-MS: typical results show product vs starting material vs 5-chloro-2,4-dimethylpyrimidine side product ~2:2:1 ratio. The reaction was quenched with ice cold, saturated ammonium chloride (, 100 mL), extracted with ethyl acetate (100 mL), washed with brine (100 mL, ×2), dried over $MgSO_4$, filtered and concentrated i. vac. The crude mixture was purified by silica gel chromatography (5% ethylacetate/hexane) to yield the titled compound.

LC-MS (M+1): 163.23.

Step 2; rac cis-2-{2-[1-(5-chloro-4-methylpyrimidin-2-yl)piperidin-4-yl]cyclopropyl}ethanol

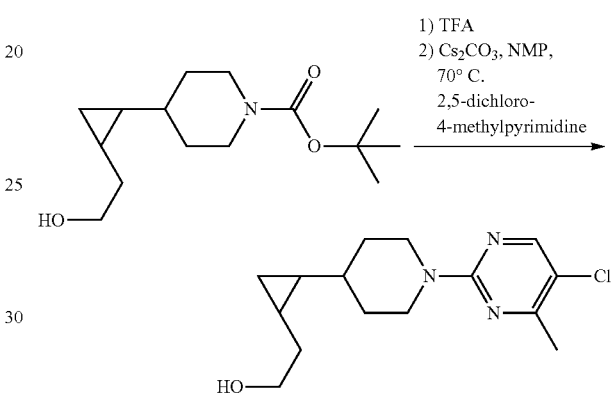

The titled compound was prepared from 2,5-dichloro-4-methylpyrimidine from step 1 of this example and rac cis-tert-Butyl 4-[-2-(2-hydroxyethyl)cyclopropyl]piperidine-1-carboxylate by a procedure analogous to Example 6, step 2.

LC-MS (M+1): 296.61.

Preparative Example 81b

Preparation of 2-{2-[1-(4,5-dimethylpyrimidin-2-yl)piperidin-4-yl]cyclopropyl}ethanol

Step 1: Preparation of 2-chloro-4,5-dimethylpyrimidine

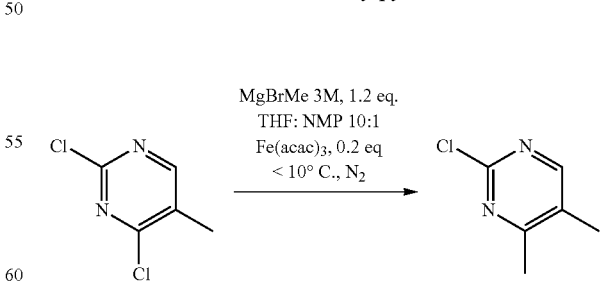

The titled compound was prepared from 2,4-dichloro-5-methylpyrimidine by a procedure analogous to that described in Example 42, step 1, with the exception of reaction temperature. The reaction temperature was maintained under 10° C.

LC-MS (M+1): 143.22.

Step 2 Preparation of 2-{2-[1-(4,5-dimethylpyrimidin-2-yl)piperidin-4-yl]cyclopropyl}ethanol

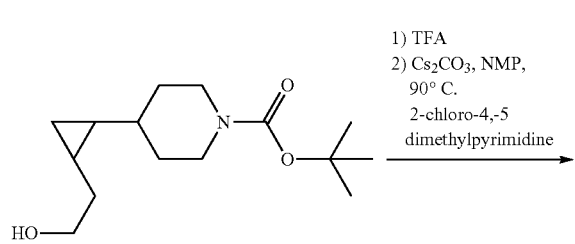

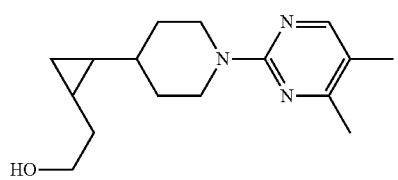

The titled compound was prepared from 2-chloro-4,5-dimethylpyrimidine and rac cis-tert-Butyl 4-[2-(2-hydroxyethyl)cyclopropyl]piperidine-1-carboxylate by a procedure analogous to that described in Example 6, step 2, with the exception of reaction temperature and time. The reaction was heated at 90° C. for 2 h.

LC-MS (M+1): 276.56.

Preparative Example 81c

Preparation of 2-{2-[1-(5-fluoro-4-methylpyrimidin-2-yl)piperidin-4-yl]cyclopropyl}ethanol Step 1: Preparation of 2-chloro-5-fluoro-4-methylpyrimidine

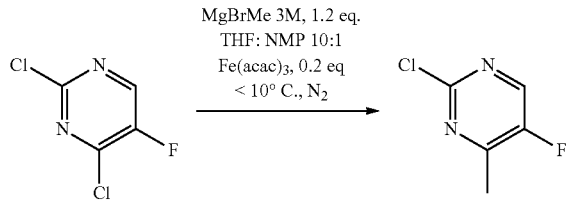

The titled compound is obtained from 2,4-dichloro-5-methylpyrimidine by a procedure analogous to that described in Example 42, step 1, with the exception of reaction temperature and time. The reaction temperature was maintained under 10° C.

LC-MS (M+1): 147.22.

Step 2 2-{2-[1-(5-fluoro-4-methylpyrimidin-2-yl)piperidin-4-yl]cyclopropyl}ethanol

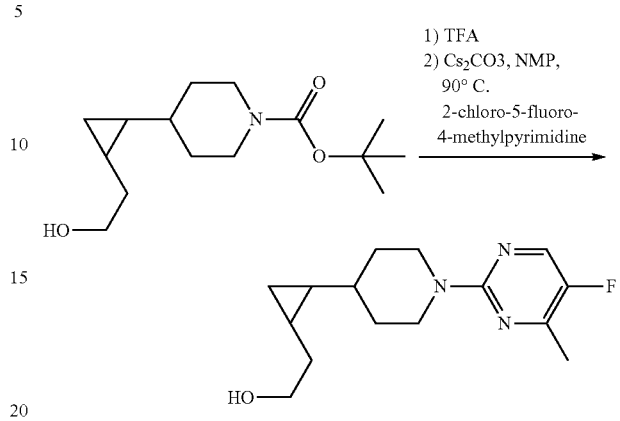

The titled compound was prepared from 2-chloro-5-fluoro-4-methylpyrimidine and rac cis-tert-Butyl-4-[-2-(2-hydroxyethyl)cyclopropyl]piperidine-1-carboxylate by a procedure analogous to example 6 step 2, with the exception of reaction temperature. The reaction was heated at 90° C. for 2 h.

LC-MS (M+1): 280.22.

Example 83 F and S

Preparation of pure enantiomers; 5-chloro-2-[4-((1R,2S)-2-{2-[3-fluoro-4-(5-methyl-1,3,4-oxadiazol-2-yl)phenoxy]ethyl}cyclopropyl)piperidin-1-yl]pyrimidine and 5-chloro-2-[4-((1S,2R)-2-{2-[3-fluoro-4-(5-methyl-1,3,4-oxadiazol-2-yl)phenoxy]ethyl}cyclopropyl)piperidin-1-yl]pyrimidine

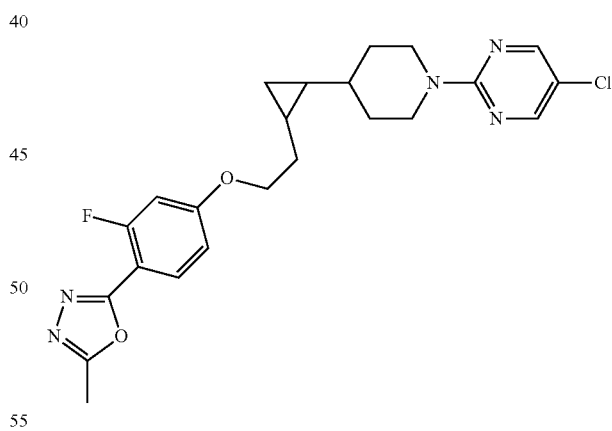

Analytical Screening: rac cis-5-chloro-2-[4-(2-{2-[3-fluoro-4-(5-methyl-1,3,4-oxadiazol-2-yl)phenoxy]ethyl}cyclopropyl)piperidin-1-yl]pyrimidine of Example 14 was successfully resolved on a chiralpak IA 4.6×250 mm, 5μ, at 40% isocratic ethanol/heptane, 0.75 mL/min. Retention time—faster enantiomer: T=12.4 min; slower enantiomer: T=15.9 min.

rac cis-5-chloro-2-[4-(2-{2-[3-fluoro-4-(5-methyl-1,3,4-oxadiazol-2-yl)phenoxy]ethyl}cyclopropyl)piperidin-1-yl]pyrimidine of Example 14 (5 mg) was dissolved in 2.5 mL ethanol. The solution was subjected to HPLC separation on a semi-prep chiralpak IA column (20×250 mm, 5μ), under isocratic elution with 40% ethanol/heptanes at 9 mL/min. The enantiomers were baseline separated. Retention time—faster enantiomer: 83 F, T=32.36 min; slower enantiomer: 83 S, T=44.37 min. The fractions were identified as the enantiomers of cis-5-chloro-2-[4-(2-{2-[3-fluoro-4-(5-methyl-1,3,4-oxadiazol-2-yl)phenoxy]ethyl}cyclopropyl)piperidin-1-yl]pyrimidine.

Example 83a F and S

Preparation of pure enantiomers; 5-chloro-2-[4-(1S,2R)-2-{2-[4-(1H-1,2,3-triazol-1-yl)phenoxy]ethyl}cyclopropyl)piperidin-1-yl]pyrimidine and 5-chloro-2-[4-((1R,2S)-2-{2-[4-(1H-1,2,3-triazol-1-yl)phenoxy]ethyl}cyclopropyl)piperidin-1-yl]pyrimidine

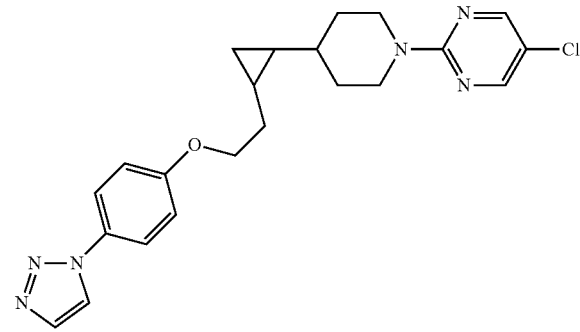 [SMILES: Clc1cnc(N2CCC(C3CC3CCOc3ccc(-n4ccnn4)cc3)CC2)nc1]

rac cis-5-chloro-2-[4-(2-{2-[4-(1H-1,2,3-triazol-1-yl)phenoxy]ethyl}cyclopropyl)piperidin-1-yl]pyrimidine from Example 27 (18 mg) was dissolved in 2.5 mL ethanol. The solution was subjected to HPLC separation on a semi-prep chiralpak IA column (20×250 mm, 5μ), under isocratic elution with 75% ethanol/heptanes at 9 mL/min. The enantiomers were baseline separated. Retention time—faster enantiomer: 83a F, T=17.05 min; slower enantiomer: 83a S, T=22.18 min.

Example 83b F and S

Preparation of pure enantiomers; 5-fluoro-2-[4-((1R,2S)-2-{2-[4-(1H-1,2,3-triazol-1-yl)phenoxy]ethyl}cyclopropyl)piperidin-1-yl]pyrimidine and 5-fluoro-2-[4-((1S,2R)-2-{2-[4-(1H-1,2,3-triazol-1-yl)phenoxy]ethyl}cyclopropyl)piperidin-1-yl]pyrimidine

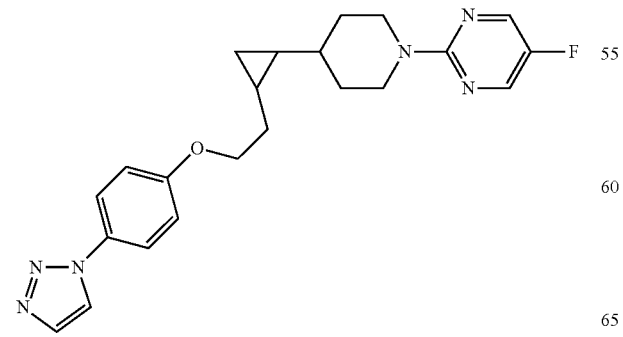

rac cis-5-fluoro-2-[4-(2-{2-[4-(1H-1,2,3-triazol-1-yl)phenoxy]ethyl}cyclopropyl)piperidin-1-yl]pyrimidine from Example 27b (40 mg) was dissolved in 5 mL methanol, 1 mL of DCM was added to improve solubility. The solution was subjected to HPLC separation on a semi-prep chiralpak IA column (20×250 mm, 5μ), under isocratic elution with 75% ethanol/heptanes at 9 mL/min, 3 injections. The enantiomers were baseline separated. Retention time—faster enantiomer: 83b F, T=15.36 min; slower enantiomer: 83b S, T=17.97 min.

Example 83c F and S

Preparation of pure enantiomers; 5-chloro-2-[4-((1R,2S)-2-{2-[4-(1H-tetrazol-1-yl)phenoxy]ethyl}cyclopropyl)piperidin-1-yl]pyrimidine and 5-chloro-2-[4-((1S,2R)-2-{2-[4-(1H-tetrazol-1-yl)phenoxy]ethyl}cyclopropyl)piperidin-1-yl]pyrimidine

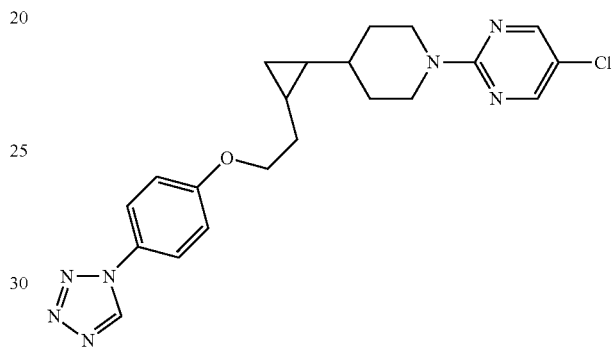

rac cis-5-chloro-2-[4-(2-{2-[4-(1H-tetrazol-1-yl)phenoxy]ethyl}cyclopropyl)piperidin-1-yl]pyrimidine from Example 30 (20 mg) was dissolved in 2.5 mL methanol. The solution was subjected to HPLC separation on a semi-prep chiralpak IA column (20×250 mm, 5μ), under isocratic elution with 50% ethanol/heptanes at 9 mL/min. The enantiomers were baseline separated. Retention time—faster enantiomer: 83c F, T=27.3 min; slower enantiomer: 83c S, T=32.9 min.

Example 83d F and S

Preparation of pure enantiomers; 5-chloro-2-[4-((1R,2S)-2-{2-[3-fluoro-4-(1H-tetrazol-1-yl)phenoxy]ethyl}cyclopropyl)piperidin-1-yl]pyrimidine and 5-chloro-2-[4-((1S,2R)-2-{2-[3-fluoro-4-(1H-tetrazol-1-yl)phenoxy]ethyl}cyclopropyl)piperidin-1-yl]pyrimidine

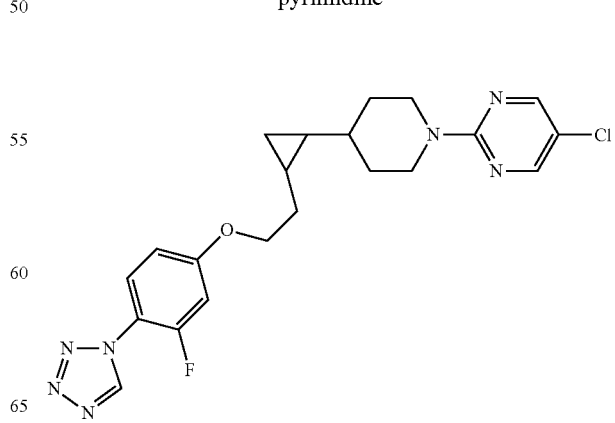

rac cis-5-chloro-2-[4-(2-{2-[3-fluoro-4-(1H-tetrazol-1-yl)phenoxy]ethyl}cyclopropyl)piperidin-1-yl]pyrimidine from Example 30b (45 mg) was dissolved in 5 mL ethanol. The solution was subjected to HPLC separation on a semi-prep chiralpak IA column (20×250 mm, 5μ), under isocratic elution with 75% ethanol/heptanes at 9 mL/min. The enantiomers were baseline separated. Retention time—faster enantiomer: 83d F, T=21.9 min; slower enantiomer: 83d S, T=26.2 min Example 83e F and S Preparation of pure enantiomers; 5-fluoro-2-[4-((1R,2S)-2-{2-[3-fluoro-4-(5-methyl-1,3,4-oxadiazol-2-yl)phenoxy]ethyl}cyclopropyl)piperidin-1-yl]pyrimidine and 5-fluoro-2-[4-((1S,2R)-2-{2-[3-fluoro-4-(5-methyl-1,3,4-oxadiazol-2-yl)phenoxy]ethyl}cyclopropyl)piperidin-1-yl]pyrimidine rac cis-5-fluoro-2-[4-(2-{2-[3-fluoro-4-(5-methyl-1,3,4-oxadiazol-2-yl)phenoxy]ethyl}cyclopropyl)piperidin-1-yl]pyrimidine from Example 86 (35 mg) was dissolved in 3.5 mL ethanol. The solution was subjected to HPLC separation on a semi-prep chiralpak TA column (20×250 mm, 5μ), under isocratic elution with 50% ethanol/heptanes at 9 mL/min, 3 injections. The enantiomers were baseline separated. Retention time—faster enantiomer: 83e F, T=20.68 min; slower enantiomer: 83e S, T=25.21 min Example 84

Preparation of rac-cis-2-[4-(2-{2-[3-fluoro-4-(5-methyl-1,3,4-oxadiazol-2-yl)phenoxy]ethyl}cyclopropyl)piperidin-1-yl]-5-methylpyrimidine Step 1: rac-cis-tert-Butyl 4-(2-{2-[3-fluoro-4-(5-methyl-1,3,4-oxadiazol-2-yl)phenoxy]ethyl}cyclopropyl)piperidine-1-carboxylate

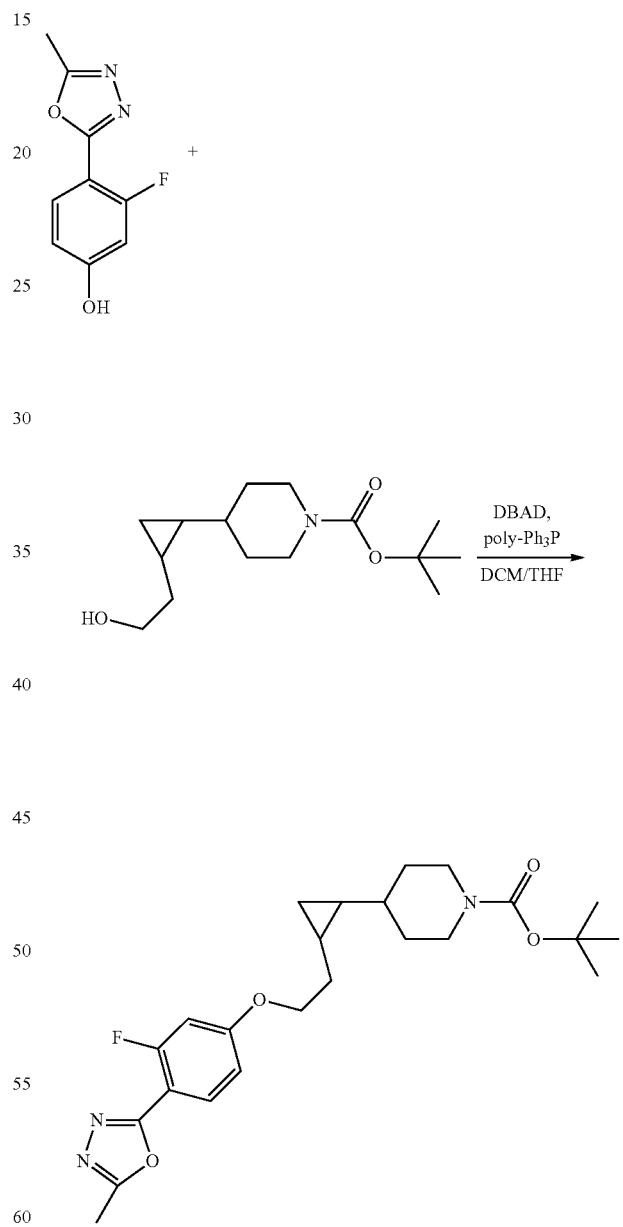

The title compound was synthesized using rac-tert-butyl 4-[2-(2-hydroxyethyl)cyclopropyl]piperidine-1-carboxylate from Example 1 and 3-fluoro-4-(5-methyl-1,3,4-oxadiazol-2-yl)phenol through a Mitsunobu reaction by a procedure analogous to that procedure reported for Example 6, step 3.

Step 2: rac-cis-5-Methyl-2-[4-(2-{2-[3-fluoro-4-(5-methyl-1,3,4-oxadiazol-2-yl)phenoxy]ethyl}cyclopropyl)piperidin-1-yl]pyrimidine

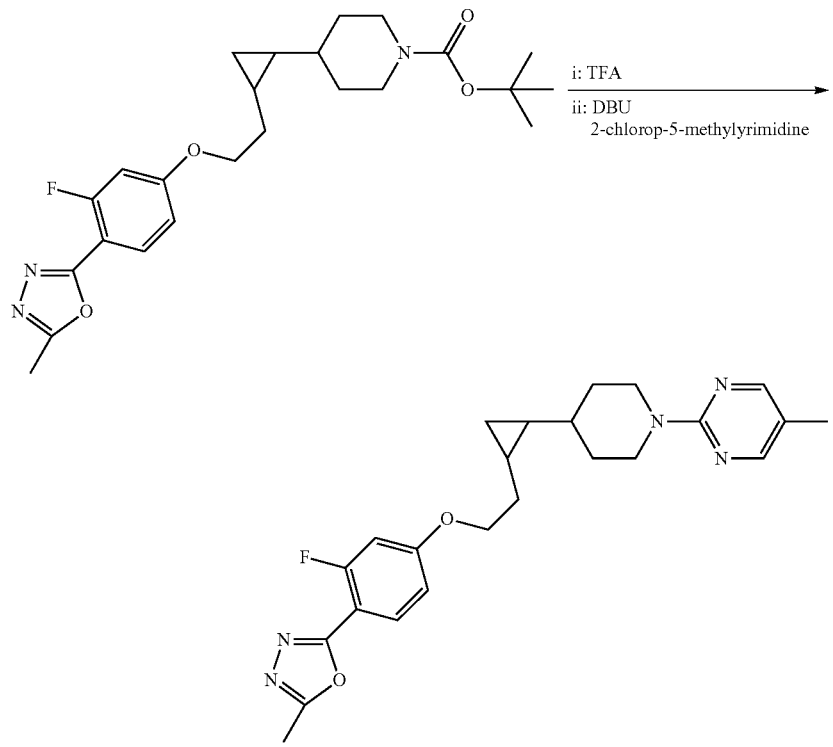

rac-cis-tert-Butyl 4-(2-{2-[3-fluoro-4-(5-methyl-1,3,4-oxadiazol-2-yl)phenoxy]ethyl}cyclopropyl)piperidine-1-carboxylate from step 1 of this example (40 mg, 0.09 mmol) was dissolved in 0.5 mL dichloromethane. TFA (0.5 mL) was carefully added. The mixture was stirred at room temperature for 20 min, upon which the volatile TFA was removed in vacuo and further dried i. vac. for 2 hours. The residue was redissolved in 1 mL NMP. 2-Chloro-5-methylpyrimidine (23 mg, 0.18 mmol) and DBU (0.135 mL, 0.9 mmol) were sequentially added. The mixture was heated at 90° C. for 1.5 hours before cooled back to room temperature. The reaction was then diluted with 2 mL water and 0.5 mL EtOAc. The aqueous phase was further extracted twice with ethyl acetate. The combined organic layers were washed with water and brine, then concentrated and purified by column chromatography through a 12 gram biotage silica gel cartridge eluting with 20% ethyl acetate/hexanes to give the product as white-solid. LRMS talc: 437.2; obs: 438.7 (M+1).

Compounds Reported in Table 2 are Prepared by a General Procedure Analogous to that Described in Example 84 Above.

TABLE 2

| Examples | Chemical name | Chemical Structure | (M + 1) |
| --- | --- | --- | --- |
| Example 85 | Rac-cis-2-[4-(2-{2-[3-fluoro-4-(5-methyl-1,3,4-oxadiazol-2-yl)phenoxy]ethyl}cyclopropyl)piperidin-1-yl]pyrimidine | 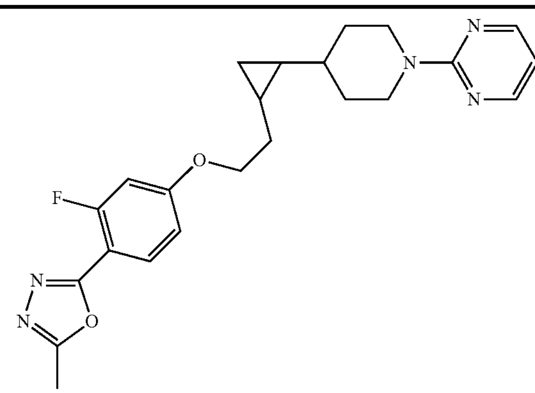 | 424.6 |

TABLE 2-continued

| Examples | Chemical name | Chemical Structure | (M + 1) |
|---|---|---|---|
| Example 86 | Rac-cis-5-fluoro-2-[4-(2-{2-[3-fluoro-4-(5-methyl-1,3,4-oxadiazol-2-yl)phenoxy]ethyl}cyclopropyl)piperidin-1-yl]pyrimidine | 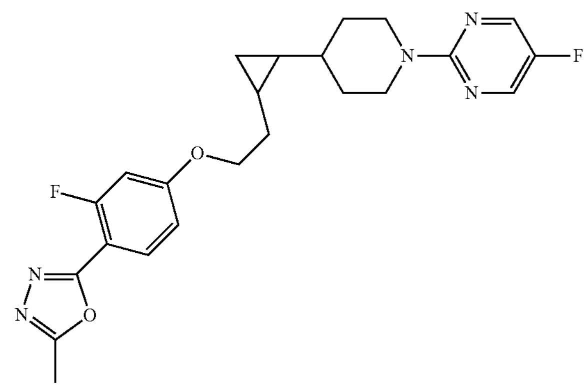 [SMILES: Cc1nnc(-c2ccc(OCCC3CC3C3CCN(c4ncc(F)cn4)CC3)cc2F)o1] | 442.6 |
| Example 87 | Rac-cis-5-chloro-2-[4-(2-{2-[3-fluoro-4-(5-methyl-1,3,4-oxadiazol-2-yl)phenoxy]ethyl}cyclopropyl)piperidin-1-yl]-4-methylpyrimidine | 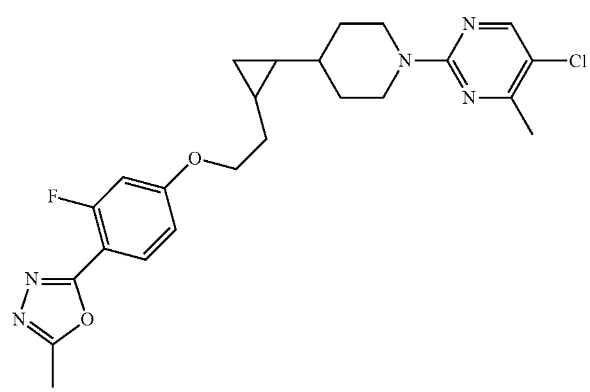 [SMILES: Cc1nnc(-c2ccc(OCCC3CC3C3CCN(c4ncc(Cl)c(C)n4)CC3)cc2F)o1] | 472.2 |
| Example 88 | Rac-cis-3,5-dichloro-2-[4-(2-{2-[3-fluoro-4-(5-methyl-1,3,4-oxadiazol-2-yl)phenoxy]ethyl}cyclopropyl)piperidin-1-yl]pyridine | 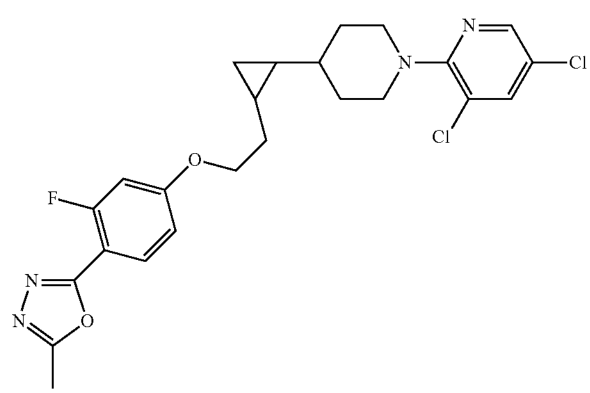 [SMILES: Cc1nnc(-c2ccc(OCCC3CC3C3CCN(c4ncc(Cl)cc4Cl)CC3)cc2F)o1] | 491.6 |
| Example 89 | Rac-cis-2-[4-(2-{2-[3-fluoro-4-(5-methyl-1,3,4-oxadiazol-2-yl)phenoxy]ethyl}cyclopropyl)piperidin-1-yl]-5-(trifluoromethyl)pyridinium trifluoroacetate | 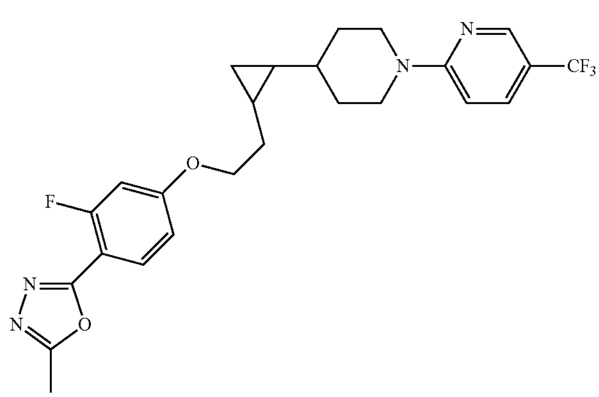 [SMILES: Cc1nnc(-c2ccc(OCCC3CC3C3CCN(c4ccc(C(F)(F)F)cn4)CC3)cc2F)o1] | 491.7 |

Example 90

Preparation of rac-trans-5-chloro-2-[4-(2-{2-[4-(methylsulfonyl)phenoxy]ethyl}cyclopropyl)piperidin-1-yl]pyrimidine Step 1: rac-trans-2-{2-[1-(5-chloropyrimidin-2-yl)piperidin-4-yl]cyclopropyl}ethanol

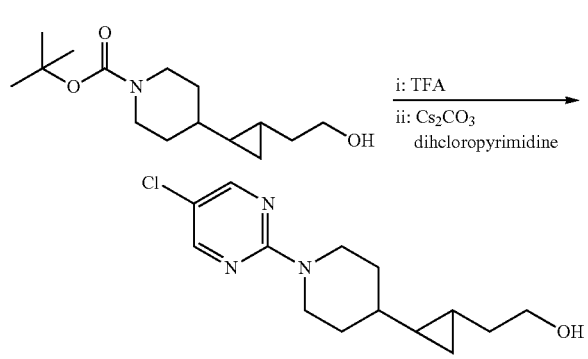

The title compound was prepared from trans rac-trans-tert-butyl 4-[2-(2-hydroxyethyl)cyclopropyl]piperidine-1-carboxylate prepared in Example 3 by a general procedure analogous to that reported in Example 6, Step 2.

Step 2: rac-trans-5-chloro-2-[4-(2-{2-[4-(methylsulfonyl)phenoxy]ethyl}cyclopropyl)piperidin-1-yl]pyrimidine

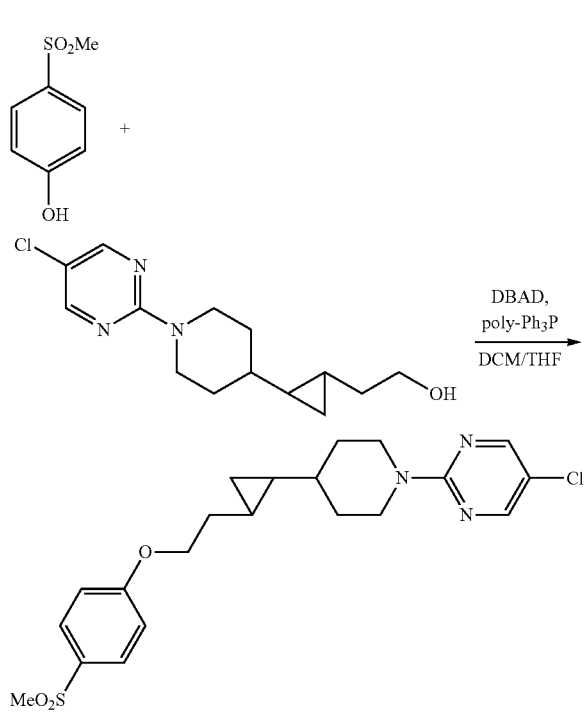

The title compound was prepared from the product of Example 90, step 1, by a general procedure analogous to that reported in Example 6, Step 3. LRMS calc: 435.1; obs: 436.3 (M+1).

Example 91

Preparation of 5-chloro-2-[4-((1R,2R)-2-{2-[4-(methylsulfonyl)phenoxy]ethyl}cyclopropyl)piperidin-1-yl]pyrimidine

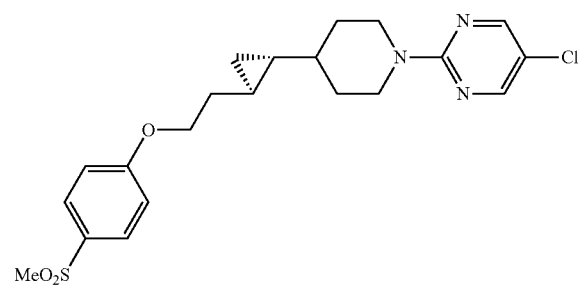 [SMILES: CS(=O)(=O)c1ccc(OCC[C@H]2C[C@@H]2C2CCN(c3ncc(Cl)cn3)CC2)cc1]

The title compound was obtained by chromatographic resolution on chiral stationary phase. Racemic-5-Chloro-2-[4-(2-{2-[4-(methylsulfonyl)phenoxy]ethyl}cyclopropyl)piperidin-1-yl]pyrimidine, prepared in Example 90 above, was separated on a preparative HPLC column by a method analogous to Example 83 above.

Example 92

Preparation of rac-trans-5-chloro-2-(4-{2-[2-(pyridin-4-yloxy)ethyl]cyclopropyl}piperidin-1-yl)pyrimidine

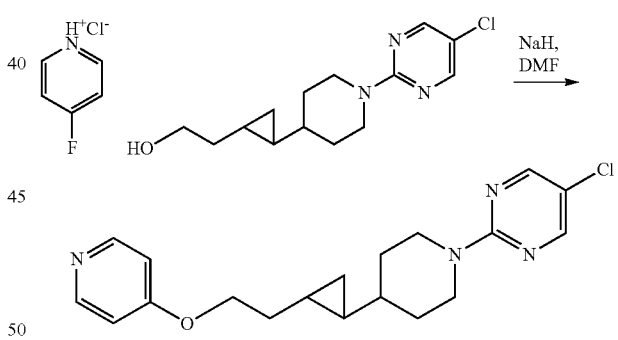

Sodium hydride (100%, 20 mg, 0.85 mmol) was weighed into a vial, DMF (anhydrous, 2.1 mL) was added, followed by addition of rac-trans 2-{2-[1-(5-chloropyrimidin-2-yl)piperidin-4-yl]cyclopropyl}ethanol (60 mg, 0.21 mmol) and the mixture stirred at room temperature for 5 min. The 4-fluoropyridinium chloride was then added and stirred at room temperature for 10 min. The mixture was heated to 50° C. for 1.5 hours, cooled to room temperature, and diluted with ethyl acetate (5 mL), quenched with saturated aq.NH$_4$Cl (5 mL), dried over MgSO$_4$, filtered and concentrated. The crude residue was purified by silica gel chromatography (30% ethyl acetate/hexane) to yield the titled compound as a white solid. LC-MS (M+1): 359.54.

Compounds Reported in Table 3 are Prepared by a General Procedure Analogous to that Described in Example 6, Steps 1 and 2, Described Above

TABLE 3

| Examples | Chemical name | Chemical Structure | (M + 1) |
| --- | --- | --- | --- |
| Example 93 | 4-(2-{(1R,2R)-2-[1-(5-chloropyrimidin-2-yl)piperidin-4-yl]cyclopropyl} ethoxy)-N-cyclopropyl-2-fluorobenzamide | 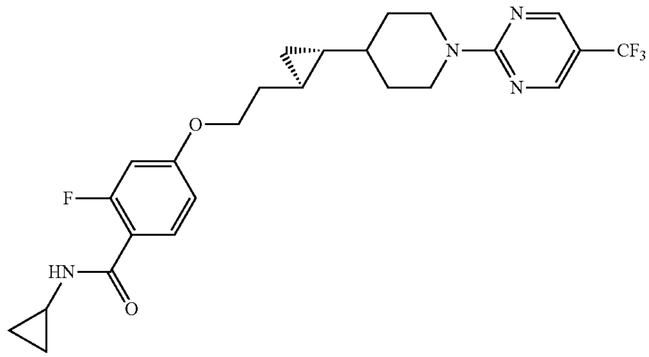 [SMILES: O=C(NC1CC1)c1ccc(OCC[C@H]2C[C@@H]2C2CCN(c3ncc(C(F)(F)F)cn3)CC2)cc1F] | 459.6 |
| Example 94 | 4-(2-{(1R,2R)-2-[1-(5-chloropyrimidin-2-yl)piperidin-4-yl]cyclopropyl} ethoxy)-2-fluorobenzonitrile | 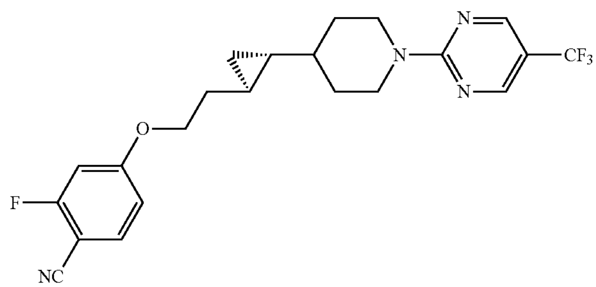 [SMILES: N#Cc1ccc(OCC[C@H]2C[C@@H]2C2CCN(c3ncc(C(F)(F)F)cn3)CC2)cc1F] | 401.6 |
| Example 95 | 5-chloro-2-[4-((1R,2R)-2-{2-[4-(1H-1,2,4-triazol-1-yl)phenoxy]ethyl} cyclopropyl)piperidin-1-yl]pyrimidine | 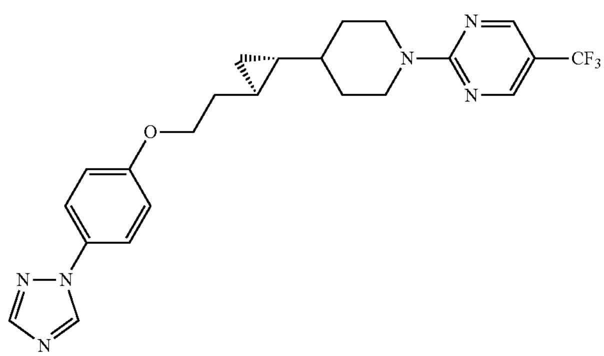 [SMILES: FC(F)(F)c1cnc(N2CCC([C@H]3C[C@@H]3CCOc3ccc(-n4cncn4)cc3)CC2)nc1] | 425.6 |
| Example 96 | 5-chloro-2-[4-((1R,2R)-2-{2-[3-fluoro-4-(5-methyl-1,3,4-oxadiazol-2-yl)phenoxy]ethyl} cyclopropyl)piperidin-1-yl]pyrimidine | 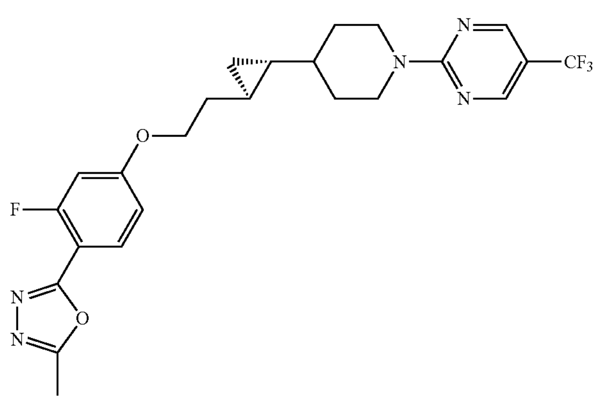 [SMILES: Cc1nnc(-c2ccc(OCC[C@H]3C[C@@H]3C3CCN(c4ncc(C(F)(F)F)cn4)CC3)cc2F)o1] | 458.6 |

TABLE 3-continued

| Examples | Chemical name | Chemical Structure | (M + 1) |
|---|---|---|---|
| Example 97 | 5-chloro-2-[4-((1R,2R)-2-{2-[4-(5-cyclopropyl-1,3,4-oxadiazol-2-yl)-3-fluorophenoxy]ethyl}cyclopropyl)piperidin-1-yl]pyrimidine | 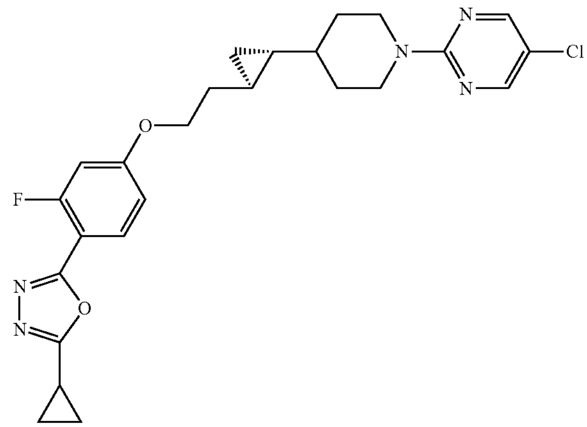 [SMILES: Fc1cc(OCC[C@H]2C[C@@H]2C2CCN(c3ncc(Cl)cn3)CC2)ccc1-c1nnc(C2CC2)o1] | 242.9 (M + 2)/2 |
| Example 98 | rac-trans-5-chloro-2-(4-{2-[2-(pyridin-4-yloxy)ethyl]cyclopropyl}piperidin-1-yl)pyrimidine | 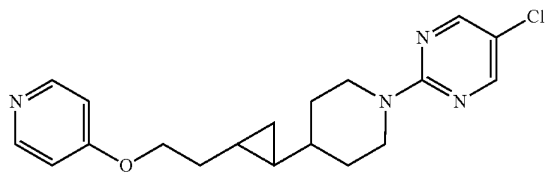 [SMILES: Clc1cnc(N2CCC(C3CC3CCOc3ccncc3)CC2)nc1] | 359.54 |
| Example 99 | rac-trans-4-{2-{2-[1-(5-chloropyrimidin-2-yl)piperidin-4-yl]cyclopropyl}ethoxy)-6-methylpyrimidine-2-carbonitrile | 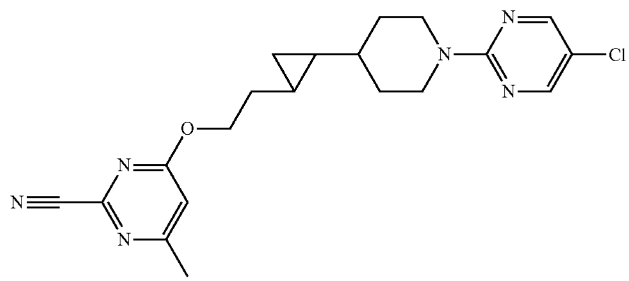 [SMILES: Cc1cc(OCCC2CC2C2CCN(c3ncc(Cl)cn3)CC2)nc(C#N)n1] | 399.58 |
| Example 100 | rac trans 6-(2-{2-[1-(5-chloropyrimidin-2-yl)piperidin-4-yl]cyclopropyl}ethoxy)-2-methylpyrimidine-4-carbonitrile | 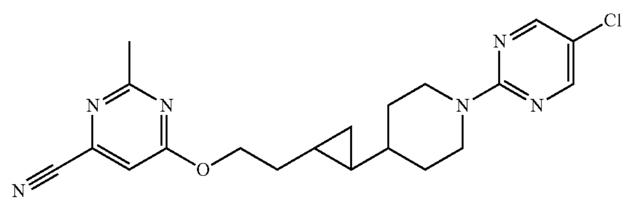 [SMILES: Cc1nc(C#N)cc(OCCC2CC2C2CCN(c3ncc(Cl)cn3)CC2)n1] | 399.56 |

Example 101

Preparation of rac-trans-5-chloro-2-{4-[(2-{[4-(methylsulfonyl)phenoxy]methyl}cyclopropyl)methyl]piperidin-1-yl}pyrimidine

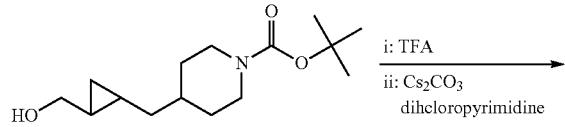

i: TFA
ii: Cs₂CO₃
dihcloropyrimidine

-continued

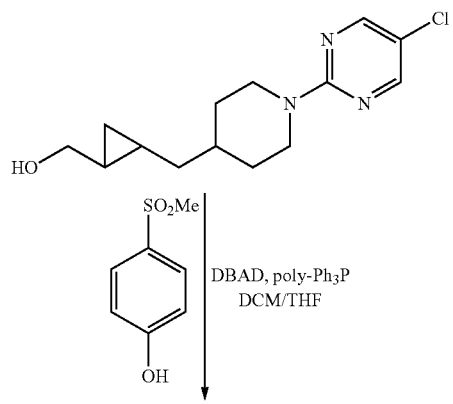

DBAD, poly-Ph₃P
DCM/THF

-continued

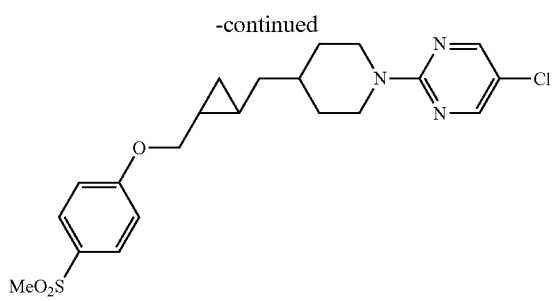

The title compound was prepared from rac trans tert-butyl 4-{[2-(hydroxymethyl)cyclopropyl]methyl}piperidine-1-carboxylate of Example 4 by a general procedure analogous to those reported for Example 6 steps 1 through 3.

Example 102

Preparation of 5-chloro-2-[4-((1R,2R)-2-{2-[4-(methylsulfonyl)phenoxy]ethyl}cyclopropyl)piperidin-1-yl]pyrimidine

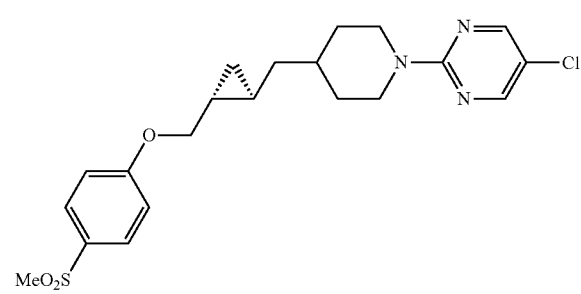 [SMILES: CS(=O)(=O)c1ccc(OC[C@@H]2C[C@H]2CC2CCN(c3ncc(Cl)cn3)CC2)cc1]

The title compound was prepared from tert-butyl 4-{[(1R,2R)-2-(hydroxymethyl)cyclopropyl]methyl}piperidine-1-carboxylate of Example 4 by a general procedure analogous to those reported for Example 6 steps 1 through 3.

Example 103

Preparation of 5-chloro-2-{4-[((1S,2S)-2-{[4-(methylsulfonyl)phenoxy]methyl}cyclopropyl)methyl]piperidin-1-yl}pyrimidine The title compound was prepared from tert-butyl 4-{[(1S,2S)-2-(hydroxymethyl)cyclopropyl]methyl}piperidine-1-carboxylate of Example 4 by a general procedure analogous to those reported for Example 6 steps 1 through 3.

Compounds reported in Table 4 are prepared by a general procedure analogous to that described in Examples 101, 102 and 103 above

TABLE 4

| Examples | Chemical name | Chemical Structure | (M + 1) |
|---|---|---|---|
| Example 104 | Rac-trans-4-[(2-{[1-(5-chloropyrimidin-2-yl)piperidin-4-yl]methyl}cyclopropyl)methoxy]-2-fluorobenzonitrile | 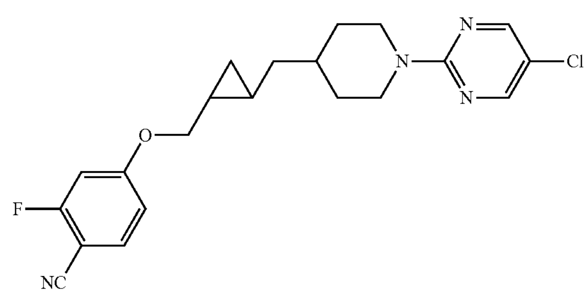 [SMILES: N#Cc1ccc(OCC2CC2CC2CCN(c3ncc(Cl)cn3)CC2)cc1F] | 401.4 |
| Example 105 | 4-[((1R,2R)-2-{[1-(5-chloropyrimidin-2-yl)piperidin-4-yl]methyl}cyclopropyl)methoxy]-2-fluorobenzonitrile | 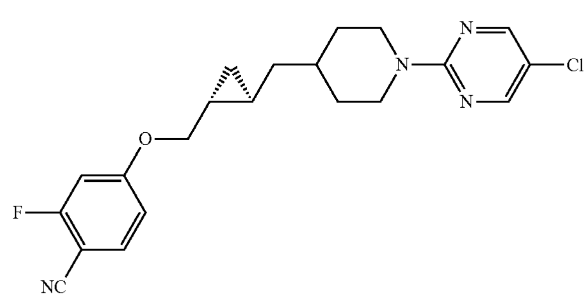 [SMILES: N#Cc1ccc(OC[C@@H]2C[C@H]2CC2CCN(c3ncc(Cl)cn3)CC2)cc1F] | 401.6 |

TABLE 4-continued

| Examples | Chemical name | Chemical Structure | (M + 1) |
| --- | --- | --- | --- |
| Example 106 | Rac-trans 4-[(2-{[1-(5-chloropyrimidin-2-yl)piperidin-4-yl]methyl}cyclopropyl)methoxy]-N-cyclopropyl-2-fluorobenzamide | 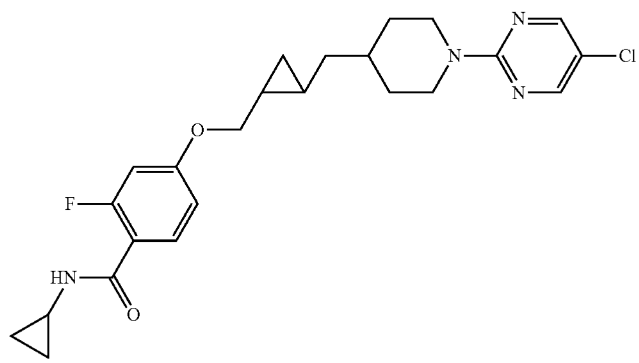 [SMILES: O=C(NC1CC1)c1ccc(OCC2CC2CC2CCN(c3ncc(Cl)cn3)CC2)cc1F] | 459.2 |
| Example 107 | 4-[((1R,2R)-2-{[1-(5-chloropyrimidin-2-yl)piperidin-4-yl]methyl}cyclopropyl)methoxy]-N-cyclopropyl-2-fluorobenzamide | 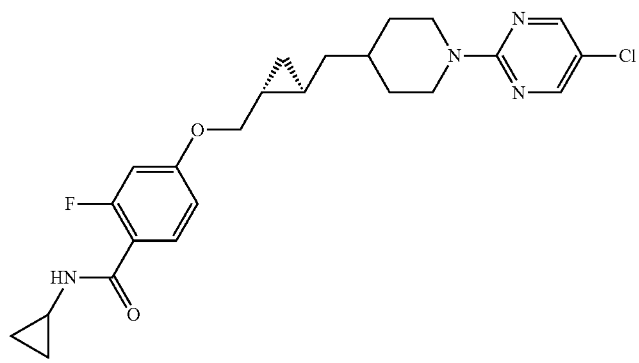 [SMILES: O=C(NC1CC1)c1ccc(OC[C@@H]2C[C@H]2CC2CCN(c3ncc(Cl)cn3)CC2)cc1F] | 459.6 |
| Example 108 | 4-[((1S,2S)-2-{[1-(5-chloropyrimidin-2-yl)piperidin-4-yl]methyl}cyclopropyl)methoxy]-N-cyclopropyl-2-fluorobenzamide | 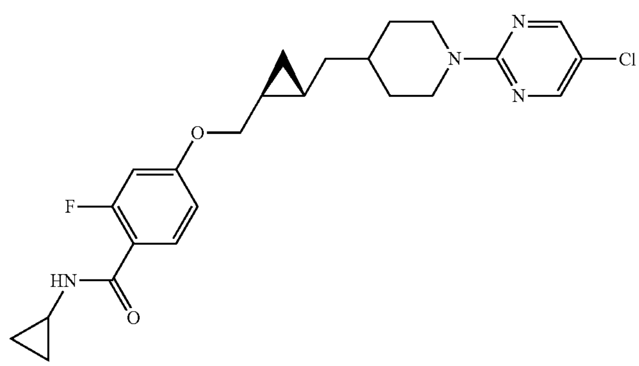 [SMILES: O=C(NC1CC1)c1ccc(OC[C@H]2C[C@@H]2CC2CCN(c3ncc(Cl)cn3)CC2)cc1F] | 459.6 |
| Example 109 | 5-chloro-2-{4-[((1R,2R)-2-{[3-fluoro-4-(5-methyl-1,3,4-oxadiazol-2-yl)phenoxy]methyl}cyclopropyl)methyl]piperidin-1-yl}pyrimidine | 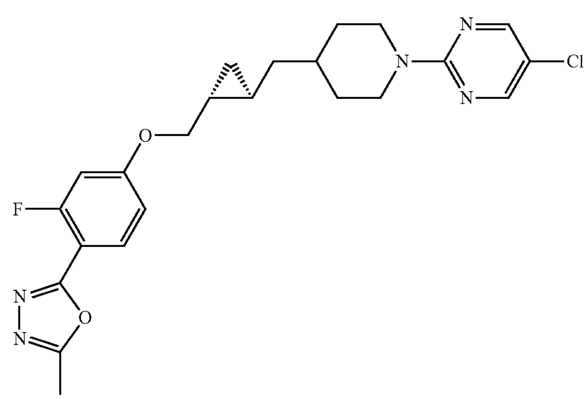 [SMILES: Cc1nnc(-c2ccc(OC[C@@H]3C[C@H]3CC3CCN(c4ncc(Cl)cn4)CC3)cc2F)o1] | 458.6 |

TABLE 4-continued

| Examples | Chemical name | Chemical Structure | (M + 1) |
|---|---|---|---|
| Example 110 | 5-chloro-2-{4-[((1S,2S)-2-{[3-fluoro-4-(5-methyl-1,3,4-oxadiazol-2-yl)phenoxy]methyl}cyclopropyl)methyl]piperidin-1-yl}pyrimidine | 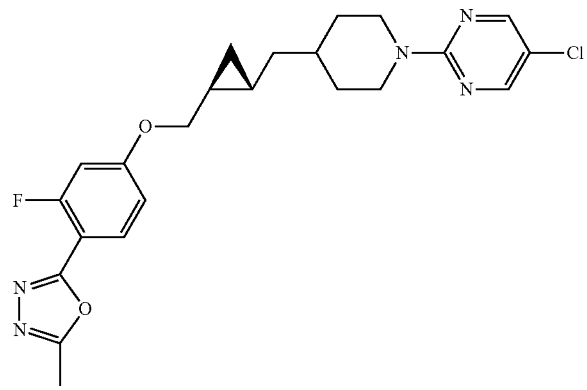 [SMILES: Cc1nnc(-c2ccc(OC[C@H]3C[C@@H]3CC3CCN(c4ncc(Cl)cn4)CC3)cc2F)o1] | 458.6 |
| Example 111 | rac-trans 5-chloro-2-{4-[(2-{[4-(5-cyclopropyl-1,3,4-oxadiazol-2-yl)-3-fluorophenoxy]methyl}cyclopropyl)methyl]piperidin-1-yl}pyrimidine. | 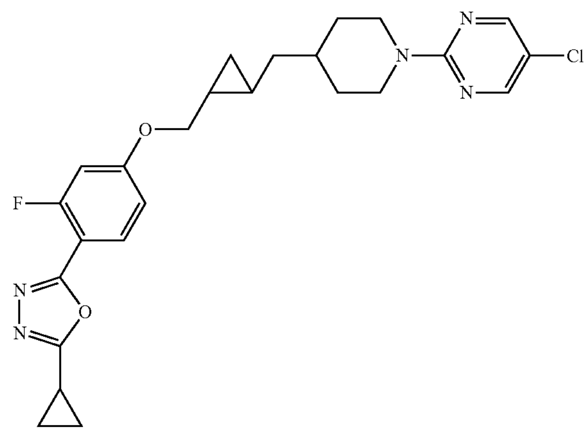 [SMILES: Fc1cc(OCC2CC2CC2CCN(c3ncc(Cl)cn3)CC2)ccc1-c1nnc(C2CC2)o1] | 484.6 |
| Example 112 | 4-[((1S,2S)-2-{[1-(5-chloropyrimidin-2-yl)piperidin-4-yl]methyl}cyclopropyl)methoxy]benzenesulfonamide | 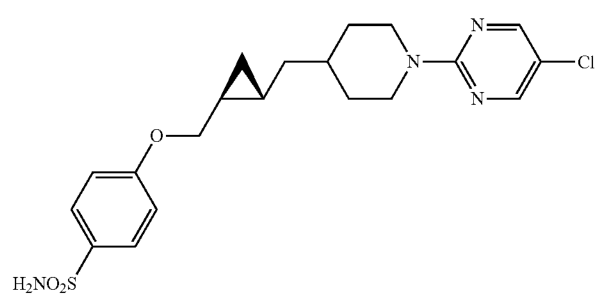 [SMILES: NS(=O)(=O)c1ccc(OC[C@H]2C[C@@H]2CC2CCN(c3ncc(Cl)cn3)CC2)cc1] | 437.7 |
| Example 113 | rac-trans-6-[(2-{[1-(5-chloropyrimidin-2-yl)piperidin-4-yl]methyl}cyclopropyl)methoxy]-2-methylpyrimidine-4-carbonitrile | 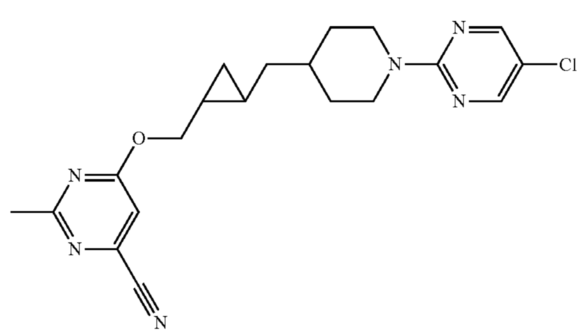 [SMILES: Cc1nc(C#N)cc(OCC2CC2CC2CCN(c3ncc(Cl)cn3)CC2)n1] | 399.67 |

TABLE 4-continued

| Examples | Chemical name | Chemical Structure | (M + 1) |
|---|---|---|---|
| Example 114 | rac-trans-4-[(2-{[1-(5-chloropyrimidin-2-yl)piperidin-4-yl]methyl}cyclopropyl)methoxy]-6-methylpyrimidine-2-carbonitrile | 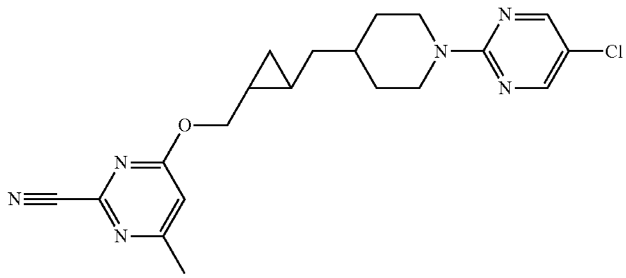 [SMILES: Cc1cc(OCC2CC2CC2CCN(c3ncc(Cl)cn3)CC2)nc(C#N)n1] | 399.69 |
| Example 115 | rac-trans-4-[((1S,2S)-2-{[1-(5-chloropyrimidin-2-yl)piperidin-4-yl)methyl}cyclopropyl)methoxy]-3-fluorobenzonitrile | 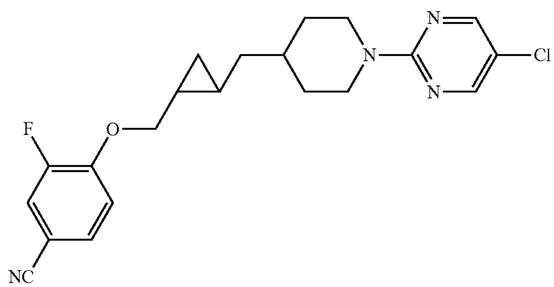 [SMILES: N#Cc1ccc(OCC2CC2CC2CCN(c3ncc(Cl)cn3)CC2)c(F)c1] | 401.5 |

Example 116

Preparation of rac-cis-5-chloro-2-{-4-[(2-{[4-(methylsulfonyl)phenoxy]methyl}cyclopropyl)methyl]piperidin-1-yl}pyrimidine

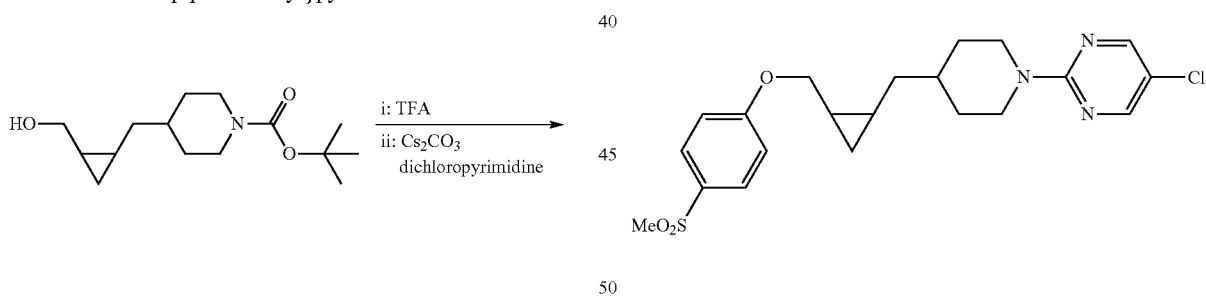

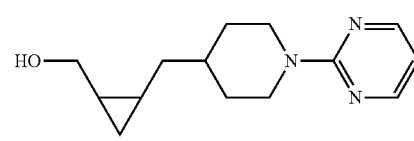

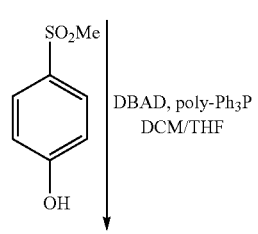

The title compound was prepared from the protected rac cis tert-butyl 4-{[2-(hydroxymethyl)cyclopropyl]methyl}piperidine-1-carboxylate of Example 5 by a general procedure analogous to those reported for Example 6 steps 1 through 3.

Compounds Reported in Table 5 are Prepared Using Phenols Described Elsewhere in the Examples by General Procedure Described in Example 116 Above

TABLE 5

| Examples | Chemical name | Chemical Structure | (M + 1) |
|---|---|---|---|
| Example 117 | rac-cis 4-[(2-{[1-(5-chloropyrimidin-2-yl)piperidin-4-yl]methyl}cyclopropyl)methoxy]-N-cyclopropyl-2-fluorobenzamide | 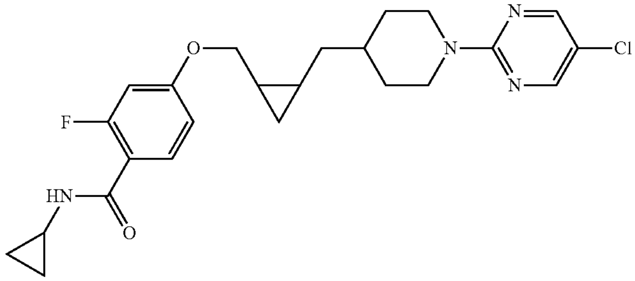 [SMILES: O=C(NC1CC1)c1ccc(OCC2CC2CC2CCN(c3ncc(Cl)cn3)CC2)cc1F] | 459.6 |
| Example 118 | rac-cis-4-[(2-{[1-(5-chloropyrimidin-2-yl)piperidin-4-yl]methyl} cyclopropyl) methoxy]-6-methylpyrimidine-2-carbonitrile | 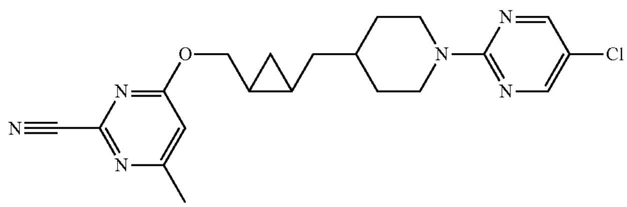 [SMILES: Cc1cc(OCC2CC2CC2CCN(c3ncc(Cl)cn3)CC2)nc(C#N)n1] | 399.59 |
| Example 119 | rac-cis 4-[(2-{[1-(5-chloropyrimidin-2-yl)piperidin-4-yl]methyl} cyclopropyl)methoxy]-2-fluorobenzonitrile | 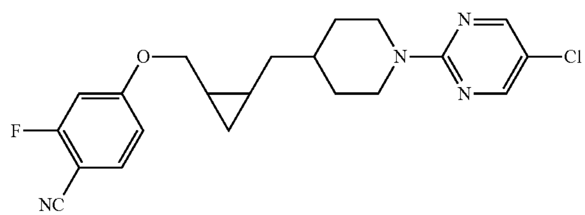 [SMILES: N#Cc1ccc(OCC2CC2CC2CCN(c3ncc(Cl)cn3)CC2)cc1F] | 401.6 |

Example 120

Preparation of 5-chloro-2-{4-[(1R,2S)-2-(2-{[5-(1H-1,2,3-triazol-1-yl)pyridin-2-yl]oxy}ethyl)cyclopropyl]piperidin-1-yl}pyrimidine

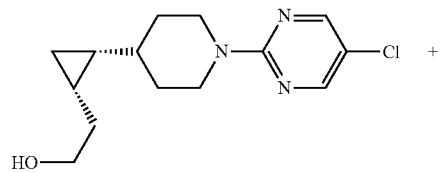

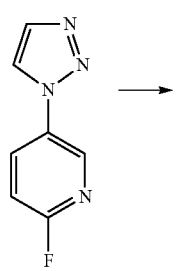

→

-continued

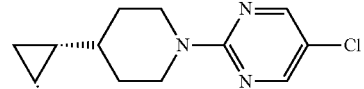

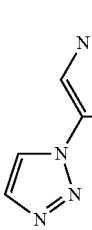

A suspension of NaH (720 mg; 60 wt %; 432 mg NaH contained; 17.99 mmol) in DMF (9 mL) at 0° C. was treated with a solution of 2-{(1S,2R)-2-[1-(5-chloropyrimidin-2-yl)piperidin-4-yl]cyclopropyl}ethanol (3.9 g; 13.84 mmol) in DMF (9 mL). The mixture was stirred at 0° C. for 30 minutes. The mixture was treated with a solution of 2-fluoro-5-(1H-1,2,3-triazol-1-yl)pyridine (2.499 g; 15.22 mmol) in DMF (10 mL). The reaction was stirred at 0° C. for 45 minutes, then allowed to warm to room temperature and stirred overnight. The reaction was quenched with saturated aqueous NH₄Cl and the mixture partitioned between ethyl acetate and water. The organic layer was washed twice more with water, dried over sodium sulfate, filtered and evaporated to a residue. The residue was chromatographed (Horizon 65i silica cartridge; 30% to 45% ethyl acetate/heptane). The fractions containing the desired product were combined and evaporated to a white solid. Crystalline solid was also recovered from the chromatography fractions. The solid isolated from chromatography was recrystallized from EtOH/heptane. The solid (4 g) was suspended in EtOH (150 ml), then heated until completely dissolved, allowed to cool to RT and heptane (100 ml) was added. The mixture was aged at RT overnight, cooled to 0° C. for 5 minutes and filtered to provide the title compound). LCMS: calc. 425.17 obs: 426.09 (M+1). $^1$H NMR (CDCl$_3$): δ 8.48 (d, 1H), 8.20 (s, 2H), 7.97 (dd, 1H), 7.93 (s, 1H), 7.87 (s, 1H), 7.26 (s, CDCl3), 6.89 (d, 1H), 4.47 (br t, 2H), 4.47 (t, 2H), 2.87 (m, 2H), 2.15 (m, 1H), 1.86 (br t, 2H), 1.58 (m, 1H), 1.57 (S, H2O), 1.37 (m, 2H), 1.12 (m, 1H), 0.94 (m, 1H), 0.70 (m, 1H), 0.61 (m, 1H), −0.08 (q, 1H).

Example 121

Preparation of 2-methyl-6-(2-{(1S,2R)-2-[1-(5-methylpyrimidin-2-yl)piperidin-4-yl]cyclopropyl}ethoxy)pyrimidine-4-carbonitrile

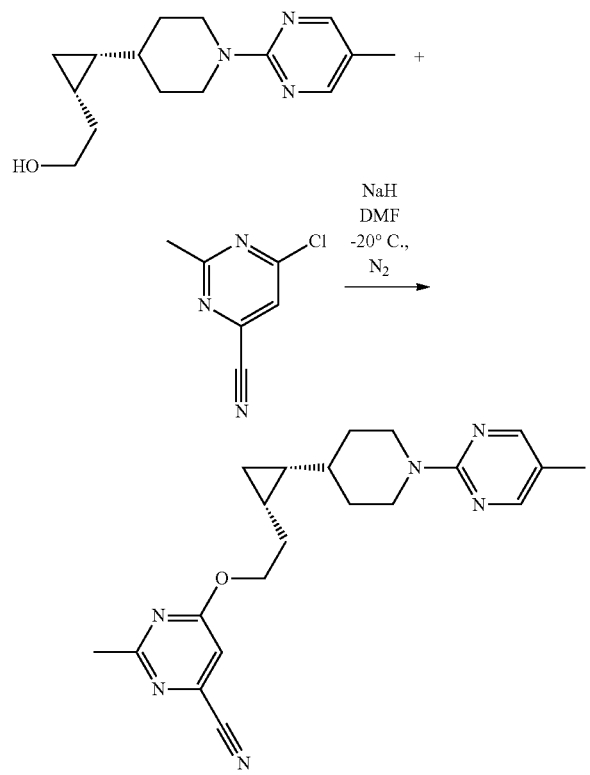

NaH (60%, 18 mg, 0.45 mmol, 1.2 eq) was placed in a 1 dram vial and DMF (1.2 mL) added. A solution of 2-{(1S,2R)-2-[1-(5-methylpyrimidin-2-yl)piperidin-4-yl]cyclopropyl}ethanol (100 mg, 0.375 mmol) was added drop-wise (0.5 mL) to the slurry, and the mixture stirred at RT for 10 min. The solution was cooled to −20° C., and a solution of 6-chloro-2-methylpyrimidine-4-carbonitrile (115 mg, 0.75 mmol) in DMF (0.5 mL) was added drop-wise. The red mixture was stirred for 40 minutes. A solution of ice-cold saturated NH$_4$Cl (aq., 1 mL) was added, and the mixture diluted with EtOAc (100 mL) and water (50 mL). The mixture was transferred to a separatory funnel, the mixture shaken, and the layers separated. The organic fraction was washed with water (20 mL), dried over MgSO$_4$, filtered, and concentrated in vac. The red oil was purified by chromatography on silica gel 1:7 EtOAc:Hexanes to give the title compound.

LC-MS: calc: 378.22 obs: 379.03 (M+1).

Measurement of GPR119 Signaling Using a Cyclic AMP (cAMP) Homogenous Time Resolved Fluorescence (HTRF) Assay Chinese hamster ovary (CHO) cell lines stably transfected with the permissive guanine nucleotide binding protein alpha 15 (Gα15) and marine GPR119 were maintained in DMEM media containing FBS, penicillin-streptomycin, puromycin, and G418 (geneticin). Alternatively, human embryonic kidney (HEK)293 Flp-In cells (Invitrogen, Carlsbad, Calif.) were stably transfected with a human SNP variant (S309L) of GPR119 and maintained in DMEM media containing FBS, penicillin-streptomycin, and hygromycin. Agonist activation of the GPR119 receptor was measured in receptor transfected cells described above, treated with compounds of this invention, using a commercial homogenous time resolved fluorescence (HTRF) kit for measurement of cAMP (CisBio, Bedford, Mass.). The assay was performed in 96-well half-volume plates (murine) or 384-well plates (human) following the manufacturers instructions. Briefly, suspended cells were incubated with a dose titration of test compound at room temperature for 60 min, lysed, and incubated with HTRF reagents for an additional 60 min. The plate was read using an Envision multilabel reader (Perkin Elmer) adjusted to read time resolved fluorescence and the cAMP concentrations were extrapolated from a cAMP calibration curve. GPR119 agonists will exhibit a concentration-dependent increase in intracellular cAMP. The concentration of test compound required to stimulate a half-maximal response (EC50), and efficacy as compared to an internal agonist control, was determined from a sigmoidal 4-parameter curve fit of the resulting plot of normalized activity versus compound concentration.

The Examples of this case show inflection points, denoted as $EC_{50}$ values, less than 1000 nM when tested in the above assays, as noted in the table below.

Activity is denoted as; $EC_{50}<10$ nM #, 10 nM$<EC_{50}<50$ nM ##, 50 nM$<EC_{50}<200$ nM ###, 200 nM$<EC_{50}$ ####

| | |
|---|---|
| Ex 6 | # |
| Ex 6a | # |
| Ex 7 | # |
| Ex 8 | #### |
| Ex 9 | ### |
| Ex 10 | #### |
| Ex 11 | # |
| Ex 12 | ## |
| Ex 13 | ## |
| Ex 14 | # |
| Ex 15 | ## |
| Ex 16 | # |
| Ex 17 | ### |
| Ex 18 | ### |
| Ex 19 | ## |
| Ex 20 | ### |
| Ex 21 | ## |
| Ex 22 | ## |
| Ex 23 | ### |
| Ex 24 | ### |
| Ex 25 | ## |
| Ex 26 | ## |
| Ex 27 | # |
| Ex 27b | |
| Ex 27c | ## |
| Ex 28 | ### |
| Ex 29 | #### |
| Ex 30 | # |
| Ex 30b | # |
| Ex 30d | # |
| Ex 30e | # |
| Ex 31 | ## |

| | |
|---|---|
| Ex 31a | # |
| Ex 31b | ## |
| Ex 32 | # |
| Ex 33 | # |
| Ex 34 | # |
| Ex 35 | ### |
| Ex 36 | ### |
| Ex 37 | # |
| Ex 38 | ## |
| Ex 39 | # |
| Ex 40 | # |
| Ex 41 | ## |
| Ex 42 | # |
| Ex 43 | # |
| Ex 44 | ## |
| Ex 45 | ## |
| Ex 46 | # |
| Ex 47 | # |
| Ex 48 | #### |
| Ex 49 | ### |
| Ex 50 | ### |
| Ex 51 | # |
| Ex 52 | # |
| Ex 53 | # |
| Ex 54 | ### |
| Ex 55 | ## |
| Ex 55a | # |
| Ex 83 F | # |
| Ex 83 S | # |
| Ex 83aF | ND |
| Ex 83aS | # |
| Ex 83bF | ### |
| Ex 83bS | # |
| Ex 83cF | # |
| Ex 83cS | # |
| Ex 83dF | ## |
| Ex 83dS | # |
| Ex 83eF | ### |
| Ex 83eS | # |
| Ex 84 | # |
| Ex 85 | # |
| Ex 86 | # |
| Ex 87 | # |
| Ex 88 | #### |
| Ex 89 | # |
| Ex 90 | ## |
| Ex 91 | ## |
| Ex 92 | ### |
| Ex 93 | # |
| Ex 94 | ### |
| Ex 95 | ## |
| Ex 96 | ## |
| Ex 97 | ## |
| Ex 98 | ### |
| Ex 99 | ## |
| Ex 100 | ## |
| Ex 101 | ### |
| Ex 102 | ### |
| Ex 103 | ## |
| Ex 104 | ### |
| Ex 105 | #### |
| Ex 106 | # |
| Ex 107 | ## |
| Ex 108 | ## |
| Ex 109 | ### |
| Ex 110 | ## |
| Ex 111 | ## |
| Ex 112 | ### |
| Ex 113 | ### |
| Ex 114 | ### |
| Ex 115 | ## |
| Ex 116 | #### |
| Ex 117 | ## |
| Ex 118 | ## |
| Ex 119 | #### |

Evaluation of Glucose Dependent Insulin Secretion (GDIS) in Static Isolated Mouse Islets.

Pancreatic islets of Langerhans were isolated from the pancreata of 10-12 wk-old C57BL/6 mice by collagenase digestion and discontinuous Ficoll gradient separation, a modification of the original method of Lacy and Kostianovsky (Lacy & Kostianovsky, 1967 Diabetes 16-35-39). The islets were cultured overnight in RPM 1640 medium (11 mM glucose, 10% FCS) before experimental treatment. The acute effects of compounds of this invention on GDIS were determined by 60-min static incubation with islets in Krebs-Ringers' bicarbonate (KRB) medium. The KRB medium contained, in mM, 143.5 $Na^+$, 5.8 $K^+$, 2.5 $Ca^{2+}$, 1.2 $Mg^{2+}$, 124.1 $Cl^-$, 1.2 $PO_4^{3-}$, 1.2 $SO_4^{2+}$, 25 $CO_3^{2-}$, and 10 HEPES, pH 7.4, in addition to 2 mg/ml bovine serum albumin, and either 2 (G2) or 16 (G16) mM glucose (pH 7.4). The static incubation was performed with round-bottomed 96-well plates (one islet/well with 200 μl KRB medium). The compounds were added to KRB medium just before the initiation of the 60-min incubation. Insulin concentration in aliquots of the incubation buffer was measured by the ultra-sensitive rat insulin EIA kit from ALPCO Diagnostics (Windham, N.H.).

The compounds of the present application are surprisingly potent as GPR119 agonists.

Example of a Pharmaceutical Formulation

As a specific embodiment of an oral composition of a compound of the present invention, 50 mg of any of the examples is formulated with sufficient finely divided lactose to provide a total amount of 580 to 590 mg to fill a size 0 hard gelatin capsule.

While the invention has been described and illustrated in reference to specific embodiments thereat various changes, modifications, and substitutions can be made therein without departing from the invention. For example, alternative effective dosages may be applicable, based upon the responsiveness of the patient being treated. Likewise, the pharmacologic response may vary depending upon the particular active compound selected, formulation and mode of administration. All such variations are included within the present invention.

What is claimed is:

1. A compound represented by the formula:

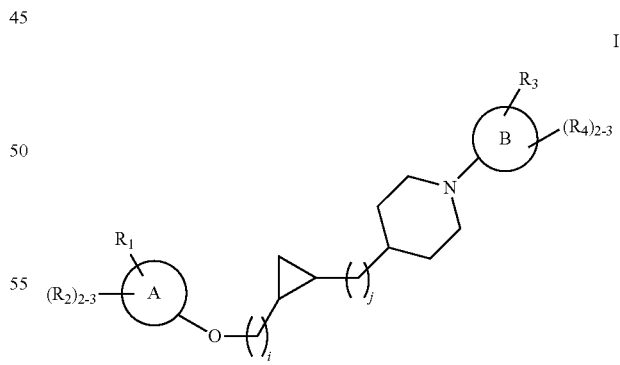

I or a pharmaceutically acceptable salt thereof, wherein:
Ring A represents a 6-membered aryl or heteroaryl group containing 1 nitrogen atom, and optionally 1-2 additional nitrogen atoms;
Ring B represents a 6 membered heteroaryl ring containing 1-2 nitrogen atoms;
i and j independently represent integers selected from 0, 1 and 2, such that i plus j is 1 or 2;

R¹ represents a member selected from the group consisting of H, halo, $C_{1-6}$alkyl, halo$C_{1-6}$alkyl, C(O)$C_{1-6}$alkyl, C(O)halo$C_{1-6}$alkyl, C(O)NH—$C_{1-6}$alkyl, S(O)$C_{1-6}$alkyl, SO$_2C_{1-6}$alkyl, SO$_2$NH$_2$, SO$_2$NH$C_{1-6}$alkyl, SO$_2$N($C_{1-6}$alkyl)$_2$, CN, and HAR optionally substituted with 1-3 $C_{1-6}$alkyl, halo or halo $C_{1-6}$alkyl groups;

and each R², R³ and R⁴ is independently selected from H, halo, $C_{1-6}$ alkyl and halo$C_{1-6}$alkyl.

2. A compound in accordance with claim 1, or a pharmaceutically acceptable salt thereof, wherein ring A is selected from the group consisting of Aryl which is phenyl, and Heteroaryl selected from the group consisting of pyridine, pyrimidine and pyrazine.

3. A compound in accordance with claim 2, or a pharmaceutically acceptable salt thereof, wherein ring A is selected from the group consisting of phenyl and pyrimidine.

4. A compound of formula I, or a pharmaceutically acceptable salt thereof, wherein ring A is a pyrimidine ring.

5. A compound in accordance with claim 1, or a pharmaceutically acceptable salt thereof, wherein ring B is selected from the group consisting of pyridine, pyrimidine and pyrazine.

6. A compound in accordance with claim 5, or a pharmaceutically acceptable salt thereof, wherein ring B is pyrimidine.

7. A compound in accordance with claim 1, or a pharmaceutically acceptable salt thereof, wherein i and j represent 0, 1 or 2, such that the sum of i and j is 2.

8. A compound in accordance with claim 1, or a pharmaceutically acceptable salt thereof, wherein R¹ is selected from the group consisting of: H, halo which is F or Br, $C_{1-3}$alkyl, halo$C_{1-3}$alkyl, C(O)NH$C_{2-4}$alkyl, S(O)$C_{1-3}$alkyl, SO$_2C_{1-3}$alkyl, SO$_2$NH$C_{1-3}$alkyl, CN and HAR which is a 5 membered heteroaromatic ring containing one nitrogen atom, optionally 1-3 additional nitrogen atoms, and optionally one oxygen atom, said heteroaryl being optionally substituted with one $C_{1-3}$alkyl group.

9. A compound in accordance with claim 8, or a pharmaceutically acceptable salt thereof, wherein R¹ is selected from the group consisting of: H, halo which is F or Br, $C_{1-3}$alkyl, CF$_3$, C(O)NH-cyclopropyl, S(O)CH$_3$, SO$_2$CH$_3$, SO$_2$NHcyclopropyl, CN and HAR which is selected from the group consisting of: oxadiazole, triazole and tetrazole, said group being optionally substituted with methyl or cyclopropyl.

10. A compound in accordance with claim 1, or a pharmaceutically acceptable salt thereof, wherein Ring A represents a phenyl ring and R¹ represents a five membered heteroaryl ring selected from the group consisting of oxadiazole, triazole and tetrazole, said ring being optionally substituted with methyl or cyclopropyl.

11. A compound in accordance with claim 1, or a pharmaceutically acceptable salt thereof, wherein Ring A represents a pyridine or pyrimidine ring and R¹ represents CN, CF$_3$, or a five membered heteroaryl ring selected from the group consisting of oxadiazole, triazole and tetrazole, said ring being optionally substituted with methyl or cyclopropyl.

12. A compound in accordance with claim 1, or a pharmaceutically acceptable salt thereof, wherein R² represents H, halo selected from F and Cl, CH$_3$ or CF$_3$.

13. A compound in accordance with claim 1, or a pharmaceutically acceptable salt thereof, wherein R³ and R⁴ are selected from the group consisting of: H, halo selected from F and Cl, CH$_3$ and CF$_3$.

14. A compound in accordance with claim 1, or a pharmaceutically acceptable salt thereof, wherein the cyclopropyl ring is the cis cyclopropyl isomer.

15. A compound in accordance with claim 1, or a pharmaceutically acceptable salt thereof wherein:
ring A is selected from the group consisting of Aryl which is phenyl, and Heteroaryl selected from the group consisting of pyridine, pyrimidine and pyrazine;
ring B is selected from the group consisting of pyridine, pyrimidine and pyrazine;
i and j represent 0, 1 or 2, such that the sum of i and j is 2;
R¹ is selected from the group consisting of: H, halo which is F or Br, $C_{1-3}$alkyl, halo$C_{1-3}$alkyl, C(O)NH$C_{2-4}$alkyl, S(O)$C_{1-3}$alkyl, SO$_2C_{1-3}$alkyl, SO$_2$NH$C_{1-3}$alkyl, CN and HAR which is a 5 membered heteroaromatic ring containing one nitrogen atom, optionally 1-3 additional nitrogen atoms, and optionally one oxygen atom, said heteroaryl being optionally substituted with one $C_{1-3}$alkyl group;
R² represents H, halo selected from F and Cl, CH$_3$ and CF$_3$;
and R³ and R⁴ represent H, halo selected from F and Cl, CH$_3$ and CF$_3$.

16. A compound in accordance with claim 1 selected from the group consisting of:

| Compound Name |
| --- |
| rac cis-5-chloro-2-[4-(2-{2-[4-(methylsulfonyl)phenoxy]ethyl} cyclopropyl)piperidin-1-yl]pyrimidine, 5-chloro-2-[4-((1S,2R)-2-{2-[4-(methylsulfonyl)phenoxy]ethyl}cyclopropyl)piperidin-1-yl]pyrimidine and 5-chloro-2-[4-((1R,2S)-2-{2-[4-(methylsulfonyl)phenoxy]ethyl}cyclopropyl) piperidin-1-yl]pyrimidine |
| rac-cis 5-chloro-2-{4-[2-(2-{[5-(methylsulfonyl)pyridin-2-yl]oxy}ethyl)cyclopropyl]piperidin-1-yl}pyrimidine, cis 5-chloro-2-{4-[(1S,2R)-2-(2-{[5-(methylsulfonyl)pyridin-2-yl]oxy}ethyl)cyclopropyl]piperidin-1-yl}pyrimidine, cis 5-chloro-2-{4-[(1R,2S)-2-(2-{[5-(methylsulfonyl)pyridin-2-yl]oxy}ethyl)cyclopropyl]piperidin-1-yl}pyrimidine |
| rac cis-5-chloro-2-[4-(2-{2-[3-(methylsulfonyl)phenoxy]ethyl}cyclopropyl)piperidin-1-yl]pyrimidine |
| rac cis-5-chloro-2-[4-(2-{2-[3-(5-methyl-1,3,4-oxadiazol-2-yl)phenoxy]ethyl}cyclopropyl)piperidin-1-yl]pyrimidine |
| rac cis-5-chloro-2-[4-(2-{2-[3-(1H-1,2,4-triazol-1-yl)phenoxy]ethyl}cyclopropyl)piperidin-1-yl]pyrimidine |
| rac cis-5-chloro-2-[4-(2-{2-[3-(1,3,4-oxadiazol-2-yl)phenoxy]ethyl}cyclopropyl)piperidin-1-yl]pyrimidine |
| rac cis-4-(2-{2-[1-(5-chloropyrimidin-2-yl)piperidin-4-yl]cyclopropyl}ethoxy)-N-cyclopropyl-2-fluorobenzamide |
| rac cis-4-(2-{2-[1-(5-chloropyrimidin-2-yl)piperidin-4-yl]cyclopropyl}ethoxy)-2-fluorobenzonitrile |
| rac cis-5-chloro-2-[4-(2-{2-[4-(cyclopropylsulfonyl)phenoxy]ethyl}cyclopropyl)piperidin- |

| Compound Name |
| --- |
| 1-yl]pyrimidine
rac cis-5-chloro-2-[4-(2-{2-[3-fluoro-4-(5-methyl-1,3,4-oxadiazol-2-yl)phenoxy]ethyl}cyclopropyl)piperidin-1-yl]pyrimidine
rac cis-5-chloro-2-[4-(2-{2-[4-(1,3,4-oxadiazol-2-yl)phenoxy]ethyl}cyclopropyl)piperidin-1-yl]pyrimidine
rac cis-5-chloro-2-[4-(2-{2-[4-(5-methyl-1,3,4-oxadiazol-2-yl)phenoxy]ethyl}cyclopropyl)piperidin-1-yl]pyrimidine
rac cis-5-chloro-2-[4-(2-{2-[4-(1,2,4-oxadiazol-3-yl)phenoxy]ethyl}cyclopropyl)piperidin-1-yl]pyrimidine
rac cis-5-chloro-2-[4-(2-{2-[4-(1,2,4-oxadiazol-5-yl)phenoxy]ethyl}cyclopropyl)piperidin-1-yl]pyrimidine
rac cis-5-chloro-2-[4-(2-{2-[4-(1,3-oxazol-4-yl)phenoxy]ethyl}cyclopropyl)piperidin-1-yl]pyrimidine
rac cis-5-chloro-2-(4-{2-[2-(4-isoxazol-4-ylphenoxy)ethyl]cyclopropyl}piperidin-1-yl)pyrimidine
rac cis-5-chloro-2-(4-{2-[2-(4-isoxazol-5-ylphenoxy)ethyl]cyclopropyl}piperidin-1-yl)pyrimidine
rac cis-5-chloro-2-[4-(2-{2-[4-(1H-pyrazol-3-yl)phenoxy]ethyl}cyclopropyl)piperidin-1-yl]pyrimidine
rac cis-5-chloro-2-[4-(2-{2-[4-(1H-pyrazol-4-yl)phenoxy]ethyl}cyclopropyl)piperidin-1-yl]pyrimidine
rac cis-5-chloro-2-[4-(2-{2-[4-(1H-pyrazol-1-yl)phenoxy]ethyl}cyclopropyl)piperidin-1-yl]pyrimidine
rac cis-5-chloro-2-[4-(2-{2-[4-(1H-1,2,4-triazol-1-yl)phenoxy]ethyl}cyclopropyl)piperidin-1-yl]pyrimidine
rac cis-5-chloro-2-[4-(2-{2-[4-(4H-1,2,4-triazol-4-yl)phenoxy]ethyl}cyclopropyl)piperidin-1-yl]pyrimidine
rac cis-5-chloro-2-[4-(2-{2-[4-(1H-1,2,3-triazol-1-yl)phenoxy]ethyl}cyclopropyl)piperidin-1-yl]pyrimidine
rac-cis-5-fluoro-2-[4-(2-{2-[4-(1H-1,2,3-triazol-1-yl)phenoxy]ethyl}cyclopropyl)piperidin-1-yl]pyrimidine
rac cis-5-methyl-2-[4-(2-{2-[4-(1H-1,2,3-triazol-1-yl)phenoxy]ethyl}cyclopropyl)piperidin-1-yl]pyrimidine
rac cis-5-chloro-2-[4-(2-{2-[4-(2H-1,2,3-triazol-2-yl)phenoxy]ethyl}cyclopropyl)piperidin-1-yl]pyrimidine
rac cis-5-chloro-2-[4-(2-{2-[4-(1H-1,2,3-triazol-5-yl)phenoxy]ethyl}cyclopropyl)piperidin-1-yl]pyrimidine
rac cis-5-chloro-2-[4-(2-{2-[4-(1H-tetrazol-1-yl)phenoxy]ethyl}cyclopropyl)piperidin-1-yl]pyrimidine
rac cis-5-chloro-2-[4-(2-{2-[3-fluoro-4-(1H-tetrazol-1-yl)phenoxy]ethyl}cyclopropyl)piperidin-1-yl]pyrimidine
rac cis-5-fluoro-2-[4-(2-{2-[3-fluoro-4-(1H-tetrazol-1-yl)phenoxy]ethyl}cyclopropyl)piperidin-1-yl]pyrimidine
rac cis-2-[4-(2-{2-[3-fluoro-4-(1H-tetrazol-1-yl)phenoxy]ethyl}cyclopropyl)piperidin-1-yl]-5-methylpyrimidine
rac cis-5-chloro-2-[4-(2-{2-[4-(2H-tetrazol-2-yl)phenoxy]ethyl}cyclopropyl)piperidin-1-yl]pyrimidine
rac cis-5-chloro-2-[4-(2-{2-[4-(5-methyl-2H-tetrazol-2-yl)phenoxy]ethyl}cyclopropyl)piperidine-1-yl]pyrimidine
rac cis-5-chloro-2-[4-(2-{2-[4-(5-methyl-1H-tetrazol-1-yl)phenoxy]ethyl}cyclopropyl)piperidin-1-yl]pyrimidine
rac cis-5-chloro-2-[4-(2-{2-[3-fluoro-4-(5-methyl-1,3,4-oxadiazol-2-yl)phenoxy]ethyl}cyclopropyl)piperidin-1-yl]pyrimidine
rac-cis-5-chloro-2-[4-(2-{2-[4-(methylsulfinyl)phenoxy]ethyl}cyclopropyl)piperidin-1-yl]pyrimidine
Chiral-cis-6-(2-{2-[1-(5-chloropyrimidin-2-yl)piperidin-4-yl]cyclopropyl}ethoxy)-2-methylpyrimidine-4-carbonitrile, cis 6-(2-{(1S,2R)-2-{1-(5-chloropyrimidin-2-yl)piperidin-4-yl]cyclopropyl}ethoxy)-2-methylpyrimidine-4-carbonitrile, cis 6-(2-{(1R,2S)-2-{1-(5-chloropyrimidin-2-yl)piperidin-4-yl]cyclopropyl}ethoxy)-2-methylpyrimidine-4-carbonitrile
Rac-cis-1-[4-(2-{2-[1-(5-chloropyrimidin-2-yl)piperidin-4-yl]cyclopropyl}ethoxy)phenyl]ethanone
Rac-cis-2-methyl-6-(2-{2-[1-(5-methylpyrazin-2-yl)piperidin-4-yl]cyclopropyl}ethoxy)pyrimidine-4-carbonitrile
Rac-cis-6-(2-{2-[1-(5-chloropyrimidin-2-yl)piperidin-4-yl]cyclopropyl}ethoxy)pyrimidine-4-carbonitrile
Rac-cis-4-(2-{2-[1-(5-chloropyrimidin-2-yl)piperidin-4-yl]cyclopropyl}ethoxy)pyrimidine-2-carbonitrile
Chiral-cis-2-methyl-6-(2-{2-[1-(5-methylpyrimidin-2-yl)piperidin-4-yl]cyclopropyl}ethoxy)pyrimidine-4-carbonitrile, cis-2-methyl-6-(2-{(1S,2R)-2-[1-(5-methylpyrimidin-2-yl)piperidin-4-yl]cyclopropyl}ethoxy)pyrimidine-4-carbonitrile, cis-2-methyl-6-(2-{(1R,2S)-2-[1-(5-methylpyrimidin-2-yl)piperidin-4-yl]cyclopropyl}ethoxy)pyrimidine-4-carbonitrile
Rac-cis-2-methyl-6-(2-{2-[1-(5-methylpyrimidin-2-yl)piperidin-4-yl]cyclopropyl}ethoxy)pyrimidine-4-carbonitrile
Rac-cis-2,4-dimethyl-6-(2-{2-[1-(5-methylpyrimidin-2-yl)piperidin-4-yl]cyclopropyl}ethoxy)pyrimidine
Rac-cis-6-(2-{2-[1-(5-chloro-4-methylpyrimidin-2-yl)piperidin-4-yl]cyclopropyl}ethoxy)- |

| Compound Name |
| --- |
| 2-methylpyrimidine-4-carbonitrile |
| Rac-cis-6-(2-{2-[1-(5-chloropyridin-2-yl)piperidin-4-yl]cyclopropyl}ethoxy)-2-methylpyrimidine-4-carbonitrile |
| Rac-cis-6-(2-{2-[1-(4,5-dimethylpyrimidin-2-yl)piperidin-4-yl]cyclopropyl}ethoxy)-2-methylpyrimidine-4-carbonitrile |
| Rac-cis-6-(2-{2-[1-(5-chloro-4-methylpyridin-2-yl)piperidin-4-yl]cyclopropyl}ethoxy)-2-methylpyrimidine-4-carbonitrile |
| Rac-cis-6-(2-{2-[1-(5-fluoro-4-methylpyrimidin-2-yl)piperidin-4-yl]cyclopropyl}ethoxy)-2-methylpyrimidine-4-carbonitrile |
| Rac-cis-2-methyl-6-[2-(2-{1-[5-(trifluoromethyl)pyridin-2-yl]piperidin-4-yl}cyclopropyl)ethoxy]pyrimidine-4-carbonitrile |
| Rac-cis-5-chloro-2-(4-{2-[2-(pyridin-3-yloxy)ethyl]cyclopropyl}piperidin-1-yl)pyrimidine |
| Rac-cis-5-chloro-2-(4-{2-[2-(pyrimidin-4-yloxy)ethyl]cyclopropyl}piperidin-1-yl)pyrimidine |
| Rac-cis-5-(2-{2-[1-(5-chloropyrimidin-2-yl)piperidin-4-yl]cyclopropyl}ethoxy)nicotinonitrile |
| Rac-cis-6-(2-{2-[1-(5-chloropyrimidin-2-yl) piperidin-4-yl] cyclopropyl} ethoxy)-2-methylpyrimidine-4-carbonitrile |
| Rac-cis-4-(2-{2-[1-(5-chloropyrimidin-2-yl)piperidin-4-yl]cyclopropyl} ethoxy)-6-methylpyrimidine-2-carbonitrile |
| Rac-cis-6-(2-{2-[1-(5-fluoropyrimidin-2-yl)piperidin-4-yl]cyclopropyl}ethoxy)-2-methylpyrimidine-4-carbonitrile |
| Rac-cis-5-(2-{2-[1-(5-chloropyrimidin-2-yl)piperidin-4-yl]cyclopropyl}ethoxy)pyridine-2-carbonitrile |
| Rac-cis-5-chloro-2-(4-{2-[2-(pyridin-4-yloxy)ethyl]cyclopropyl}piperidin-1-yl)pyrimidine |
| Chiral cis-5-chloro-2-{4-[2-(2-{[5-(1H-1,2,3-triazol-1-yl)pyridin-2-yl]oxy}ethyl)cyclopropyl]piperidin-1-yl}pyrimidine, cis-5-chloro-2-{4-(1S,2R)-[2-(2-{[5-(1H-1,2,3-triazol-1-yl)pyridin-2-yl]oxy}ethyl)cyclopropyl]piperidin-1-yl}pyrimidine, cis-5-chloro-2-{4-(1R,2S)-[2-(2-{[5-(1H-1,2,3-triazol-1-yl)pyridin-2-yl]oxy}ethyl)cyclopropyl]piperidin-1-yl}pyrimidine |
| 5-chloro-2-[4-((1R,2S)-2-{2-[3-fluoro-4-(5-methyl-1,3,4-oxadiazol-2-yl)phenoxy]ethyl}cyclopropyl)piperidin-1-yl]pyrimidine and 5-chloro-2-[4-((1S,2R)-2-{2-[3-fluoro-4-(5-methyl-1,3,4-oxadiazol-2-yl)phenoxy]ethyl}cyclopropyl)piperidin-1-yl]pyrimidine |
| 5-chloro-2-[4-((1S,2R)-2-{2-[4-(1H-1,2,3-triazol-1-yl)phenoxy]ethyl}cyclopropyl)piperidin-1-yl]pyrimidine and 5-chloro-2-[4-((1R,2S)-2-{2-[4-(1H-1,2,3-triazol-1-yl)phenoxy]ethyl}cyclopropyl)piperidin-1-yl]pyrimidine |
| 5-fluoro-2-[4-((1R,2S)-2-{2-[4-(1H-1,2,3-triazol-1-yl)phenoxy]ethyl}cyclopropyl)piperidin-1-yl]pyrimidine and 5-fluoro-2-[4-((1S,2R)-2-{2-[4-(1H-1,2,3-triazol-1-yl)phenoxy]ethyl}cyclopropyl)piperidin-1-yl]pyrimidine |
| 5-chloro-2-[4-((1R,2S)-2-{2-[4-(1H-tetrazol-1-yl)phenoxy]ethyl}cyclopropyl)piperidin-1-yl]pyrimidine and 5-chloro-2-[4-((1S,2R)-2-{2-[4-(1H-tetrazol-1-yl)phenoxy]ethyl}cyclopropyl)piperidin-1-yl]pyrimidine |
| 5-chloro-2-[4-((1R,2S)-2-{2-[3-fluoro-4-(1H-tetrazol-1-yl)phenoxy]ethyl}cyclopropyl)piperidin-1-yl]pyrimidine and 5-chloro-2-[4-((1S,2R)-2-{2-[3-fluoro-4-(1H-tetrazol-1-yl)phenoxy]ethyl}cyclopropyl)piperidin-1-yl]pyrimidine |
| 5-fluoro-2-[4-((1R,2S)-2-{2-[3-fluoro-4-(5-methyl-1,3,4-oxadiazol-2-yl)phenoxy]ethyl}cyclopropyl)piperidin-1-yl]pyrimidine and 5-fluoro-2-[4-((1S,2R)-2-{2-[3-fluoro-4-(5-methyl-1,3,4-oxadiazol-2-yl)phenoxy]ethyl}cyclopropyl)piperidin-1-yl]pyrimidine |
| rac-cis-2-[4-(2-{2-[3-fluoro-4-(5-methyl-1,3,4-oxadiazol-2-yl)phenoxy]ethyl}cyclopropyl)piperidin-1-yl]-5-methylpyrimidine |
| Rac-cis-2-[4-(2-{2-[3-fluoro-4-(5-methyl-1,3,4-oxadiazol-2-yl)phenoxy]ethyl}cyclopropyl)piperidin-1-yl]pyrimidine |
| Rac-cis-5-fluoro-2-[4-(2-{2-[3-fluoro-4-(5-methyl-1,3,4-oxadiazol-2-yl)phenoxy]ethyl}cyclopropyl)piperidin-1-yl]pyrimidine |
| Rac-cis-5-chloro-2-[4-(2-{2-[3-fluoro-4-(5-methyl-1,3,4-oxadiazol-2-yl)phenoxy]ethyl}cyclopropyl)piperidin-1-yl]-4-methylpyrimidine |
| Rac-cis-3,5-dichloro-2-[4-(2-{2-[3-fluoro-4-(5-methyl-1,3,4-oxadiazol-2-yl)phenoxy]ethyl}cyclopropyl)piperidin-1-yl]pyridine |
| Rac-cis-2-[4-(2-{2-[3-fluoro-4-(5-methyl-1,3,4-oxadiazol-2-yl)phenoxy]ethyl}cyclopropyl)piperidin-1-yl]-5-(trifluoromethyl)pyridinium trifluoroacetate |
| rac-trans-5-chloro-2-[4-(2-{2-[4-(methylsulfonyl)phenoxy]ethyl}cyclopropyl)piperidin-1-yl]pyrimidine |
| rac-trans-5-chloro-2-(4-{2-[2-(pyridin-4-yloxy)ethyl]cyclopropyl}piperidin-1-yl)pyrimidine |
| 4-(2-{(1R,2R)-2-[1-(5-chloropyrimidin-2-yl)piperidin-4-yl]cyclopropyl}ethoxy)-N-cyclopropyl-2-fluorobenzamide |
| 4-(2-{(1R,2R)-2-[1-(5-chloropyrimidin-2-yl)piperidin-4-yl]cyclopropyl}ethoxy)-2-fluorobenzonitrile |
| 5-chloro-2-[4-((1R,2R)-2-{2-[4-(1H-1,2,4-triazol-1-yl)phenoxy]ethyl}cyclopropyl)piperidin-1-yl]pyrimidine |
| 5-chloro-2-[4-((1R,2R)-2-{2-[3-fluoro-4-(5-methyl-1,3,4-oxadiazol-2-yl)phenoxy]ethyl}cyclopropyl)piperidin-1-yl]pyrimidine |
| 5-chloro-2-[4-((1R,2R)-2-{2-[4-(5-cyclopropyl-1,3,4-oxadiazol-2-yl)-3-fluorophenoxy]ethyl}cyclopropyl)piperidin-1-yl]pyrimidine |
| rac-trans-5-chloro-2-(4-{2-[2-(pyridin-4-yloxy)ethyl]cyclopropyl}piperidin-1-yl)pyrimidine |

| Compound Name |
|---|
| rac-trans-4-(2-{2-[1-(5-chloropyrimidin-2-yl) piperidin-4-yl]cyclopropyl} ethoxy)-6-methylpyrimidine-2-carbonitrile |
| rac trans 6-(2-{2-[1-(5-chloropyrimidin-2-yl)piperidin-4-yl] cyclopropyl} ethoxy)-2-methylpyrimidine-4-carbonitrile |
| rac-trans-5-chloro-2-{4-[(2-{[4-(methylsulfonyl)phenoxy]methyl}cyclopropyl)methyl]piperidin-1-yl}pyrimidine |
| 5-chloro-2-[4-((1R,2R)-2-{2-[4-(methylsulfonyl)phenoxy]ethyl} cyclopropyl)piperidin-1-yl]pyrimidine |
| 5-chloro-2-{4-[((1S,2S)-2-{[4-(methylsulfonyl)phenoxy]methyl}cyclopropyl)methyl]piperidin-1-yl}pyrimidine |
| Rac-trans-4-[(2-{[1-(5-chloropyrimidin-2-yl)piperidin-4-yl]methyl}cyclopropyl)methoxy]-2-fluorobenzonitrile |
| 4-[((1R,2R)-2-{[1-(5-chloropyrimidin-2-yl)piperidin-4-yl]methyl}cyclopropyl)methoxy]-2-fluorobenzonitrile |
| Rac-trans 4-[(2-{[1-(5-chloropyrimidin-2-yl)piperidin-4-yl]methyl}cyclopropyl)methoxy]-N-cyclopropyl-2-fluorobenzamide |
| 4-[((1R,2R)-2-{[1-(5-chloropyrimidin-2-yl)piperidin-4-yl]methyl}cyclopropyl)methoxy]-N-cyclopropyl-2-fluorobenzamide |
| 4-[((1S,2S)-2-{[1-(5-chloropyrimidin-2-yl)piperidin-4-yl]methyl}cyclopropyl)methoxy]-N-cyclopropyl-2-fluorobenzamide |
| 5-chloro-2-{4-[((1R,2R)-2-{[3-fluoro-4-(5-methyl-1,3,4-oxadiazol-2-yl)phenoxy]methyl}cyclopropyl)methyl]piperidin-1-yl}pyrimidine |
| 5-chloro-2-{4-[((1S,2S)-2-{[3-fluoro-4-(5-methyl-1,3,4-oxadiazol-2-yl)phenoxy]methyl}cyclopropyl)methyl]piperidin-1-yl}pyrimidine |
| rac-trans 5-chloro-2-{4-[(2-{[4-(5-cyclopropyl-1,3,4-oxadiazol-2-yl)-3-fluorophenoxy]methyl}cyclopropyl)methyl]piperidin-1-yl}pyrimidine |
| 4-[((1S,2S)-2-{[1-(5-chloropyrimidin-2-yl)piperidin-4-yl]methyl}cyclopropyl)methoxy]benzenesulfonamide |
| rac-trans-6-[(2-{[1-(5-chloropyrimidin-2-yl)piperidin-4-yl] methyl} cyclopropyl)methoxy]-2-methylpyrimidine-4-carbonitrile |
| rac-trans-4-[(2-{[1-(5-chloropyrimidin-2-yl)piperidin-4-yl]methyl}cyclopropyl)methoxy]-6-methylpyrimidine-2-carbonitrile |
| rac-trans-4-[((1S,2S)-2-{[1-(5-chloropyrimidin-2-yl)piperidin-4-yl]methyl}cyclopropyl)methoxy]-3-fluorobenzonitrile |
| rac-cis-5-chloro-2-{4-[(2-{[4-(methylsulfonyl)phenoxy]methyl}cyclopropyl)methyl]piperidin-1-yl}pyrimidine |
| rac-cis 4-[(2-{[1-(5-chloropyrimidin-2-yl)piperidin-4-yl]methyl}cyclopropyl)methoxy]-N-cyclopropyl-2-fluorobenzamide |
| rac-cis-4-[(2-{[1-(5-chloropyrimidin-2-yl)piperidin-4-yl]methyl}cyclopropyl)methoxy]-6-methylpyrimidine-2-carbonitrile |
| rac-cis 4-[(2-{[1-(5-chloropyrimidin-2-yl)piperidin-4-yl]methyl}cyclopropyl)methoxy]-2-fluorobenzonitrile | or a pharmaceutically acceptable salt thereof.

17. A compound in accordance with claim 14, selected from the group consisting of:

TABLE 1-a rac cis-5-chloro-2-[4-(2-{2-[4-(methylsulfonyl)phenoxy]ethyl} cyclopropyl)piperidin-1-yl]pyrimidine, 5-chloro-2-[4-((1S,2R)-2-{2-[4-(methylsulfonyl)phenoxy]ethyl}cyclopropyl)piperidin-1-yl]pyrimidine and 5-chloro-2-[4-((1R,2S)-2-{2-[4-(methylsulfonyl)phenoxy]ethyl}cyclopropyl) piperidin-1-yl]pyrimidine
rac-cis 5-chloro-2-{4-[2-(2-{[5-(methylsulfonyl)pyridin-2-yl]oxy}ethyl)cyclopropyl]piperidin-1-yl}pyrimidine, 5-chloro-2-{4-[(1R,2S)-2-(2-{[5-(methylsulfonyl)pyridin-2-yl]oxy}ethyl)cyclopropyl]piperidin-1-yl}pyrimidine, 5-chloro-2-{4-[(1S,2R)-2-(2-{[5-(methylsulfonyl)pyridin-2-yl]oxy}ethyl)cyclopropyl]piperidin-1-yl}pyrimidine
rac cis-5-chloro-2-[4-(2-{2-[3-(methylsulfonyl)phenoxy]ethyl}cyclopropyl)piperidin-1-yl]pyrimidine
rac cis-5-chloro-2-[4-(2-{2-[3-(5-methyl-1,3,4-oxadiazol-2-yl)phenoxy]ethyl}cyclopropyl)piperidin-1-yl]pyrimidine
rac cis-5-chloro-2-[4-(2-{2-[3-(1H-1,2,4-triazol-1-yl)phenoxy]ethyl}cyclopropyl)piperidin-1-yl]pyrimidine
rac cis-5-chloro-2-[4-(2-{2-[3-(1,3,4-oxadiazol-2-yl)phenoxy]ethyl}cyclopropyl)piperidin-1-yl]pyrimidine
rac cis-4-(2-{2-[1-(5-chloropyrimidin-2-yl)piperidin-4-yl]cyclopropyl}ethoxy)-N-cyclopropyl-2-fluorobenzamide
rac cis-4-(2-{2-[1-(5-chloropyrimidin-2-yl)piperidin-4-yl]cyclopropyl}ethoxy)-2-fluorobenzonitrile
rac cis-5-chloro-2-[4-(2-{2-[4-(cyclopropylsulfonyl)phenoxy]ethyl}cyclopropyl)piperidin-1-yl]pyrimidine
rac cis-5-chloro-2-[4-(2-{2-[3-fluoro-4-(5-methyl-1,3,4-oxadiazol-2-yl)phenoxy]ethyl}cyclopropyl)piperidin-1-yl]pyrimidine
rac cis-5-chloro-2-[4-(2-{2-[4-(1,3,4-oxadiazol-2-

TABLE 1-a-continued yl)phenoxy]ethyl}cyclopropyl)piperidin-1-yl]pyrimidine
rac cis-5-chloro-2-[4-(2-{2-[4-(5-methyl-1,3,4-oxadiazol-2-
yl)phenoxy]ethyl}cyclopropyl)piperidin-1-yl]pyrimidine
rac cis-5-chloro-2-[4-(2-{2-[4-(1,2,4-oxadiazol-3-
yl)phenoxy]ethyl}cyclopropyl)piperidin-1-yl]pyrimidine
rac cis-5-chloro-2-[4-(2-{2-[4-(1,2,4-oxadiazol-5-
yl)phenoxy]ethyl}cyclopropyl)piperidin-1-yl]pyrimidine
rac cis-5-chloro-2-[4-(2-{2-[4-(1,3-oxazol-4-yl)phenoxy]ethyl}cyclopropyl)piperidin-1-
yl]pyrimidine
rac cis-5-chloro-2-(4-{2-[2-(4-isoxazol-4-ylphenoxy)ethyl]cyclopropyl}piperidin-1-
yl)pyrimidine
rac cis-5-chloro-2-(4-{2-[2-(4-isoxazol-5-ylphenoxy)ethyl]cyclopropyl}piperidin-1-
yl)pyrimidine
rac cis-5-chloro-2-[4-(2-{2-[4-(1H-pyrazol-3-yl)phenoxy]ethyl}cyclopropyl)piperidin-1-
yl]pyrimidine
rac cis-5-chloro-2-[4-(2-{2-[4-(1H-pyrazol-4-yl)phenoxy]ethyl}cyclopropyl)piperidin-1-
yl]pyrimidine
rac cis-5-chloro-2-[4-(2-{2-[4-(1H-pyrazol-1-yl)phenoxy]ethyl}cyclopropyl)piperidin-1-
yl]pyrimidine
rac cis-5-chloro-2-[4-(2-{2-[4-(1H-1,2,4-triazol-1-
yl)phenoxy]ethyl}cyclopropyl)piperidin-1-yl]pyrimidine
rac cis-5-chloro-2-[4-(2-{2-[4-(4H-1,2,4-triazol-4-
yl)phenoxy]ethyl}cyclopropyl)piperidin-1-yl]pyrimidine
rac cis-5-chloro-2-[4-(2-{2-[4-(1H-1,2,3-triazol-1-
yl)phenoxy]ethyl}cyclopropyl)piperidin-1-yl]pyrimidine
rac-cis-5-fluoro-2-[4-(2-{2-[4-(1H-1,2,3-triazol-1-
yl)phenoxy]ethyl}cyclopropyl)piperidin-1-yl]pyrimidine
rac cis-5-methyl-2-[4-(2-{2-[4-(1H-1,2,3-triazol-1-
yl)phenoxy]ethyl}cyclopropyl)piperidin-1-yl]pyrimidine
rac cis-5-chloro-2-[4-(2-{2-[4-(2H-1,2,3-triazol-2-
yl)phenoxy]ethyl}cyclopropyl)piperidin-1-yl]pyrimidine
rac cis-5-chloro-2-[4-(2-{2-[4-(1H-1,2,3-triazol-5-
yl)phenoxy]ethyl}cyclopropyl)piperidin-1-yl]pyrimidine
rac cis-5-chloro-2-[4-(2-{2-[4-(1H-tetrazol-1-yl)phenoxy]ethyl}cyclopropyl)piperidin-1-
yl]pyrimidine
rac cis-5-chloro-2-[4-(2-{2-[3-fluoro-4-(1H-tetrazol-1-
yl)phenoxy]ethyl}cyclopropyl)piperidin-1-yl]pyrimidine
rac cis-5-fluoro-2-[4-(2-{2-[3-fluoro-4-(1H-tetrazol-1-
yl)phenoxy]ethyl}cyclopropyl)piperidin-1-yl]pyrimidine
rac cis-2-[4-(2-{2-[3-fluoro-4-(1H-tetrazol-1-yl)phenoxy]ethyl}cyclopropyl)piperidin-1-
yl]-5-methylpyrimidine
rac cis-5-chloro-2-[4-(2-{2-[4-(2H-tetrazol-2-yl)phenoxy]ethyl}cyclopropyl)piperidin-1-
yl]pyrimidine
rac cis-5-chloro-2-[4-(2-{2-[4-(5-methyl-2H-tetrazol-2-
yl)phenoxy]ethyl}cyclopropyl)piperidine-1-yl]pyrimidine
rac cis-5-chloro-2-[4-(2-{2-[4-(5-methyl-1H-tetrazol-1-
yl)phenoxy]ethyl}cyclopropyl)piperidin-1-yl]pyrimidine
rac cis-5-chloro-2-[4-(2-{2-[3-fluoro-4-(5-methyl-1,3,4-oxadiazol-2-
yl)phenoxy]ethyl}cyclopropyl)piperidin-1-yl]pyrimidine
5-chloro-2-[4-(1S,2R)-(2-{2-[4-(methylsulfinyl)phenoxy]ethyl}cyclopropyl)piperidin-1-
yl]pyrimidine, 5-chloro-2-[4-(1R,2S)-(2-{2-[4-
(methylsulfinyl)phenoxy]ethyl}cyclopropyl)piperidin-1-yl]pyrimidine
6-(1S,2R)-(2-{2-[1-(5-chloropyrimidin-2-yl)piperidin-4-yl]cyclopropyl}ethoxy)-2-
methylpyrimidine-4-carbonitrile, 6-(1R,2S)-(2-{2-[1-(5-chloropyrimidin-2-yl)piperidin-
4-yl]cyclopropyl}ethoxy)-2-methylpyrimidine-4-carbonitrile
Rac-cis-1-[4-(2-{2-[1-(5-chloropyrimidin-2-yl)piperidin-4-
yl]cyclopropyl}ethoxy)phenyl]ethanone
Rac-cis-2-methyl-6-(2-{2-[1-(5-methylpyrazin-2-yl)piperidin-4-
yl]cyclopropyl}ethoxy)pyrimidine-4-carbonitrile
Rac-cis-6-(2-{2-[1-(5-chloropyrimidin-2-yl)piperidin-4-
yl]cyclopropyl}ethoxy)pyrimidine-4-carbonitrile
Rac-cis-4-(2-{2-[1-(5-chloropyrimidin-2-yl)piperidin-4-
yl]cyclopropyl}ethoxy)pyrimidine-2-carbonitrile
2-methyl-6-(1S,2R)-(2-{2-[1-(5-methylpyrimidin-2-yl)piperidin-4-
yl]cyclopropyl}ethoxy)pyrimidine-4-carbonitrile, 2-methyl-6-(1R,2S)-(2-{2-[1-(5-
methylpyrimidin-2-yl)piperidin-4-yl]cyclopropyl}ethoxy)pyrimidine-4-carbonitrile
Rac-cis-2-methyl-6-(2-{2-[1-(5-methylpyrimidin-2-yl)piperidin-4-
yl]cyclopropyl}ethoxy)pyrimidine-4-carbonitrile
Rac-cis-2,4-dimethyl-6-(2-{2-[1-(5-methylpyrimidin-2-yl)piperidin-4-
yl]cyclopropyl}ethoxy)pyrimidine TABLE 1-a-continued Rac-cis-6-(2-{2-[1-(5-chloro-4-methylpyrimidin-2-yl)piperidin-4-yl]cyclopropyl}ethoxy)-2-methylpyrimidine-4-carbonitrile
Rac-cis-6-(2-{2-[1-(5-chloropyridin-2-yl)piperidin-4-yl]cyclopropyl}ethoxy)-2-methylpyrimidine-4-carbonitrile
Rac-cis-6-(2-{2-[1-(4,5-dimethylpyrimidin-2-yl)piperidin-4-yl]cyclopropyl}ethoxy)-2-methylpyrimidine-4-carbonitrile
Rac-cis-6-(2-{2-[1-(5-chloro-4-methylpyridin-2-yl)piperidin-4-yl]cyclopropyl}ethoxy)-2-methylpyrimidine-4-carbonitrile
Rac-cis-6-(2-{2-[1-(5-fluoro-4-methylpyrimidin-2-yl)piperidin-4-yl]cyclopropyl}ethoxy)-2-methylpyrimidine-4-carbonitrile
Rac-cis-2-methyl-6-[2-(2-{1-[5-(trifluoromethyl)pyridin-2-yl]piperidin-4-yl}cyclopropyl)ethoxy]pyrimidine-4-carbonitrile
Rac-cis-5-chloro-2-(4-{2-[2-(pyridine-3-yloxy)ethyl]cyclopropyl}piperidin-1-yl)pyrimidine
Rac-cis-5-chloro-2-(4-{2-[2-(pyrimidin-4-yloxy)ethyl]cyclopropyl}piperidin-1-yl)pyrimidine
Rac-cis-5-(2-{2-[1-(5-chloropyrimidin-2-yl)piperidin-4-yl]cyclopropyl}ethoxy)nicotinonitrile
Rac-cis-6-(2-{2-[1-(5-chloropyrimidin-2-yl) piperidin-4-yl] cyclopropyl}ethoxy)-2-methylpyrimidine-4-carbonitrile
Rac-cis-4-(2-{2-[1-(5-chloropyrimidin-2-yl)piperidin-4-yl]cyclopropyl} ethoxy)-6-methylpyrimidine-2-carbonitrile
Rac-cis-6-(2-{2-[1-(5-fluoropyrimidin-2-yl)piperidin-4-yl]cyclopropyl}ethoxy)-2-methylpyrimidine-4-carbonitrile
Rac-cis-5-(2-{2-[1-(5-chloropyrimidin-2-yl)piperidin-4-yl]cyclopropyl}ethoxy)pyridine-2-carbonitrile
Rac-cis-5-chloro-2-(4-{2-[2-(pyridine-4-yloxy)ethyl]cyclopropyl}piperidin-1-yl)pyrimidine
5-chloro-2-(1S,2R)-{4-[2-(2-{[5-(1H-1,2,3-triazol-1-yl)pyridin-2-yl]oxy}ethyl)cyclopropyl]piperidin-1-yl}pyrimidine, 5-chloro-2-(1R,2S)-{4-[2-(2-{[5-(1H-1,2,3-triazol-1-yl)pyridin-2-yl]oxy}ethyl)cyclopropyl]piperidin-1-yl}pyrimidine
5-chloro-2-[4-((1R,2S)-2-{2-[3-fluoro-4-(5-methyl-1,3,4-oxadiazol-2-yl)phenoxy]ethyl}cyclopropyl)piperidin-1-yl]pyrimidine and 5-chloro-2-[4-((1S,2R)-2-{2-[3-fluoro-4-(5-methyl-1,3,4-oxadiazol-2-yl)phenoxy]ethyl}cyclopropyl)piperidin-1-yl]pyrimidine
rac cis-5-chloro-2-[4-(2-{2-[4-(1H-1,2,3-triazol-1-yl)phenoxy]ethyl}cyclopropyl)piperidin-1-yl]pyrimidine, 5-chloro-2-[4-((1S,2R)-2-{2-[4-(1H-1,2,3-triazol-1-yl)phenoxy]ethyl}cyclopropyl)piperidin-1-yl]pyrimidine and 5-chloro-2-[4-((1R,2S)-2-{2-[4-(1H-1,2,3-triazol-1-yl)phenoxy]ethyl}cyclopropyl)piperidin-1-yl]pyrimidine
5-fluoro-2-[4-((1R,2S)-2-{2-[4-(1H-1,2,3-triazol-1-yl)phenoxy]ethyl}cyclopropyl)piperidin-1-yl]pyrimidine and 5-fluoro-2-[4-((1S,2R)-2-{2-[4-(1H-1,2,3-triazol-1-yl)phenoxy]ethyl}cyclopropyl)piperidin-1-yl]pyrimidine
5-chloro-2-[4-((1R,2S)-2-{2-[4-(1H-tetrazol-1-yl)phenoxy]ethyl}cyclopropyl)piperidin-1-yl]pyrimidine and 5-chloro-2-[4-((1S,2R)-2-{2-[4-(1H-tetrazol-1-yl)phenoxy]ethyl}cyclopropyl)piperidin-1-yl]pyrimidine
5-chloro-2-[4-((1R,2S)-2-{2-[3-fluoro-4-(1H-tetrazol-1-yl)phenoxy]ethyl}cyclopropyl)piperidin-1-yl]pyrimidine and 5-chloro-2-[4-((1S,2R)-2-{2-[3-fluoro-4-(1H-tetrazol-1-yl)phenoxy]ethyl}cyclopropyl)piperidin-1-yl]pyrimidine
5-fluoro-2-[4-((1R,2S)-2-{2-[3-fluoro-4-(5-methyl-1,3,4-oxadiazol-2-yl)phenoxy]ethyl}cyclopropyl)piperidin-1-yl]pyrimidine and 5-fluoro-2-[4-((1S,2R)-2-{2-[3-fluoro-4-(5-methyl-1,3,4-oxadiazol-2-yl)phenoxy]ethyl}cyclopropyl)piperidin-1-yl]pyrimidine
rac-cis-2-[4-(2-{2-[3-fluoro-4-(5-methyl-1,3,4-oxadiazol-2-yl)phenoxy]ethyl}cyclopropyl)piperidin-1-yl]-5-methylpyrimidine
Rac-cis-2-[4-(2-{2-[3-fluoro-4-(5-methyl-1,3,4-oxadiazol-2-yl)phenoxy]ethyl}cyclopropyl)piperidin-1-yl]pyrimidine
Rac-cis-5-fluoro-2-[4-(2-{2-[3-fluoro-4-(5-methyl-1,3,4-oxadiazol-2-yl)phenoxy]ethyl}cyclopropyl)piperidin-1-yl]pyrimidine
Rac-cis-5-chloro-2-[4-(2-{2-[3-fluoro-4-(5-methyl-1,3,4-oxadiazol-2-yl)phenoxy]ethyl}cyclopropyl)piperidin-1-yl]-4-methylpyrimidine
Rac-cis-3,5-dichloro-2-[4-(2-{2-[3-fluoro-4-(5-methyl-1,3,4-oxadiazol-2-yl)phenoxy]ethyl}cyclopropyl)piperidin-1-yl]pyridine
Rac-cis-2-[4-(2-{2-[3-fluoro-4-(5-methyl-1,3,4-oxadiazol-2-yl)phenoxy]ethyl}cyclopropyl)piperidin-1-yl]-5-(trifluoromethyl)pyridinium trifluoroacetate
rac-cis-5-chloro-2-{4-[(2-{[4-(methylsulfonyl)phenoxy]methyl}cyclopropyl)methyl]piperidin-1-yl}pyrimidine
rac-cis 4-[(2-{[1-(5-chloropyrimidin-2-yl)piperidin-4-yl]methyl}cyclopropyl)methoxy]-N-cyclopropyl-2-fluorobenzamide
rac-cis-4-[(2-{[1-(5-chloropyrimidin-2-yl)piperidin-4-yl]methyl}cyclopropyl)methoxy]-6-methylpyrimidine-2-carbonitrile
rac-cis 4-[(2-{[1-(5-chloropyrimidin-2-yl)piperidin-4-yl]methyl}cyclopropyl)methoxy]-2-fluorobenzonitrile.

or a pharmaceutically acceptable salt thereof.

18. A compound selected from the group consisting of:

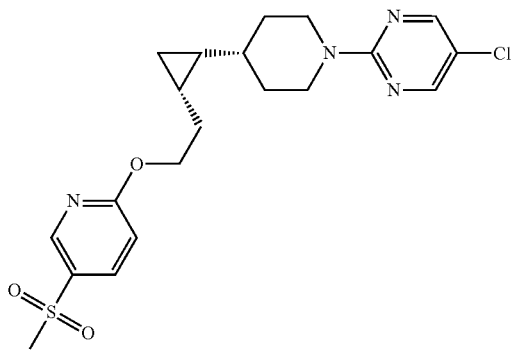

5-chloro-2-{4-[(1R, 2S)-2-(2-{[5-(methylsulfonyl)pyridin-2-yl]oxy}ethyl)cyclopropyl]piperidin-1-yl}pyrimidine

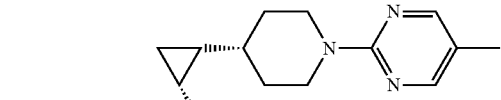

2-methyl-6-(2-{(1S,2R)-2-[1-(5-methylpyrimidin-2-yl)piperidin-4-yl]cyclopropyl}ethoxy)pyrimidine-4-carbonitrile

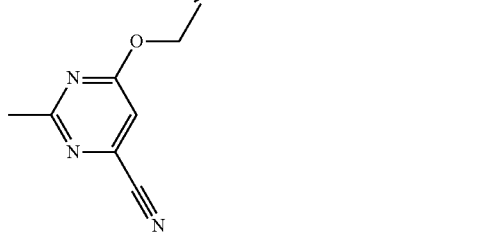

5-chloro-2-[4-((1R,2S)-2-{2-[4-(1H-1,2,3-triazol-1-yl)phenoxy]ethyl}cyclopropyl)piperidin-1-yl]pyrimidine

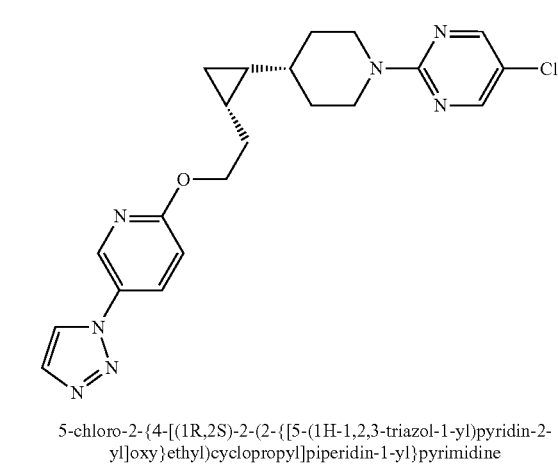

5-chloro-2-{4-[(1R,2S)-2-(2-{[5-(1H-1,2,3-triazol-1-yl)pyridin-2-yl]oxy}ethyl)cyclopropyl]piperidin-1-yl}pyrimidine or a pharmaceutically acceptable salt thereof.

19. A pharmaceutical composition comprised of a compound in accordance with claim 1, or a pharmaceutically acceptable salt thereof, in combination with a pharmaceutically acceptable carrier.

20. A method of treating type 2 diabetes in a mammalian patient in need of such treatment comprising administering to the patient a compound in accordance with claim 1, or a pharmaceutically acceptable salt thereof, in an amount that is effective to treat type 2 diabetes.

* * * * *